United States Patent [19]

Drumm et al.

[11] Patent Number: 5,438,033
[45] Date of Patent: Aug. 1, 1995

[54] SUBSTITUTED PYRIDINE HERBICIDES

[75] Inventors: Joseph E. Drumm, Newark; Renee M. Lett, Wilmington; Dennis R. Rayner, Centerville; Morris P. Rorer, Newark; Chi-Ping Tseng, Wilmington, all of Del.

[73] Assignee: E. I. duPont de Nemours and Company, Wilmington, Del.

[21] Appl. No.: 150,193

[22] PCT Filed: Jun. 9, 1992

[86] PCT No.: PCT/US92/04644
§ 371 Date: Dec. 9, 1993
§ 102(e) Date: Dec. 9, 1993

[87] PCT Pub. No.: WO92/22203
PCT Pub. Date: Dec. 23, 1992

Related U.S. Application Data

[63] Continuation-in-part of Ser. No. 713,909, Jun. 12, 1991, abandoned.

[51] Int. Cl.⁶ .................... A01N 43/40; A01N 43/36; A01N 43/84

[52] U.S. Cl. .................... 504/130; 504/134; 504/136; 504/138; 504/139; 504/225; 504/226; 504/244; 504/248; 504/249; 504/252; 504/254; 504/256; 504/257; 504/258; 504/259; 504/260

[58] Field of Search ............... 504/244, 225, 226, 248, 504/249, 252, 254, 256, 257, 258, 259, 260, 130, 134, 136, 138, 139

[56] References Cited

U.S. PATENT DOCUMENTS 3,495,969  2/1970  Driscoll .................. 71/94
4,473,395  9/1984  Hawkins et al. .......... 71/94
4,715,888  12/1987  Marzolph et al. ......... 71/93

FOREIGN PATENT DOCUMENTS 3939233  3/1991  Germany.

OTHER PUBLICATIONS

Bird et al. "Herbicidal 5-pyridylcyclohexane-1,3-dione derivatives" EP 104,876. Abstract CA 101:110737g. 1984.
Rynbrandt et al. *J. Med. Chem.* 1979,22(5),525-528.
Shramm et al. Khim-Geterotsikl Soedin, 1984(3),372-375. (Translation).

*Primary Examiner*—S. Mark Clardy

[57] ABSTRACT

This invention relates to certain herbicidal pyridine compounds, agriculturally suitable compositions and a method of use of herbicidal pyridine compounds.

10 Claims, No Drawings

SUBSTITUTED PYRIDINE HERBICIDES

This application is a continuation filed under 35 USC 371 of PCT/US92/04644, which is a continuation-in-part of Ser. No. 07/713,909, filed Jun. 12, 1991, now abandoned.

BACKGROUND OF THE INVENTION

This invention relates to agriculturally suitable compositions of certain herbicidal pyridine compounds and a method for their use as selective preemergent or postemergent herbicides for controlling the growth of undesired vegetation in crops such as rice.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. There are many products commercially available for these purposes, but the search continues for products which are more effective, less costly and environmentally safe.

U.S. Pat. No. 3,495,969 discloses compounds of the following structure as herbicides:

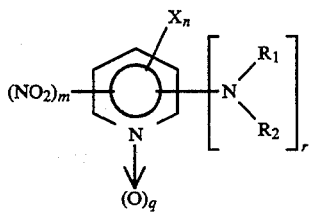

wherein $R_1$ and $R_2$ are H, $C_1$–$C_8$ alkyl, $C_3$–$C_6$ cycloalkyl, etc.;

X is H, CN, OH, halogen, sulfoxide, sulfonic acid, sulfone, —CON($R_2$)$_2$, carboxyl, haloalkyl, $C_1$–$C_6$ alkyl, haloalkoxy, alkoxy, aryl, aryloxy, haloaryloxy, carbalkoxy, carbonyl, thiol, thioalkoxy, alkylthio, arylthio and halarylthio;

m is 1 or 2;

n is at least 1;

q is 0 or 1;

r is 0, 1 or 2.

SUMMARY OF THE INVENTION

This invention is directed to an agriculturally suitable composition for controlling the growth of undesired vegetation in a crop comprising an effective amount of a compound of Formula I

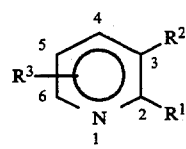

wherein $R^1$ is Cl, Br, I, OCH$_3$, OCHF$_2$ or OCF$_3$;

$R^2$ is CN, CO$_2R^4$, CHO, C(X)NR$^{17}$R$^{18}$, C(S)OR$^6$, C≡CH, CHR$^{19}$OR$^{20}$, CH=NOR$^7$ or CH=CR$^{21}$R$^{22}$;

$R^3$ is n-propyl; $C_4$–$C_{10}$ alkyl; n-propyl or $C_4$–$C_7$ alkyl substituted with one or more halogen, OR$^8$, SR$^9$ or NR$^{10}$R$^{11}$; $C_1$–$C_3$ alkyl substituted with OR$^{16}$, CO$_2$(-$C_1$–$C_2$ alkyl) or phenyl optionally substituted with one or more CH$_3$, CF$_3$, OCH$_3$, SCH$_3$ or halogen; $C_3$–$C_6$ cycloalkyl; CH$_2$($C_3$–$C_6$ cycloalkyl); phenyl optionally substituted with one or more CH$_3$, CF$_3$, OCH$_3$, SCH$_3$ or halogen; $C_2$–$C_6$ alkenyl optionally substituted with one or more halogen or CO$_2$ ($C_1$–$C_2$ alkyl); OR$^{12}$; SR$^{13}$; or NR$^{14}$R$^{15}$;

$R^4$ is H, $C_1$–$C_2$ alkyl,

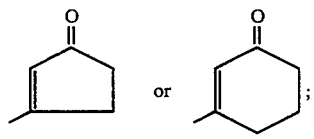

$R^6$, $R^7$, $R^8$, $R^9$, $R^{10}$ and $R^{11}$ are independently H or $C_1$–$C_2$ alkyl;

$R^{12}$ and $R^{13}$ are independently $C_2$–$C_{10}$ alkyl optionally substituted with one or more halogen, OR$^8$, SR$^9$ or NR$^{10}$R$^{11}$; phenyl optionally substituted with one or more CH$_3$, CF$_3$, OCH$_3$, SCH$_3$ or halogen; or benzyl;

$R^{14}$ and $R^{15}$ are independently H or $C_1$–$C_2$ alkyl, or may be taken together as —(CH$_2$)$_4$—, —(CH$_2$)$_5$— or —(CH$_2$CH$_2$OCH$_2$CH$_2$)—;

$R^{16}$ is H, $C_1$–$C_8$ alkyl; benzyl optionally substituted with one or more CH$_3$, CF$_3$, OCH$_3$, SCH$_3$ or halogen; or phenyl optionally substituted with one or more CH$_3$, CF$_3$, OCH$_3$, SCH$_3$ or halogen;

$R^{17}$ is H, $C_1$–$C_2$ alkyl or phenyl optionally substituted with one or more CH$_3$, CF$_3$, OCH$_3$, SCH$_3$ or halogen;

$R^{18}$ is H, $C_1$–$C_2$ alkyl, $C_3$–$C_6$ cycloalkyl, CH$_2$($C_3$–$C_6$ cycloalkyl), O($C_1$–$C_4$ alkyl), O-allyl or may be taken together with $R^{17}$ as —(CH$_2$)$_4$—, —(CH$_2$)$_5$— or —(CH$_2$CH$_2$OCH$_2$CH$_2$)—;

$R^{19}$ is H or $C_1$–$C_2$ alkyl;

$R^{20}$ is H or C(O)CH$_3$;

$R^{21}$ and $R^{22}$ are independently H, CN, CO$_2R^4$, C(X)NR$^{17}$R$^{18}$ or halogen;

X is O or S;

or their N-oxides or agriculturally suitable salts thereof provided that when $R^1$ is Cl, Br or I, and $R^2$ is CN, CO$_2R^4$ or C(O)NR$^{17}$R$^{18}$, then $R^3$ is other than optionally substituted 5-phenyl and at least one of the following: surfactant, solid, or liquid diluent.

This invention also is directed to a method of using the agriculturally suitable compositions for controlling the growth of undesired vegetation in a crop by applying to the locus of the crop an effective amount of the compounds or composition of the invention without the proviso that removes certain structures from the compositions of the invention.

This invention also is directed to herbicidal mixtures of the compounds of the invention with one or two other known herbicides for controlling the growth of undesired vegetation in a rice crop. The preferred mixtures of the invention comprise a compound of Formula I when $R^1$ is Br or Cl, $R^2$ is C(O)NH$_2$ and $R^3$ is CH$_2$CH$_2$CH(CH$_3$)$_2$, one or more herbicidal compound selected from the group consisting of bensulfuron methyl; mefenacet; metsulfuron methyl; pyrazosulfuron ethyl; butachlor; N-[2-(2-methoxyethoxyphenylsulfonyl]-N$^1$-4,6-dimethoxy-1,3,5-triazin-2-yl urea; N-[[(4,6-dimethoxypyrimidin-2-yl)amino]carbonyl]-1-methyl-4-(2-methyl-2H-tetrazol-5-yl)-1H-pyrazole-5- sulfonamide; S,S-dimethyl 2-(difluoromethyl)-4-(2-methylpropyl)-6-(trifluoromethyl)-3,5-pyridinecarbothiate; and 3-chloro-N [[(4,6-dimethoxy-2-pyrimidinyl)amino]carbonyl]imidazo-[1,2-a]pyridine-3-sulfonamide.

In the above definitions, the term "alkyl" includes straight chain or branched alkyl, e.g., methyl, ethyl, n-propyl, isopropyl or the different butyl isomers, etc. Cycloalkyl includes cyclopropyl, cyclobutyl, cyclopentyl and cyclohexyl. The term "halogen" means fluorine, chlorine, bromine or iodine.

The compositions and methods of use that are preferred for reasons including ease of synthesis and/or greater herbicidal efficacy are:

1. The compositions and the methods for controlling the growth of undesired vegetation by applying to the locus of the crop compositions comprising compounds of Formula I wherein $R^1$ is Cl, Br, I or $OCH_3$;
$R^2$ is CN, $CO_2R^4$, CHO, $C(X)NH_2$, $C(X)NH(C_1-C_2$ alkyl), $C(X)N(C_1-C_2$ alkyl$)_2$, $C(S)OR^6$ or C≡CH;
$R^3$ is n-propyl, $C_4-C_6$ alkyl, $C_3-C_6$ cycloalkyl or phenyl;
$R^4$ is H or $C_1-C_2$ alkyl; and
$R^6$ is $C_1-C_2$ alkyl.

2. The compositions and methods of comprising compounds of Formula I wherein
$R^1$ is Cl, Br or I;
$R^2$ is CN, $CO_2H$, $CO_2CH_3$, $CO_2CH_2CH_3$, CHO, $C(O)NH_2$, $C(O)NHCH_3$, $C(O)N(CH_3)_2$, $CH_2OH$ or CH=$NOR^7$;
$R^3$ is n-propyl; $C_4-C_7$ alkyl; $C_2$ alkyl substituted with phenyl optionally substituted with one or more $CH_3$, $CF_3$, $OCH_3$, $SCH_3$ or halogen; $CH_2(C_3-C_6$ cycloalkyl); or phenyl optionally substituted with one or more $CH_3$, $CF_3$, $OCH_3$, $SCH_3$ or halogen.

3. The compositions and methods of Preferred 2 wherein
$R^1$ is Cl or Br;
$R^2$ is CN, $CO_2H$ or $C(O)NH_2$;
$R^3$ is $C_4-C_7$ alkyl or $CH_2(C_3-C_6$ cycloalkyl).

4. The compositions and methods of Preferred 3 wherein
$R^3$ is substituted at the 6-pyridine position.

5. The compositions and methods of Preferred 4 wherein $R^2$ is $C(O)NH_2$.

Specifically preferred methods of use involve the compounds which are 2-bromo-6-(3-methylbutyl)-3-pyridinecarboxamide and 2-chloro-6-(3-methylbutyl)-3-pyridinecarboxamide.

DETAILED DESCRIPTION OF THE INVENTION

Compounds of Formula I wherein $R^3$ is alkyl and where $R^2$ is cyano have been synthesized before. The synthesis of 2-chloro-3-cyano-6-isobutylpyridine is described in detail in J. Am. Chem. Soc. (1947), Vol. 69, 2670. It is also shown schematically below (Scheme I).

SCHEME I

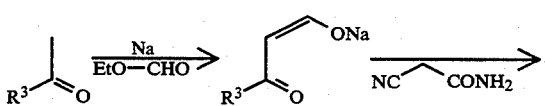

-continued
SCHEME I

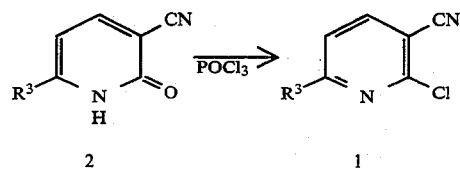

The synthesis of any variations in $R^3$ would be expected to follow along the same lines. Other substituents for $R^2$ may be synthesized using a variety of transformations on 2.

Alternatively, the compounds of type 2 where $R^3$ is phenyl or substituted phenyl (as described) can be synthesized by first treatment of methyl ketone of $R^3$ with dimethylformamide dimethylacetal at a temperature from 25°-100° C. for 2-48 hours to form an intermediate as described in Tetrahedron (1979), 1675 which upon treatment with cyanoacetamide under acidic conditions such as acetic acid or hydrochloric acid in a solvent such as toluene, benzene or tetrahydrofuran at a temperature 25° to 110° for 2-48 hours to provide compound of type 2 (Scheme Ia).

SCHEME Ia

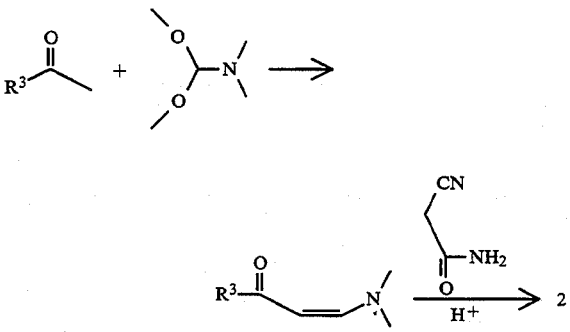

The compound 2 can either be treated with triphenylphosphine and carbon tetrachloride at a temperature 25°-100° for 2-48 hours or treatment with a mixture of phosphorus oxychloride and phosphorus pentachloride at a temperature 25° to 100° for 2-24 hours to provide compounds of type 1.

The compound 2 can be treated with chlorodifluoromethane or chlorotrifluoromethane to provide compound 1 where $R^1$ is $OCF_2H$ or $OCF_3$, respectively, by following the literature references J. Heterocyclic Chem. 1990, 27, 807; Synthesis 1990, 604 and 681. The cyano group may be hydrolyzed to a carboxylic acid according to the aforementioned paper. Subsequent treatment of the acid with a mixture of phosphorus oxychloride and phosphorus pentachloride converts the acid to the acid chloride and exchanges the hydroxy group for a chlorine atom to provide 3 (Scheme II; J. Med. Chem. (1979), Vol. 22, 525). Alternatively, treatment of the acid with phosphorus tribromide would be expected to provide the corresponding 2-bromo-pyridine compound. Acid chloride 3 may be treated with an alcohol $R^6$—OH to provide the corresponding ester under conditions well known to those versed in the art. In analogous fashion, 3 may be treated with ammonia or a primary or secondary amine, $R^{17}R^{18}NH$,

SCHEME II

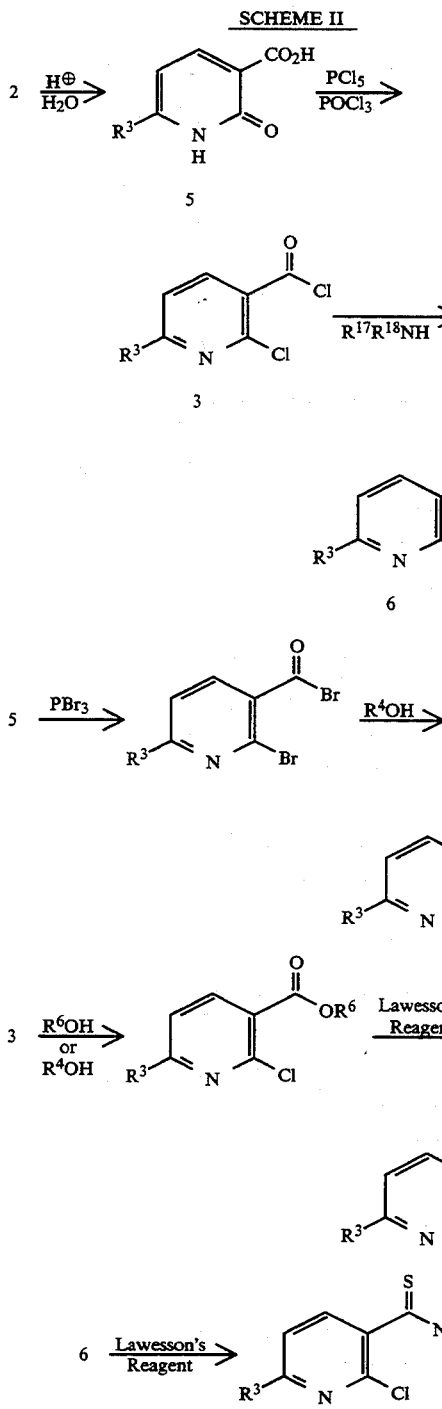

preferably 5% aqueous sodium hydroxide at about 25° to 100° C. for 1 to 24 hours. The carboxylic acid of 1 then can be converted to acid halide 3 which in turn can be converted to substituted amides as shown in Scheme II.

The compound 1 can be treated with sodium methoxide in methanol at about 0° to 80° C. for 1 to 24 hours to provide compounds of Formula I where $R^1$=$OCH_3$, $R^2$=CN and $R^3$ is as described.

The 2-Cl of compound 1 can be exchanged with iodide by using sodium iodide or potassium iodide in a solvent such-as acetone or methylethylketone at about 25° to 120° C. for 1 to 48 hours.

More variety and flexibility of synthesis may be provided by reduction of the cyano group to aldehyde 4 with diisobutylaluminum hydride (DIBAL-H) according to standard procedures known to one skilled in the art as shown in Scheme III. The secondary alcohol can be prepared by treatment of the aldehyde 4 with ($C_1$-$C_2$ alkyl)-MgBr.

The aldehyde 4 can be converted to oximes with treatment of $NH_2OR^7$ to provide 4A and to olefins 4B upon treatment with active methylene compounds of type $CH_2R^{21}R^{22}$ (wherein $R^{21}$ or $R^{22}$ is a nitrile, ester or amide) and a base by one skilled in the art. The acetylene may be synthesized from the aldehyde via the Corey-Fuchs homologation as shown in Scheme III ($CBr_4$/$PPh_3$ to form dibromoolefin, followed by n-BuLi, rearrangement and quench with acid; see *Tetrahedron Lett.* (1972), 3769).

SCHEME III

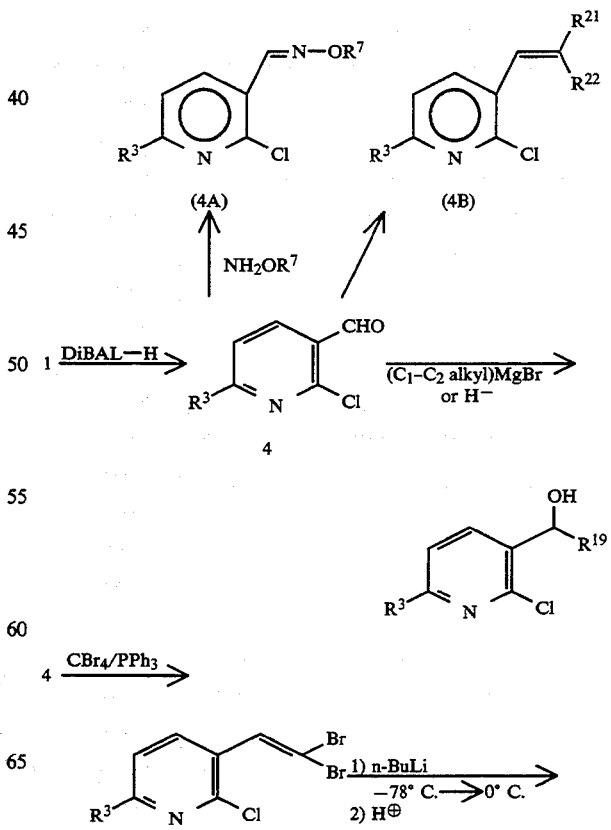

to provide the corresponding amide. The thioesters and thioamides of this family may be synthesized via treatment of the aforementioned esters and amides with Lawesson's reagent (*Tetrahedron* (1979), 2433 and references cited therein).

Alternatively the cyano group of 1 can be converted to an amide according to *J. Med. Chem.* 1985, 28, 1790 using 30% aqueous hydrogen peroxide, methanol and sodium hydroxide system or *Synthesis* 1989, 950, using 30% hydrogen peroxide, potassium carbonate and dimethylsulfoxide. The cyano group of 1 can be converted to carboxylic acid using about 5-20% aqueous base such as sodium hydroxide or potassium hydroxide, -continued
SCHEME III

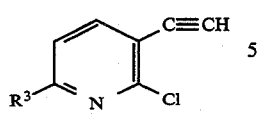

The 2-chloro-3-cyano-6-methyl pyridine can be converted to primary bromide 4C by treatment with one equivalent of N-bromosuccinimide in a solvent such a dichloromethane or carbon tetrachloride at a temperature 25° to 100° C. for 1 to 24 hours. The resulting bromide can be utilized to form compounds of type 4D as shown in Scheme IIIa. Thus 4C can be treated with a base such as triethylamine, pyridine or sodium hydride and a $C_1$–$C_8$ alcohol in a solvent such as tetrahydrofuran, dimethylformamide or dioxane at about 0° to 100° C.

SCHEME IIIa

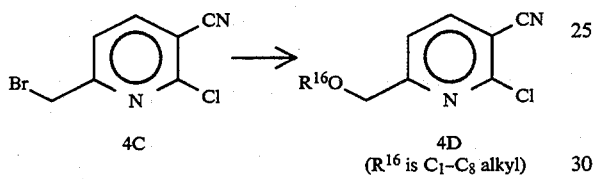

4C            4D
($R^{16}$ is $C_1$–$C_8$ alkyl)

The compounds of type 4G can be synthesized by reacting compound 4F under basic conditions with alcohols, phenols, mercaptans, thiophenols and substituted amines as shown in Scheme IIIb. The synthesis of 4F is known (*Agnew Chem. Int. Ed. Engl.* 1980 388).

SCHEME IIIb

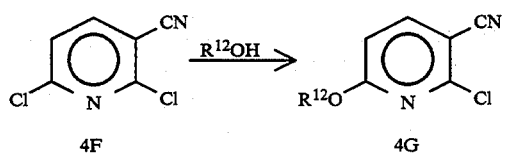

4F           4G

The pyridines with an alkyl substituent on the 5-position may be synthesized by following literature reference *J. Org. Chem.* (1978) 43 (12) 2529 and U.S. Pat. No. 4,987,232 and as shown in Scheme IV. The 3-ethoxy-2-alkyl propenals may be synthesized according to a literature procedure (*Tetrahedron Lett* (1984), 5243). Treatment of this aldehyde with cyanoacetamide would provide, after acid catalyzed cyclization, the intermediate 5.

SCHEME IV

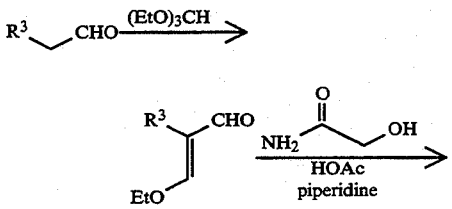

-continued
SCHEME IV

Intermediate 5 may then be elaborated to the required pyridines by the same transformations as already described in Schemes II and III.

The pyridines with an alkyl substituent on the 4-position may be synthesized as shown in Scheme V.

SCHEME V

Ethyl cyanoacetate and orthoesters will condense to form the 3-alkoxy, -3-alkylidene derivatives with distillation of alcohol. (*Chem. Abs.* 52:11909i, U.S. Pat. No. 2,824,121). Condensation with an acetaldehyde equivalent such as the corresponding enamel or silyl ether followed by ammoniolysis should provide 6. Further elaboration of 6 according to procedures described in Schemes II and III would provide quantities of the required pyridines.

The preparation of the compounds of this invention is further illustrated by the following specific examples. Unless otherwise indicated, temperatures are in degrees centigrade.

EXAMPLE 1

1,2-Dihydro-2-oxo-6-(3-methylbutyl)-3-pyridine carbonitrile

To a suspension of 23.25 g of sodium methoxide in 500 mL of diethylether under a nitrogen atmosphere and at 0° C., a solution of 29.6 g of ethylformate and 45.6 g 4-methyl-2-pentanone in 100 mL of diethylether was added dropwise while maintaining the reaction temperature at 0° C. After stirring at 25° C. for 2 hours a heavy precipitate formed. The diethylether was removed and to the residual solid was added a solution of 33.4 g cyanoacetamide in 150 mL water and piperidine acetate (prepared by adding piperidine to 4 mL of glacial acetic acid in 20 mL water until the solution is just basic to litmus). The mixture was heated under reflux for 2 hours. At the end of this time 100 mL of water was added and the solution was acidified (to litmus) with acetic acid, causing separation of product as yellow precipitate. The mixture was cooled in an ice bath for 2 hours and product was collected on suction filter, washed with 3×100 mL water, suction-dried and finally dried in vacuo at 25° C. overnight to afford 54 g of the title compound as a yellow solid; m.p. 110°–112° C.

NMR (CDCl$_3$) ppm δ 7.82 (d, 1H); 6.23 (d, 1H); 2.73 (d, 2H), 1.67 (m, 3H); 0.996 (d, 6H).

IR (Nujol): 2200 cm$^{-1}$ (C≡N), 1650 cm$^{-1}$ (C=O).

EXAMPLE 2

Compound 8

The suspension of 15.2 g of the compound of Example 1 in 22 mL of phosphorus oxychloride was heated at 90° C., and 19 g of phosphorus pentachloride was added in small portions over a 30-minute period. The mixture was heated at 90° C. for additional 1.5 hours and excess phosphorus oxychloride was removed in vacuo. The residue was dissolved in (1:1) 200 mL methylene chloride and 200 ml water. The methylene chloride layer was collected, washed with water, dried over magnesium sulfate, filtered and the filtrate evaporated to leave yellow oil. Silica gel flash column chromatography (8:2 hexane-ethylacetate) afforded after evaporation of the eluant 11.55 g of the subject compound as a brown oil.

NMR (CDCl$_3$) ppm δ 7.9 (d, 1H); 7.23 (d, 1H); 2.87 (m, 2H); 1.64 (m, 3H); 0.965 (d, 6H).

IR (Neat): 2210 cm$^{-1}$ (C≡N).

EXAMPLE 3

Compound 13

To 1.95 g of the compound of Example 2 in 15 mL of methanol, a solution of 0.5 g sodium hydroxide in 2 mL of water was added followed by 2.2 mL of 30% aqueous hydrogen peroxide at 25° C. The reaction mixture was stirred for 24 hours and 50 mL of water was added and the mixture was extracted with 2×25 mL of methylene chloride. The methylene chloride extracts were washed with 25 mL each of aqueous saturated sodium bisulfite and water. The organic layer was dried over magnesium sulfate, filtered and the filtrate was evaporated to yield 1.2 g of title compound as a white solid, m.p. 119°–120° C.

NMR (CDCl$_3$) ppm δ 8.2 (d, 1H); 7.2 (d, 1H); 6.85 (s, 1H); 6.0 (s, 1H); 2.77 (m, 2H); 1.6 (m, 3H); 0.965 (d, 6H).

IR (Nujol): 3320, 1650 cm$^{-1}$ (C=O).

EXAMPLE 4

Compound 34

To a solution of 7.36 g 'sodium hydroxide in 147 mL water, 8.68 g of compound of Example 2 was added and heated to reflux for 4 hours. The mixture was cooled to 0° C. (ice bath) and acidified to pH 2 (litmus) with concentrated hydrochloric acid. The mixture was then extracted with 3×100 mL methylene chloride. The organic extracts were washed with 50 ml each of water and saturated sodium chloride solution. The organic layer was dried over magnesium sulfate, filtered and filtrate was evaporated to afford 8.0 g of the title compound as a yellow oil.

NMR (CDCl$_3$) ppm δ 8.28 (d, 1H); 7.23 (d, 1H); 2.8 (m, 2H); 1.6 (m, 2H); 1.2 (m, 1H); 0.97 (d, 6H).

IR (Neat): 1700 cm$^{-1}$, (C=O).

EXAMPLE 5

Compound 39

By the procedure of Example 2, 15.2 g of the product of Example 1 was reacted with 40 g phosphorus oxybromide and 10 g of phosphorus pentabromide. The isolated crude product was purified by silica gel flash column chromatography (hexanes:ethylacetate 8:2) to afford after evaporation of the eluant 13.0 g of title compound as a dark brown oil.

NMR (CDCl$_3$) ppm δ 7.8 (d, 1H); 7.2 (d, 1H); 2.8 (t, 2H); 1.6 (m, 3H), 0.9 (d, 6H).

IR (Neat): 2220 cm$^{-1}$ (C≡N).

EXAMPLE 6

Compound 41

By the procedure of Example 3, 1.6 g of the product of Example 5 was reacted with 0.3 g sodium hydroxide in 1.2 mL of water and 1.4 mL of 30% aqueous hydrogen peroxide. The isolated crude product was purified by silica gel flash column chromatography (hexane:ethylacetate 1:1) to provide after evaporation of the eluant 0.64 g of title compound as a white solid, m.p. 110°–112° C.

NMR (CDCl$_3$) ppm δ 8.0 (d, 1H); 7.2 (d, 1H); 6.5 (b, s, 1H); 6.0 (b, s, 1H); 2.8 (m, 2H); 1.6 (m, 3H); 0.96 (d, 6H).

IR (Neat): 3340 cm$^{-1}$ (NH$_2$); 1650 cm$^{-1}$ (C=O).

Using the procedures of Schemes I–V and Examples 1–6, one skilled in the art can prepare the compounds in Tables 1–3.

TABLE 1

$$\text{Structure: pyridine with } R^1, R^2, R^3 \text{ substituents}$$

$R^1 = Cl, R^2 = C(O)NH_2$

| $R^3$ | $R^3$ | $R^3$ |
|---|---|---|
| $(CH_2)_2CH_3$ | cyclopropyl | $CH_2SCH_2(3CF_3-C_6H_4)$ |
| $(CH_2)_3CH_3$ | cyclobutyl | $CH_2S(2Cl-C_6H_4)$ |
| $(CH_2)_4CH_3$ | cyclopentyl | $CH_2S(4CH_3-C_6H_4)$ |
| $(CH_2)_5CH_3$ | cyclohexyl | $CH_2S(2,4Cl-C_6H_3)$ |
| $(CH_2)_6CH_3$ | $CH_2OCH_2CH_3$ | $CH_2S(3SCH_3-C_6H_4)$ |
| $(CH_2)_7CH_3$ | $CH_2OCH_2CH_2CH_3$ | $CH_2S(2,6Cl-C_6H_3)$ |
| $(CH_2)_8CH_3$ | $CH_2OCH_2CH(CH_3)_2$ | $CH_2S(C_6H_5)$ |
| $(CH_2)_9CH_3$ | $CH_2OCH_2(C_6H_5)$ | $CH_2S(3CF_3-C_6H_4)$ |
| $CH_2CH(CH_3)_2$ | $CH_2OCH_2(3CF_3-C_6H_4)$ | $CH_2S(2Cl-C_6H_4)$ |
| $CH_2CH_2CH(CH_3)_2$ | $CH_2OCH_2(2Cl-C_6H_4)$ | $CH_2S(4CH_3-C_6H_4)$ |
| $CH_2CH_2CH(CH_3)CH_3$ | $CH_2OCH_2(3SCH_3-C_6H_4)$ | $CH_2S(2,6Cl-C_6H_3)$ |
| $CH_2CH_2CH(CH_3)CH_2CH_3$ | $CH_2OCH_2(4Cl-C_6H_4)$ | $CH_2S(2,4Cl-C_6H_3)$ |
| $CH_2CH_2CH(CH_3)CH_2CH_2CH_3$ | $CH_2OCH_2(2,4F-C_6H_3)$ | $CH_2NHCH_2CH_3$ |
| $CH_2CH(CH_3)CH_2CH_2CH_3$ | $CH_2O(C_6H_5)$ | $CH_2NHCH_2CH_2CH_3$ |
| $CH_2CH(CH_3)CH_2OCH_3$ | $CH_2O(3CF_3-C_6H_4)$ | $CH_2NHCH_2CH(CH_3)_2$ |
| $CH_2CH(CH_3)-S-CH_2CH_3$ | $CH_2O(4CF_3-C_6H_4)$ | $CH_2NHCH_2(3CF_3-C_6H_4)$ |
| $CH_2CH_2CH_2NHCH_2CH_3$ | $CH_2O(2Cl-C_6H_4)$ | $CH_2NHCH_2(2Cl-C_6H_4)$ |
| $CH_2CH_2CH_2SCH_3$ | $CH_2O(3SCH_3-C_6H_4)$ | $CH_2NH(C_6H_5)$ |
| $CH_2CF_2CH(CH_3)_2$ | $CH_2O(2CH_3-C_6H_4)$ | $CH_2NH(2Cl-C_6H_4)$ |
| $CH_2CF_2CH_2CF_2CH_3$ | $CH_2O(4Cl-C_6H_4)$ | $CH_2N(CH_3)(2Cl-C_6H_4)$ |
| $CH_2$-cyclopropyl | $CH_2O(2,4Cl-C_6H_3)$ | $OCH_2CH_2CH_3$ |
| $CH_2$-cyclobutyl | $CH_2SCH_2CH_3$ | $OCH_2(CH_2)_2CH_3$ |
| $CH_2$-cyclopentyl | $CH_2SCH_2CH_2CH_3$ | $OCH_2(CH_2)_3CH_3$ |
| $CH_2$-cyclohexyl | $CH_2SCH_2CH(CH_3)_2$ | $OCH_2(CH_2)_5CH_3$ |
| $R^3$ | $CH_2SCH_2(C_6H_5)$ | $OCH_2C(C_6H_5)$ |
| $OCH_2(3CF_3-C_6H_4)$ | $NHCH_2(C_6H_5)$ | $R^3$ |
| $OCH_2(2Cl-C_6H_4)$ | $NHCH_2(3CF_3-C_6H_4)$ | $2Cl-C_6H_4$ |
| $OCH_2CH(CH_3)_2$ | $NHCH_2(2Cl-C_6H_4)$ | $3CH_3-C_6H_4$ |
| $O(C_6H_5)$ | $NHCH_2(4CH_3-C_6H_4)$ | $3OCH_3-C_6H_4$ |
| $O(3CF_3-C_6H_4)$ | $NHCH_2(2,4Cl-C_6H_3)$ | $2CF_3-C_6H_4$ |
| $O(2Cl-C_6H_4)$ | $NHCH_2(2,6Cl-C_6H_3)$ | $2,4Cl-C_6H_3$ |
| $O(4SCH_3-C_6H_4)$ | $NH(C_6H_5)$ | $2,6Cl-C_6H_3$ |
| $O(2,4Cl-C_6H_4)$ | $NH(3CF_3-C_6H_4)$ | $2SCH_3-C_6H_4$ |
| $SCH_2CH_2CH_3$ | $NH(2Cl-C_6H_4)$ | $CH_2(C_6H_5)$ |
| $SCH_2(CH_2)_2CH_3$ | $NH(3CH_3-C_6H_4)$ | $CH_2(3CF_3-C_6H_4)$ |
| $SCH_2(CH_2)_3CH_3$ | $NH(2,4Cl-C_6H_4)$ | $CH_2(4Cl-C_6H_4)$ |
| $SCH_2(CH_2)_5CH_3$ | $NH(2,6Cl-C_6H_3)$ | $CH_2(2,4Cl-C_6H_3)$ |
| $SCH_2(C_6H_5)$ | $N(CH_3)(3CF_3-C_6H_4)$ | $CH_2(3SCH_3-C_6H_4)$ |
| $SCH_2(3SCH_3-C_6H_4)$ | $N(CH_3)CH_2CH_2CH_3$ | $CH_2(3OCH_3-C_6H_4)$ |
| $SCH_2(2OCH_3-C_6H_4)$ | $N(CH_3)CH_2(C_6H_5)$ | $CH_2(3Cl-C_6H_4)$ |
| $SCH_2(2Cl-C_6H_4)$ | $N(CH_2)_4$ | $CH_2(2,6F-C_6H_3)$ |
| $SCH_2(2,4-C_6H_3)$ | $N(CH_2)_5$ | $CH_2(2,6Cl-C_6H_3)$ |
| $SCH_2(4CF_3-C_6H_4)$ | $N(CH_2)_6$ | $CH_2(3,4F-C_6H_3)$ |
| | $N(CH_2CH_2-OCH_2CH_2)_2$ | |

-continued

| | | |
|---|---|---|
| S(CH₃)₃ | CH₂CO₂CH₃ | |
| SCH₂CH(CH₃)₂ | CH₂CH₂CO₂CH₃ | R¹ = Br, R² = C(O)NH₂ |
| S(C₆H₅) | CH₂CH₂CO₂CH₂CH₃ | R³ |
| S(3CF₃—C₆H₄) | CH₂CH₂OCH₂CH₃ | (CH₂)₂CH₃ |
| S(2Cl—C₆H₄) | CH₂CH₂SCH₂CH₃ | (CH₂)₃CH₃ |
| S(4OCH₃—C₆H₄) | CH₂CH₂—NHCH₂CH₃ | (CH₂)₄CH₃ |
| S(2,4Cl—C₆H₃) | CH₂CH₂N(CH₃)CH₂CH₃ | (CH₂)₅CH₃ |
| S(2,6F—C₆H₃) | CH=CH(CH₃)₂ | (CH₂)₆CH₃ |
| 2(3CH₃—C₆H₄) | CH₂CH=CH₂ | (CH₂)₇CH₃ |
| NHCH₂CH₂CH₃ | CH₂CH=CH—CH₃ | (CH₂)₈CH₃ |
| NHCH₂(CH₂)₂CH₃ | CH=CH—CH₂CH₂—Cl | (CH₂)₉CH₃ |
| NHCH₂(CH₂)₃CH₃ | CH₂CH₂CH—ClCH₂—Cl | CH₂CH(CH₃)₂ |
| NHCH₂CH(CH₃)₂ | C₆H₅ | CH₂CH₂CH(CH₃)₂ |
| R³ | 3CF₃—C₆H₄ | CH₂CH₂CH₂CH(CH₃)₂ |
| CH₂CH₂CH(CH₃)CH₂CH₂CH₃ | CH₂O(3SCH₃—C₆H₄) | R³ |
| CH₂CH(CH₃)CH₂CH₂CH₂CH₃ | CH₂O(2CH₃—C₆H₄) | OCH₂(CH₂)₅CH₃ |
| CH₂CH(CH₃)CH₂CH₂CH₂CH₃ | CH₂O(4Cl—C₆H₄) | OCH₂C(C₆H₅) |
| CH₂CH₂CH₂OCH₂CH₃ | CH₂O(2,4Cl—C₆H₃) | OCH₂(3CF₃—C₆H₄) |
| CH₂CH₂CH₂CH₂OCH₃ | CH₂SCH₂CH₃ | OCH₂(2Cl—C₆H₄) |
| CH₂CH₂CH₂—S—CH₂CH₃ | CH₂SCH₂CH₂CH₃ | OCH₂CH(CH₃)₂ |
| CH₂CH₂CH₂NHCH₂CH₃ | CH₂SCH₂CH(CH₃)₂ | O(C₆H₅) |
| CH₂CF₂CH(CH₃)₂ | CH₂SCH₂CH(C₆H₅) | O(3CF₃—C₆H₄) |
| CH₂CH₂CH₂CF₂CH₃ | CH₂SCH₂(3CF₃—C₆H₄) | O(2Cl—C₆H₄) |
| CH₂cyclopropyl | CH₂S(2Cl—C₆H₄) | O(4SCH₃—C₆H₄) |
| CH₂-cyclobutyl | CH₂S(4CH₃—C₆H₄) | O(2,4Cl—C₆H₃) |
| CH₂-cyclopentyl | CH₂S(2,6Cl—C₆H₃) | SCH₂CH₂CH₃ |
| CH₂-cyclohexyl | CH₂S(2,4Cl—C₆H₃) | SCH₂(CH₂)₂CH₃ |
| cyclopropyl | CH₂S(3SCH₃—C₆H₄) | SCH₂(CH₂)₃CH₃ |
| cyclobutyl | CH₂S(2,6Cl—C₆H₅) | SCH₂(CH₂)₅CH₃ |
| cyclopentyl | CH₂S(C₆H₅) | SCH₂(C₆H₅) |
| cyclohexyl | CH₂S(3CF₃—C₆H₄) | SCH₂(3SCH₃—C₆H₄) |
| CH₂OCH₂CH₃ | CH₂S(2Cl—C₆H₄) | SCH₂(2OCH₃—C₆H₄) |
| CH₂OCH₂CH₂CH₃ | CH₂S(4CH₃—C₆H₄) | SCH₂(2Cl—C₆H₄) |
| CH₂OCH₂CH(CH₃)₂ | CH₂S(2,6Cl—C₆H₃) | SCH₂(2,4-C₆H₃) |
| CH₂OCH₂(C₆H₅) | CH₂S(2,4Cl—C₆H₃) | SCH₂(4CF₃—C₆H₄) |
| CH₂OCH₂(3CF₃—C₆H₄) | CH₂NHCH₂CH₃ | S(CH₃)₃ |
| CH₂OCH₂(2Cl—C₆H₄) | CH₂NHCH₂CH₂CH₃ | SCH₂CH(CH₃)₂ |
| CH₂OCH₂(3SCH₃—C₆H₄) | CH₂NHCH₂C(C₆H₅) | S(C₆H₅) |
| CH₂OCH₂(4Cl—C₆H₄) | CH₂NHCH₂C(CH₃)₂ | S(3CF₃—C₆H₄) |
| CH₂OCH₂(2,4F—C₆H₃) | CH₂NHCH₂(3CF₃—C₆H₄) | S(2Cl—C₆H₄) |
| CH₂OCH₂OCH₂CH₃ | CH₂NHCH₂(2Cl—C₆H₄) | S(4OCH₃—C₆H₄) |
| CH₂O(C₆H₅) | CH₂NH(C₆H₅) | S(2,4Cl—C₆H₃) |
| CH₂O(3CF₃—C₆H₄) | CH₂NH(2Cl—C₆H₄) | S(2,6F—C₆H₃) |
| CH₂O(4CF₃—C₆H₄) | CH₂NH(2Cl—C₆H₄) | 2(3CH₃—C₆H₄) |
| CH₂O(3CF₃—C₆H₅) | CH₂N(CH₃)(2Cl—C₆H₄) | NHCH₂CH₂CH₃ |
| CH₂O(2Cl—C₆H₄) | OCH₂CH₂CH₃ | NHCH₂(CH₂)₂CH₃ |
| | OCH₂(CH₂)₂CH₃ | NHCH₂(CH₂)₄CH₃ |
| | OCH₂(CH₂)₃CH₃ | R³ |
| NHCH₂(CH₂)₃CH₃ | R³ | CH₂CH₂CH(CH₃)₂ |
| NHCH₂CH(CH₃)₂ | C₆H₅ | CH₂CH₂CH₂CH(CH₃)₂ |
| NHCH₂(C₆H₅) | 3CF₃—C₆H₄ | CH₂CH₂CH(CH₃)CH₂CH₃ |
| NHCH₂(3CF₃—C₆H₄) | 2Cl—C₆H₄ | CH₂CH(CH₃)CH₂CH₂CH₃ |
| CH₂O(2Cl—C₆H₄) | 3CH₃—C₆H₄ | CH₂CH(CH₃)CH₂CH₂CH₃ |
| NHCH₂(2Cl—C₆H₄) | 3OCH₃—C₆H₄ | CH₂CH(CH₂CH₃)CH₂CH₂CH₃ |

-continued

| | |
|---|---|
| NHCH2(4CH3—C6H4) | 2CF3—C6H4 |
| NHCH2(2,4Cl—C6H3) | 2,4Cl—C6H3 |
| NHCH2(2,6Cl—C6H3) | 2,6Cl—C6H3 |
| NH(C6H5) | 2SCH3—C6H4 |
| NH(3CF3—C6H4) | CH2(C6H5) |
| NH(2Cl—C6H4) | CH2(3CF3—C6H4) |
| NH(3CH3—C6H4) | CH2(2Cl—C6H4) |
| NH(2,4Cl—C6H3) | CH2(4Cl—C6H4) |
| NH(2,6Cl—C6H3) | CH2(2,4Cl—C6H3) |
| N(CH3)(3CF3—C6H4) | CH2(3SCH3—C6H4) |
| N(CH3)CH2CH2CH3 | CH2(3OCH3—C6H4) |
| N(CH2)4 | CH2(3Cl—C6H4) |
| N(CH2)5 | CH2(2,6F—C6H3) |
| N(CH2)6 | CH2(2,6Cl—C6H3) |
| N(CH2CH2—OCH2CH2)2 | CH2(3,4F—C6H3) |
| CH2CO2CH3 | |
| CH2CH2CO2CH2CH3 | R1 = I, R2 = C(O)NH2 |
| CH2CH2CO2CH3 | R3 |
| CH2H2OCH2CH3 | (CH2)2CH3 |
| CH2CH2SCH2CH3 | (CH2)3CH3 |
| CH2CH2—NHCH3 | (CH2)4CH3 |
| CH2CH2N(CH3)CH2CH3 | (CH2)5CH3 |
| CH=CH(CH3)2 | (CH2)6CH3 |
| CH2CH2CH=CH2 | (CH2)7CH3 |
| CH2CH=CH—CH3 | (CH2)8CH3 |
| CH=CH—CH2CH2—Cl | (CH2)9CH3 |
| CH2CH2CH—ClCH2—Cl | CH2CH(CH3)2 |
| | R3 |
| CH2O(4CF3—C6H4) | OCH2(CH2)2CH3 |
| CH2O(2Cl—C6H4) | OCH2(CH2)3CH3 |
| CH2O(3SCH3—C6H4) | OCH2(CH2)5CH3 |
| CH2O(2CH3—C6H4) | OCH2C(C6H5) |
| CH2O(4Cl—C6H4) | OCH2(3CF3—C6H4) |
| CH2O(2,4Cl—C6H3) | OCH2(2Cl—C6H4) |
| CH2SCH2CH3 | OCH2CH(CH3)2 |
| CH2SCH2CH(CH3)2 | O(C6H5) |
| CH2SCH2CH2CH3 | O(3CF3—C6H4) |
| CH2SCH2CH(C6H5) | O(2Cl—C6H4) |
| CH2SCH2(3CF3—C6H4) | O(4SCH3—C6H4) |
| CH2S(2Cl—C6H4) | O(2,4Cl—C6H3) |
| CH2S(4CH3—C6H4) | SCH2CH2CH3 |
| CH2S(2,4Cl—C6H3) | SCH2(CH2)2CH3 |
| CH2S(3SCH3—C6H4) | SCH2(CH2)3CH3 |
| CH2S(2,6Cl—C6H3) | SCH2(CH2)5CH3 |
| CH2S(C6H5) | SCH2C(C6H5) |
| CH2S(3SCH3—C6H4) | SCH2(3SCH3—C6H4) |
| CH2S(2OCH3—C6H4) | SCH2(2OCH3—C6H4) |
| CH2S(2Cl—C6H4) | SCH2(2Cl—C6H3) |
| CH2S(2,6Cl—C6H3) | SCH2(2,4-C6H3) |
| CH2S(4CF3—C6H4) | SCH2(4CF3—C6H4) |
| CH2NHCH2CH3 | S(CH3)3 |
| CH2NHCH2CH2CH3 | SCH2CH(CH3)2 |
| CH2NHCH2C(C6H5) | S(C6H5) |
| | CH2CH2CH2OCH2CH3 |
| | CH2CH2CH2OCH3 |
| | CH2CH2CH2—S—CH2CH3 |
| | CH2CH2CH2SCH3 |
| | CH2CH2CH2NHCH2CH3 |
| | CH2CF2CH2CH(CH3)2 |
| | CH2CF2CH2CF2CH3 |
| | CH2-cyclopropyl |
| | CH2-cyclobutyl |
| | CH2-cyclopentyl |
| | CH2-cyclohexyl |
| | cyclopropyl |
| | cyclobutyl |
| | cyclopentyl |
| | cyclohexyl |
| | CH2OCH2CH3 |
| | CH2OCH2CH2CH3 |
| | CH2OCH2CH(CH3)2 |
| | CH2OCH2CH(C6H5) |
| | CH2OCH2(3CF3—C6H4) |
| | CH2OCH2(2Cl—C6H4) |
| | CH2OCH2(3SCH3—C6H4) |
| | CH2OCH2(4Cl—C6H4) |
| | CH2OCH2(2,4F—C6H3) |
| | CH2OCH2OCH2CH2CH3 |
| | CH2O(C6H5) |
| | CH2O(3CF3—C6H4) |
| | R3 |
| | NHCH2(CH2)2CH3 |
| | NHCH2(CH2)4CH3 |
| | NHCH2(CH2)5CH3 |
| | NHCH2(C6H5) |
| | NHCH2(3CF3—C6H4) |
| | NHCH2(2Cl—C6H4) |
| | NHCH24CH3—C6H4) |
| | NHCH2(2,4Cl—C6H3) |
| | NHCH2(2,6Cl—C6H3) |
| | NH(C6H5) |
| | NH(3CF3—C6H4) |
| | NH(2Cl—C6H4) |
| | NH(3CH3—C6H4) |
| | NH(2,4Cl—C6H3) |
| | NH(2,6Cl—C6H3) |
| | N(CH3)(3CF3—C6H4) |
| | N(CH3)CH2CH2CH3 |
| | N(CH2)4 |
| | N(CH2)5 |
| | N(CH2)6 |
| | N(CH2CH2—OCH2CH2)2 |
| | CH2CO2CH3 |
| | CH2CH2CO2CH2CH3 |
| | CH2CH2CO2CH3 |

-continued

| | |
|---|---|
| CH₂NHCH₂CH(CH₃)₂ | S(3CF₃—C₆H₄) | CH₂CH₂OCH₂CH₃ |
| CH₂NHCH₂(3CF₃—C₆H₄) | S(2Cl—C₆H₄) | CH₂CH₂SCH₂CH₃ |
| CH₂NHCH₂(2Cl—C₆H₄) | S(4OCH₃—C₆H₄) | CH₂CH₂—NHCH₂CH₃ |
| CH₂NH(C₆H₅) | S(2,4Cl—C₆H₃) | CH₂CH₂N(CH₃)CH₂CH₃ |
| CH₂NH(2Cl—C₆H₄) | S(2,6F—C₆H₃) | CH=CH(CH₃)₂ |
| CH₂N(CH₃)(2Cl—C₆H₄) | 2(3CH₃—C₆H₄) | CH₂CH=CH₂ |
| OCH₂CH₂CH₃ | NHCH₂CH₂CH₃ | CH₂CH=CH—CH₃ |
| R³ | R³ | R³ |
| CH=CH—CH₂CH₂—Cl | (CH₂)₉CH₃ | CH₂O(C₆H₅) |
| CH₂CH₂CH—ClCH₂—Cl | CH₂CH(CH₃)₂ | CH₂O(3CF₃—C₆H₄) |
| C₆H₅ | CH₂CH₂CH(CH₃)₂ | CH₂O(4CF₃—C₆H₄) |
| 3CF₃—C₆H₄ | CH₂CH₂CH₂CH(CH₃)₂ | CH₂O(2Cl—C₆H₄) |
| 2Cl—C₆H₄ | CH₂CH₂CH(CH₃)CH₂CH₂CH₃ | CH₂O(3SCH₃—C₆H₄) |
| 3CH₃—C₆H₄ | CH₂CH(CH₃)CH₂CH₂CH₃ | CH₂O(2CH₃—C₆H₄) |
| 3OCH₃—C₆H₄ | CH₂CH(CH₃)CH₂CH₂CH₃ | CH₂O(4Cl—C₆H₄) |
| 2CF₃—C₆H₄ | CH₂CH₂CH₂OCH₂CH₃ | CH₂O(2,4Cl—C₆H₃) |
| 2,4Cl—C₆H₃ | CH₂CH₂CH₂OCH₃ | CH₂SCH₂CH₃ |
| 2,6Cl—C₆H₃ | CH₂CH₂CH₂—S—CH₂CH₃ | CH₂SCH₂CH₂CH₃ |
| 2SCH₃—C₆H₄ | CH₂CH₂CH₂SCH₃ | CH₂SCH₂CH(CH₃)₂ |
| CH₂(C₆H₅) | CH₂CH₂CH₂NHCH₂CH₃ | CH₂S(C₆H₅) |
| CH₂(3CF₃—C₆H₄) | CH₂CF₂CH(CH₃)₂ | CH₂SCH₂(3CF₃—C₆H₄) |
| CH₂(2Cl—C₆H₄) | CH₂CH₂CH₂CF₂CH₃ | CH₂S(2Cl—C₆H₄) |
| CH₂(4Cl—C₆H₄) | CH₂-cyclopropyl | CH₂S(4CH₃—C₆H₄) |
| CH₂(2,4Cl—C₆H₃) | CH₂-cyclobutyl | CH₂S(2,4Cl—C₆H₃) |
| CH₂(3SCH₃—C₆H₄) | CH₂-cyclopentyl | CH₂S(3SCH₃—C₆H₄) |
| CH₂(3OCH₃—C₆H₄) | CH₂-cyclohexyl | CH₂S(2,6Cl—C₆H₃) |
| CH₂(3Cl—C₆H₄) | cyclopropyl | CH₂S(C₆H₅) |
| CH₂(2,6F—C₆H₃) | cyclobutyl | CH₂S(3CF₃—C₆H₄) |
| CH₂(2,6Cl—C₆H₃) | cyclopentyl | CH₂S(2Cl—C₆H₄) |
| CH₂(3,4F—C₆H₃) | cyclohexyl | CH₂S(4CH₃—C₆H₄) |
| | CH₂OCH₂CH₃ | CH₂S(2,4Cl—C₆H₃) |
| R¹ = OCH₃, R² = C(O)NH₂ | CH₂OCH₂CH₂CH₃ | CH₂NHCH₂CH₃ |
| R³ | CH₂OCH₂CH(CH₃)₂ | CH₂NHCH₂CH₂CH₃ |
| (CH₂)₂CH₃ | CH₂OCH₂(C₆H₅) | CH₂NHCH₂C(C₆H₅) |
| (CH₂)₃CH₃ | CH₂OCH₂(3CF₃—C₆H₄) | CH₂NHCH₂CH(CH₃)₂ |
| (CH₂)₄CH₃ | CH₂OCH₂(2Cl—C₆H₄) | CH₂NHCH₂CH(CH₃)₂ |
| (CH₂)₅CH₃ | CH₂OCH₂(3SCH₃—C₆H₄) | CH₂NHCH₂(3CF₃—C₆H₄) |
| (CH₂)₆CH₃ | CH₂OCH₂(4Cl—C₆H₄) | CH₂NHCH₂(2Cl—C₆H₄) |
| (CH₂)₇CH₃ | CH₂OCH₂(2,4F—C₆H₃) | CH₂NHCH(C₆H₅) |
| (CH₂)₈CH₃ | CH₂OCH₂OCH₂CH₃ | CH₂NH(2Cl—C₆H₄) |
| R³ | R³ | R³ |
| CH₂N(CH₃)(2Cl—C₆H₄) | 2(3CH₃—C₆H₄) | CH₂CH₂CH=CH₂ |
| OCH₂CH₂CH₃ | NHCH₂(CH₃)₂CH₃ | CH=CH—CH=CH—CH₃ |
| OCH₂(CH₂)₂CH₃ | NHCH₂(CH₂)₃CH₃ | CH=CH—CH₂CH₂—Cl |
| OCH₂(CH₂)₃CH₃ | NHCH₂(CH₂)₄CH₃ | CH₂CH₂CH=ClCH₂—Cl |
| OCH₂(CH₂)₅CH₃ | NHCH₂(CH₂)₅CH₃ | C₆H₅ |
| OCH₂(C₆H₅) | NHCH(C₆H₅) | 3CF₃—C₆H₄ |
| OCH₂(3CF₃—C₆H₄) | NHCH₂(3CF₃—C₆H₄) | 2Cl—C₆H₄ |
| OCH₂(2Cl—C₆H₄) | NHCH₂(2Cl—C₆H₄) | 3Cl—C₆H₄ |
| OCH₂(CH₃)₂ | NHCH₂(4Cl—C₆H₃) | 3OCH₃—C₆H₄ |
| O(C₆H₅) | NHCH₂(2,4Cl—C₆H₃) | 2CF₃—C₆H₃ |
| O(3CF₃—C₆H₄) | NHCH₂(2,4Cl—C₆H₃) | 2,4Cl—C₆H₃ |
| O(2Cl—C₆H₄) | NHCH₂(2,6Cl—C₆H₃) | 2,6Cl—C₆H₃ |

-continued

| | | |
|---|---|---|
| O(4SCH₃—C₆H₄) | NH(C₆H₅) | 2SCH₃—C₆H₄ |
| O(2,4Cl—C₆H₃) | NH(3CF₃—C₆H₄) | CH₂(C₆H₅) |
| SCH₂CH₂CH₃ | NH(2Cl—C₆H₄) | CH₂(3CF₃—C₆H₄) |
| SCH₂(CH₂)₂CH₃ | NH(3CH₃—C₆H₄) | CH₂(2Cl—C₆H₄) |
| SCH₂(CH₂)₃CH₃ | NH(2,4Cl—C₆H₃) | CH₂(4Cl—C₆H₄) |
| SCH₂(CH₂)₅CH₃ | NH(2,6CH₃—C₆H₃) | CH₂(2,4Cl—C₆H₃) |
| SCH₂(C₆H₅) | N(CH₃)(3CF₃—C₆H₄) | CH₂(3SCH₃—C₆H₄) |
| SCH₂(3SCH₃—C₆H₄) | N(CH₃)CH₂CH₂CH₃ | CH₂(3OCH₃—C₆H₄) |
| SCH₂(2OCH₃—C₆H₄) | N(CH₂)₄ | CH₂(3Cl—C₆H₄) |
| SCH₂(2Cl—C₆H₄) | N(CH₂)₅ | CH₂(2,6F—C₆H₃) |
| SCH₂(2,4-C₆H₃) | N(CH₂)₆ | CH₂(2,6Cl—C₆H₃) |
| SCH₂(4CF₃—C₆H₄) | N(CH₂CH₂—OCH₂CH₂)₂ | CH₂(3,4F—C₆H₃) |
| S(CH₃)₃ | CH₂CO₂CH₃ | |
| SCH(CH₃)₂ | CH₂CH₂CO₂CH₂CH₃ | R¹ = OCF₂H, R² = C(O)NH₂ |
| S(C₆H₅) | CH₂CH₂CO₂CH₃ | R³ |
| S(3CF₃—C₆H₄) | CH₂CH₂OCH₂CH₃ | (CH₂)₂CH₃ |
| S(2Cl—C₆H₄) | CH₂CH₂SCH₂CH₃ | (CH₂)₃CH₃ |
| S(4OCH₃—C₆H₄) | CH₂CH₂—NHCH₂CH₃ | (CH₂)₄CH₃ |
| S(2,4Cl—C₆H₃) | CH₂CH₂N(CH₃)CH₂CH₃ | (CH₂)₅CH₃ |
| S(2,6F—C₆H₃) | CH=CH(CH₃)₂ | (CH₂)₆CH₃ |
| R³ | R³ | R³ |
| (CH₂)₇CH₃ | CH₂OCH₂(2,4F—C₆H₃) | CH₂NH(C₆H₅) |
| (CH₂)₈CH₃ | CH₂CH₂OCH₂CH₂CH₃ | CH₂NH(2Cl—C₆H₄) |
| (CH₂)₉CH₃ | CH₂O(C₆H₅) | CH₂N(CH₃)(2Cl—C₆H₄) |
| CH₂CH(CH₃)₂ | CH₂O(3CF₃—C₆H₄) | OCH₂CH₂CH₃ |
| CH₂CH₂CH(CH₃)₂ | CH₂O(4CF₃—C₆H₄) | OCH₂(CH₂)₂CH₃ |
| CH₂CH₂CH₂CH(CH₃)₂ | CH₂O(2Cl—C₆H₄) | OCH₂(CH₂)₃CH₃ |
| CH₂CH₂CH(CH₃)CH₂CH₂CH₃ | CH₂O(3SCH₃—C₆H₄) | OCH₂(CH₂)₅CH₃ |
| CH₂CH(CH₂CH₃)CH₂CH₂CH₃ | CH₂O(2CH₃—C₆H₄) | OCH₂C(C₆H₅) |
| CH₂CH(CH₂CH₃)CH₂CH₃ | CH₂O(4Cl—C₆H₄) | OCH₂(3CF₃—C₆H₄) |
| CH₂CH₂CH₂CH₂OCH₂CH₃ | CH₂O(2,4Cl—C₆H₃) | OCH₂(2Cl—C₆H₄) |
| CH₂CH₂CH₂—S—CH₂CH₃ | CH₂SCH₂CH₃ | OCH₂CH(CH₃)₂ |
| CH₂CH₂CH₂CH₂SCH₃ | CH₂SCH₂CH₂CH₃ | O(C₆H₅) |
| CH₂CH₂CH₂NHCH₂CH₃ | CH₂SCH₂(C₆H₅) | O(3CF₃—C₆H₄) |
| CH₂CF₂CF₂CF₃ | CH₂SCH₂(3CF₃—C₆H₄) | O(2Cl—C₆H₄) |
| CH₂-cyclopropyl | CH₂S(2Cl—C₆H₄) | O(4SCH₃—C₆H₄) |
| CH₂-cyclobutyl | CH₂S(4CH₃—C₆H₄) | O(2,4Cl—C₆H₃) |
| CH₂-cyclopentyl | CH₂S(2,4Cl—C₆H₃) | SCH₂CH₂CH₃ |
| CH₂-cyclohexyl | CH₂S(3SCH₃—C₆H₄) | SCH₂(CH₂)₂CH₃ |
| cyclopropyl | CH₂S(2,6Cl—C₆H₃) | SCH₂(CH₂)₃CH₃ |
| cyclobutyl | CH₂S(C₆H₅) | SCH₂(CH₂)₅CH₃ |
| cyclopentyl | CH₂S(3CF₃—C₆H₄) | SCH₂(C₆H₅) |
| cyclohexyl | CH₂S(2Cl—C₆H₄) | SCH₂(3SCH₃—C₆H₄) |
| CH₂OCH₂CH₃ | CH₂S(4CH₃—C₆H₄) | SCH₂(2OCH₃—C₆H₄) |
| CH₂OCH₂CH₂CH₃ | CH₂S(2,6Cl—C₆H₃) | SCH₂(2Cl—C₆H₄) |
| CH₂OCH₂CH(CH₃)₂ | CH₂S(2,4Cl—C₆H₃) | SCH₂(2,4-C₆H₃) |
| CH₂OCH₂CH₂CH₂CH₃ | CH₂NHCH₂CH₃ | SCH₂(4CF₃—C₆H₄) |
| CH₂OCH₂(C₆H₅) | CH₂NHCH₂CH₂CH₃ | S(CH₃)₃ |
| CH₂OCH₂(3CF₃—C₆H₄) | CH₂NHCH₂C(C₆H₅) | SCH₂CH(CH₃)₂ |
| CH₂OCH₂(2Cl—C₆H₄) | CH₂NHCH₂CH(CH₃)₂ | S(C₆H₅) |
| CH₂OCH₂(3SCH₃—C₆H₄) | CH₂NHCH₂(3CF₃—C₆H₄) | S(3CF₃—C₆H₄) |
| CH₂OCH₂(4Cl—C₆H₄) | CH₂NHCH₂(2Cl—C₆H₄) | S(2Cl—C₆H₄) |
| | | S(4OCH₃—C₆H₄) |

-continued

| R³ | R³ | R³ |
|---|---|---|
| S(2,4Cl—C₆H₃) | CH₂CH₂N(CH₃)CH₂CH₃ | (CH₂)₅CH₃ |
| S(2,6F—C₆H₃) | CH=CH(CH₃)₂ | (CH₂)₆CH₃ |
| 2(3CH₃—C₆H₃) | CH₂CH₂CH=CH₂ | (CH₂)₇CH₃ |
| NHCH₂CH₂CH₃ | CH₂CH=CH—CH₃ | (CH₂)₈CH₃ |
| NHCH₂(CH₂)₂CH₃ | CH=CH—CH₂CH₂—Cl | (CH₂)₉CH₃ |
| NHCH₂(CH₂)₃CH₃ | CH₂CH₂CH—ClCH₂—Cl | CH₂CH(CH₃)₂ |
| NHCH₂(CH₂)₅CH₃ | C₆H₅ | CH₂CH₂CH(CH₃)₂ |
| NHCH₂CH(CH₃)₂ | 3CF₃—C₆H₄ | CH₂CH₂CH₂CH(CH₃)₂ |
| NH(C₆H₅) | 2Cl—C₆H₄ | CH₂CH(CH₃)CH₂CH₂CH₃ |
| NHCH₂(3CF₃—C₆H₄) | 3CH₃—C₆H₄ | CH₂CH(CH₃)CH₂CH₂CH₃ |
| NHCH₂(2Cl—C₆H₄) | 3OCH₃—C₆H₄ | CH₂CH(CH₃CH₃)CH₂CH₃ |
| NHCH₂(4CH₃—C₆H₄) | 2CF₃—C₆H₄ | CH₂CH₂CH₂OCH₃ |
| NHCH₂(2,4Cl—C₆H₃) | 2,4Cl—C₆H₃ | CH₂CH₂CH₂OCH₃ |
| NHCH₂(2,6Cl—C₆H₃) | 2,6Cl—C₆H₃ | CH₂CH₂CH₂—S—CH₂CH₃ |
| NH(C₆H₅) | 2SCH₃—C₆H₄ | CH₂CH₂CH₂CH₂SCH₃ |
| NH(3CF₃—C₆H₄) | CH₂(C₆H₅) | CH₂CH₂CH₂NHCH₂CH₃ |
| NH(2Cl—C₆H₄) | CH₂(3CF₃—C₆H₄) | CH₂CF₂CH(CH₃)₂ |
| NH(3CH₃—C₆H₄) | CH₂(2Cl—C₆H₄) | CH₂CH₂CH₂CF₂CH₃ |
| NH(2,4Cl—C₆H₃) | CH₂(4Cl—C₆H₄) | CH₂-cyclopropyl |
| NH(2,6Cl—C₆H₃) | CH₂(2,4Cl—C₆H₃) | CH₂-cyclobutyl |
| N(CH₃)(3CF₃—C₆H₄) | CH₂(3SCH₃—C₆H₄) | CH₂-cyclopentyl |
| N(CH₃)CH₂CH₂CH₃ | CH₂(3OCH₃—C₆H₄) | CH₂-cyclohexyl |
| N(CH₂)₄ | CH₂(3Cl—C₆H₄) | cyclopropyl |
| N(CH₂)₅ | CH₂(2,6F—C₆H₃) | cyclobutyl |
| N(CH₂)₆ | CH₂(2,6Cl—C₆H₃) | cyclopentyl |
| N(CH₂CH₂—OCH₂CH₂)₂ | CH₂(3,4F—C₆H₃) | cyclohexyl |
| CH₂CO₂CH₃ | | CH₂OCH₂CH₃ |
| CH₂CH₂CO₂CH₂CH₃ | R¹ = Cl, R² = C≡N | CH₂OCH₂CH₂CH₃ |
| CH₂CH₂CO₂CH₂CH₃ | R³ | CH₂OCH₂CH(CH₃)₂ |
| CH₂CH₂OCH₂CH₃ | (CH₂)₂CH₃ | CH₂OCH₂(C₆H₅) |
| CH₂CH₂OCH₂CH₂CH₃ | (CH₂)₃CH₃ | CH₂OCH₂(3CF₃—C₆H₄) |
| CH₂CH₂SCH₂CH₃ | (CH₂)₄CH₃ | CH₂OCH₂(2Cl—C₆H₄) |
| CH₂CH₂—NHCH₂CH₃ | R³ | R³ |
| R³ | CH₂NHCH₂(3CF₃—C₆H₄) | S(2Cl—C₆H₄) |
| CH₂OCH₂(3SCH₃—C₆H₄) | CH₂NHCH₂(2Cl—C₆H₄) | S(4OCH₃—C₆H₄) |
| CH₂OCH₂(2,4Cl—C₆H₄) | CH₂NH(C₆H₅) | S(2,4Cl—C₆H₃) |
| CH₂OCH₂(2,4F—C₆H₃) | CH₂NH(2Cl—C₆H₄) | S(2,6F—C₆H₃) |
| CH₂OCH₂OCH₂CH₃ | CH₂N(CH₃)(2Cl—C₆H₄) | 2(3CH₃—C₆H₄) |
| CH₂O(C₆H₅) | OCH₂CH₂CH₃ | NHCH₂CH₂CH₃ |
| CH₂O(3CF₃—C₆H₄) | OCH₂(3CF₃—C₆H₄) | NHCH₂(CH₂)₂CH₃ |
| CH₂O(4CF₃—C₆H₄) | OCH₂(CH₂)₂CH₃ | NHCH₂(CH₂)₄CH₃ |
| CH₂O(2Cl—C₆H₄) | OCH₂(2Cl—C₆H₄) | NHCH₂(CH₂)₅CH₃ |
| CH₂O(3SCH₃—C₆H₄) | OCH₂(CH₂)₅CH₃ | NHCH₂CH(CH₃)₂ |
| CH₂O(2Cl—C₆H₄) | OCH₂C(C₆H₅) | NHCH₂(C₆H₅) |
| CH₂O(4Cl—C₆H₄) | OCH₂(3CF₃—C₆H₄) | NHCH₂(3CF₃—C₆H₄) |
| CH₂O(2,4Cl—C₆H₄) | OCH₂(2Cl—C₆H₄) | NHCH₂(2Cl—C₆H₄) |
| CH₂O(2,4Cl—C₆H₃) | OCH₂CH(CH₃)₂ | NHCH₂(4CH₃—C₆H₄) |
| CH₂SCH₂CH₃ | O(C₆H₅) | NHCH₂(2,4Cl—C₆H₃) |
| CH₂SCH₂CH(CH₃)₂ | O(3CF₃—C₆H₄) | NHCH₂(2,6Cl—C₆H₃) |
| CH₂SCH₂(C₆H₅) | O(2Cl—C₆H₄) | NH(C₆H₅) |
| CH₂SCH₂(3CF₃—C₆H₄) | O(4SCH₃—C₆H₄) | NH(3CF₃—C₆H₄) |
| CH₂S(2Cl—C₆H₄) | O(2,4Cl—C₆H₃) | NH(2Cl—C₆H₄) |
| CH₂S(4CH₃—C₆H₄) | SCH₂CH₂CH₃ | |

-continued

| | | |
|---|---|---|
| CH₂S(2,4Cl—C₆H₃) | SCH₂(CH₂)₂CH₃ | NH(3CH₃—C₆H₄) |
| CH₂S(3SCH₃—C₆H₄) | SCH₂(CH₂)₃CH₃ | NH(2,4Cl—C₆H₃) |
| CH₂S(2,6Cl—C₆H₃) | SCH₂(CH₂)₅CH₃ | NH(2,6Cl—C₆H₃) |
| CH₂S(C₆H₅) | SCH₂(C₆H₅) | N(CH₃)(3CF₃—C₆H₄) |
| CH₂S(3CF₃—C₆H₄) | SCH₂(3SCH₃—C₆H₄) | N(CH₃)CH₂CH₂CH₃ |
| CH₂S(2Cl—C₆H₄) | SCH₂(2OCH₃—C₆H₄) | N(CH₂)₄ |
| CH₂S(4CH₃—C₆H₄) | SCH₂(2Cl—C₆H₄) | N(CH₂)₅ |
| CH₂S(2,6Cl—C₆H₃) | SCH₂(2,4-C₆H₃) | N(CH₂)₆ |
| CH₂S(2,4Cl—C₆H₃) | SCH₂(4CF₃—C₆H₄) | N(CH₂CH₂—OCH₂CH₂)₂ |
| CH₂NHCH₂CH₃ | S(CH₃)₃ | CH₂CO₂CH₃ |
| CH₂NHCH₂CH₂CH₃ | SCH₂CH(CH₃)₂ | CH₂CH₂CO₂CH₂CH₃ |
| CH₂NHCH₂C(C₆H₅) | S(C₆H₅) | CH₂CH₂CO₂CH₃ |
| CH₂NHCH₂CH(CH₃)₂ | S(3CF₃—C₆H₄) | CH₂CH₂OCH₂CH₃ |
| R³ | R³ | R³ |
| CH₂CH₂SCH₂CH₃ | (CH₂)₃CH₃ | CH₂OCH₂(3CF₃—C₆H₄) |
| CH₂CH₂—NHCH₂CH₃ | (CH₂)₄CH₃ | CH₂OCH₂(2Cl—C₆H₄) |
| CH₂CH₂N(CH₃)CH₂CH₃ | (CH₂)₅CH₃ | CH₂OCH₂(3SCH₃—C₆H₄) |
| CH=CH(CH₃)₂ | (CH₂)₆CH₃ | CH₂OCH₂(4Cl—C₆H₄) |
| CH₂CH₂CH=CH₂ | (CH₂)₇CH₃ | CH₂OCH₂(2,4F—C₆H₃) |
| CH=CH—CH=CH₃ | (CH₂)₈CH₃ | CH₂OCH₂OCH₂CH₃ |
| CH=CH—CH₂CH₂—Cl | (CH₂)₉CH₃ | CH₂O(C₆H₅) |
| CH₂CH₂CH—ClCH₂—Cl | CH₂CH(CH₃)₂ | CH₂O(3CF₃—C₆H₄) |
| C₆H₅ | CH₂CH₂CH(CH₃)₂ | CH₂O(4CF₃—C₆H₄) |
| 3CF₃—C₆H₄ | CH₂CH₂CH(CH₃)CH₂CH₂CH₃ | CH₂O(2Cl—C₆H₄) |
| 2Cl—C₆H₄ | CH₂CH₂CH(CH₃)CH₂CH₂CH₃ | CH₂O(3SCH₃—C₆H₄) |
| 3CH₃—C₆H₄ | CH₂CH(CH₃)CH₂CH₂CH₃ | CH₂O(2OCH₃—C₆H₄) |
| 3OCH₃—C₆H₄ | CH₂CH(CH₃)CH₂OCH₂CH₃ | CH₂O(4Cl—C₆H₄) |
| 2CF₃—C₆H₄ | CH₂CH₂CH₂OCH₂CH₃ | CH₂O(2,4Cl—C₆H₃) |
| 2,4Cl—C₆H₃ | CH₂CH₂CH₂OCH₃ | CH₂SCH₂CH₃ |
| 2,6Cl—C₆H₃ | CH₂CH₂CH₂—S—CH₂CH₃ | CH₂SCH₂CH₂CH₃ |
| 2SCH₃—C₆H₄ | CH₂CH₂CH₂NHCH₂CH₃ | CH₂SCH₂CH(CH₃)₂ |
| CH₂(C₆H₅) | CH₂CF₂CH(CH₃)₂ | CH₂SCH₂(C₆H₅) |
| CH₂(3CF₃—C₆H₄) | CH₂CH₂CH(CH₃)₂ | CH₂SCH₂(3CF₃—C₆H₄) |
| CH₂(2Cl—C₆H₄) | CH₂CH₂CH₂CF₂CH₃ | CH₂S(2Cl—C₆H₄) |
| CH₂(4Cl—C₆H₄) | CH₂-cyclopropyl | CH₂S(4CH₃—C₆H₄) |
| CH₂(2,4Cl—C₆H₃) | CH₂-cyclobutyl | CH₂S(2,4Cl—C₆H₃) |
| CH₂(3SCH₃—C₆H₄) | CH₂-cyclopentyl | CH₂S(3SCH₃—C₆H₄) |
| CH₂(3OCH₃—C₆H₄) | CH₂-cyclopentyl | CH₂S(2,6Cl—C₆H₃) |
| CH₂(3Cl—C₆H₄) | CH₂-cyclohexyl | CH₂S(C₆H₅) |
| CH₂(2,6F—C₆H₃) | cyclopropyl | CH₂S(3CF₃—C₆H₄) |
| CH₂(2,6Cl—C₆H₃) | cyclobutyl | CH₂S(2Cl—C₆H₄) |
| CH₂(3,4F—C₆H₃) | cyclopentyl | CH₂S(4CH₃—C₆H₄) |
| | cyclohexyl | CH₂S(2,6Cl—C₆H₃) |
| R¹ = Br, R² = C≡N | CH₂OCH₂CH₃ | CH₂S(2,4Cl—C₆H₃) |
| R³ | CH₂OCH₂CH₂CH₃ | CH₂S(2Cl—C₆H₃) |
| (CH₂)₂CH₃ | CH₂OCH₂CH(CH₃)₂ | CH₂NHCH₂CH₃ |
| R³ | CH₂OCH₂(C₆H₅) | CH₂NHCH₂CH₂CH₃ |
| | R³ | R³ |
| CH₂NHCH₂C(C₆H₅) | S(C₆H₅) | CH₂CH₂CO₂CH₃ |
| CH₂NHCH₂CH(CH₃)₂ | S(3CF₃—C₆H₄) | CH₂CH₂OCH₂CH₃ |
| CH₂NHCH(3CF₃—C₆H₄) | S(2Cl—C₆H₄) | CH₂CH₂SCH₂CH₃ |
| CH₂NHCH(2Cl—C₆H₄) | S(4OCH₃—C₆H₄) | CH₂CH₂—NHCH₂CH₃ |
| CH₂NH(C₆H₅) | S(2,4Cl—C₆H₃) | CH₂CH₂N(CH₃)CH₂CH₃ |
| CH₂NH(2Cl—C₆H₄) | S(2,6F—C₆H₃) | CH=CH(CH₃)₂ |

-continued

| | |
|---|---|
| CH₂N(CH₃)(2Cl—C₆H₄) | 2(3CH₃—C₆H₄) | 
| OCH₂CH₂CH₃ | NHCH₂CH₂CH₃ |
| OCH₂(CH₂)₂CH₃ | NHCH₂(CH₂)₂CH₃ |
| OCH₂(CH₂)₃CH₃ | NHCH₂(CH₂)₄CH₃ |
| OCH₂(CH₂)₅CH₃ | NHCH₂(CH₂)₅CH₃ |
| OCH₂C(C₆H₅) | NHCH₂CH(CH₃)₂ |
| OCH₂(3CF₃—C₆H₄) | NHCH₂C₆H₅ |
| OCH₂(2Cl—C₆H₄) | NHCH₂(3CF₃—C₆H₄) |
| OCH₂CH(CH₃) | NHCH₂(2Cl—C₆H₄) |
| O(C₆H₅) | NHCH₂(4CH₃—C₆H₄) |
| O(3CF₃—C₆H₄) | NHCH₂(2,4Cl—C₆H₃) |
| O(2Cl—C₆H₄) | NHCH₂(2,6Cl—C₆H₃) |
| O(4SCH₃—C₆H₄) | NH(C₆H₅) |
| O(2,4Cl—C₆H₃) | NH(3CF₃—C₆H₄) |
| SCH₃ | NH(2Cl—C₆H₄) |
| SCH₂(CH₂)₂CH₃ | NH(3CH₃—C₆H₄) |
| SCH₂(CH₂)₃CH₃ | NH(2,4Cl—C₆H₃) |
| SCH₂(CH₂)₅CH₃ | NH(2,6Cl—C₆H₃) |
| SCH₂(C₆H₅) | N(CH₃)(3CF₃—C₆H₄) |
| SCH₂(3SCH₃—C₆H₄) | N(CH₃)CH₂CH₂CH₃ |
| SCH₂(2OCH₃—C₆H₄) | N(CH₂)₄ |
| SCH₂(2Cl—C₆H₄) | N(CH₂)₅ |
| SCH₂(2,4-C₆H₃) | N(CH₂)₆ |
| SCH₂(4CF₃—C₆H₄) | N(CH₂CH₂—OCH₂CH₂)₂ |
| S(CH₃)₃ | CH₂CO₂CH₃ |
| SCH₂CH(CH₃)₂ | CH₂CH₂CO₂CH₂CH₃ |
| R¹ = I, R² = C≡N | R³ |
| R³ | CH₂OCH₂CH(CH₃)₂ |
| (CH₂)₂CH₃ | CH₂OCH₂(C₆H₅) |
| (CH₂)₃CH₃ | CH₂OCH₂(3CF₃—C₆H₄) |
| (CH₂)₄CH₃ | CH₂OCH₂(2Cl—C₆H₄) |
| (CH₂)₅CH₃ | CH₂OCH₂(3SCH₃—C₆H₄) |
| (CH₂)₆CH₃ | CH₂OCH₂(4Cl—C₆H₄) |
| (CH₂)₇CH₃ | CH₂OCH₂(2,4F—C₆H₃) |
| (CH₂)₈CH₃ | CH₂OCH₂OCH₂CH₂CH₃ |
| (CH₂)₉CH₃ | CH₂O(C₆H₅) |
| CH₂CH(CH₃)₂ | CH₂O(3CF₃—C₆H₄) |
| CH₂CH₂CH(CH₃)₂ | CH₂O(4CF₃—C₆H₄) |
| CH₂CH₂CH₂CH(CH₃)₂ | CH₂O(2Cl—C₆H₄) |
| CH₂CH₂CH₂CH₂CH₂CH₃ | CH₂O(3SCH₃—C₆H₄) |
| CH₂CH(CH₃)CH₂CH₂CH₃ | CH₂O(2Cl—C₆H₄) |
| CH₂CH(CH₃)CH₂OCH₃ | CH₂O(4Cl—C₆H₄) |
| CH₂CH₂CH₂OCH₃ | CH₂O(2,4Cl—C₆H₃) |
| CH₂CH₂CH₂—S—CH₂CH₃ | CH₂SCH₂CH₂CH₃ |
| CH₂CH₂CH₂SCH₃ | CH₂SCH₂CH(CH₃)₂ |
| CH₂CH₂CH₂NHCH₂CH₃ | CH₂SCH₂(C₆H₅) |
| CH₂CF₂CH(CH₃)₂ | CH₂SCH₂(3CF₃—C₆H₄) |
| CH₂CF₂CH₂CF₂CH₃ | CH₂S(2Cl—C₆H₄) |
| CH₂-cyclopropyl | CH₂S(4CH₃—C₆H₄) |
| CH₂-cyclobutyl | CH₂S(2,4Cl—C₆H₃) |
| CH₂-cyclopentyl | CH₂S(3SCH₃—C₆H₄) |
| CH₂-cyclohexyl | CH₂S(2,6Cl—C₆H₃) |
| CH₂CH₂CH=CH₂ | |
| CH₂CH=CH—CH₃ | |
| CH=CH—CH₂CH₂—Cl | |
| CH₂CH₂CH—ClCH₂—Cl | |
| C₆H₅ | |
| 3CF₃—C₆H₄ | |
| 2Cl—C₆H₄ | |
| 3CH₃—C₆H₄ | |
| 3OCH₃—C₆H₄ | |
| 2CF₃—C₆H₄ | |
| 2,4Cl—C₆H₃ | |
| 2,6Cl—C₆H₃ | |
| 2SCH₃—C₆H₄ | |
| CH₂(C₆H₅) | |
| CH₂(3CF₃—C₆H₄) | |
| CH₂(2Cl—C₆H₄) | |
| CH₂(4Cl—C₆H₄) | |
| CH₂(2,4Cl—C₆H₃) | |
| CH₂(3SCH₃—C₆H₄) | |
| CH₂(3OCH₃—C₆H₄) | |
| CH₂(3Cl—C₆H₄) | |
| CH₂(2,6F—C₆H₃) | |
| CH₂(2,6Cl—C₆H₃) | |
| CH₂(3,4F—C₆H₃) | |
| R³ | |
| CH₂NHCH₂CH₃ | |
| CH₂NHCH₂CH₂CH₃ | |
| CH₂NHCH₂C(C₆H₅) | |
| CH₂NHCH₂CH(CH₃)₂ | |
| CH₂NHCH₂(3CF₃—C₆H₄) | |
| CH₂NHCH₂(2Cl—C₆H₄) | |
| CH₂NH(C₆H₅) | |
| CH₂NH(2Cl—C₆H₄) | |
| CH₂N(CH₃)(2Cl—C₆H₄) | |
| OCH₂CH₂CH₃ | |
| OCH₂(CH₂)₂CH₃ | |
| OCH₂(CH₂)₃CH₃ | |
| OCH₂(CH₂)₅CH₃ | |
| OCH₂C(C₆H₅) | |
| OCH₂(3CF₃—C₆H₄) | |
| OCH₂(2Cl—C₆H₄) | |
| OCH₂CH(CH₃)₂ | |
| O(C₆H₅) | |
| O(3CF₃—C₆H₄) | |
| O(2Cl—C₆H₄) | |
| O(4SCH₃—C₆H₄) | |
| O(2,4Cl—C₆H₃) | |
| SCH₂CH₂CH₃ | |
| SCH₂(CH₂)₂CH₃ | |
| SCH₂(CH₂)₃CH₃ | |
| SCH₂(CH₂)₅CH₃ | |

| | | |
|---|---|---|
| cyclopropyl | CH$_2$S(C$_6$H$_5$) | SCH$_2$(C$_6$H$_5$) |
| cyclobutyl | CH$_2$S(3CF$_3$—C$_6$H$_4$) | SCH$_2$(3SCH$_3$—C$_6$H$_4$) |
| cyclopentyl | CH$_2$S(2Cl—C$_6$H$_4$) | SCH$_2$(2OCH$_3$—C$_6$H$_4$) |
| cyclohexyl | CH$_2$S(4CH$_3$—C$_6$H$_4$) | SCH$_2$(2Cl—C$_6$H$_4$) |
| CH$_2$OCH$_2$CH$_3$ | CH$_2$S(2,6Cl—C$_6$H$_3$) | SCH$_2$(2,4-C$_6$H$_3$) |
| CH$_2$OCH$_2$CH$_2$CH$_3$ | CH$_2$S(2,4Cl—C$_6$H$_3$) | SCH$_2$(4CF$_3$—C$_6$H$_4$) |
| R$^3$ | R$^3$ | R$^1$ = OCH$_3$, R$^2$ = C≡N |
| S(CH$_3$)$_3$ | CH$_2$CO$_2$CH$_3$ | R$^3$ |
| SCH$_2$CH(CH$_3$)$_2$ | CH$_2$CH$_2$CO$_2$CH$_2$CH$_3$ | (CH$_2$)$_2$CH$_3$ |
| S(C$_6$H$_5$) | CH$_2$CH$_2$CO$_2$CH$_3$ | (CH$_2$)$_3$CH$_3$ |
| S(3CF$_3$—C$_6$H$_4$) | CH$_2$CH$_2$OCH$_2$CH$_3$ | (CH$_2$)$_4$CH$_3$ |
| S(2Cl—C$_6$H$_4$) | CH$_2$CH$_2$SCH$_2$CH$_3$ | (CH$_2$)$_5$CH$_3$ |
| S(4OCH$_3$—C$_6$H$_4$) | CH$_2$CH$_2$—NHCH$_2$CH$_3$ | (CH$_2$)$_6$CH$_3$ |
| S(2,4Cl—C$_6$H$_3$) | CH$_2$CH$_2$N(CH$_3$)CH$_2$CH$_3$ | (CH$_2$)$_7$CH$_3$ |
| S(2,6F—C$_6$H$_3$) | CH═CH(CH$_3$)$_2$ | (CH$_2$)$_8$CH$_3$ |
| 2(3CH$_3$—C$_6$H$_4$) | CH$_2$CH$_2$CH═CH$_2$ | (CH$_2$)$_9$CH$_3$ |
| NHCH$_2$CH$_2$CH$_3$ | CH═CH—CH═CH—CH$_3$ | CH$_2$CH(CH$_3$)$_2$ |
| NHCH$_2$(CH$_2$)$_2$CH$_3$ | CH═CH—CH$_2$CH$_2$—Cl | CH$_2$CH$_2$CH(CH$_3$) |
| NHCH$_2$(CH$_2$)$_4$CH$_3$ | CH$_2$CH$_2$CH—ClCH$_2$—Cl | CH$_2$CH$_2$CH(CH$_3$)CH$_2$CH$_2$CH$_3$ |
| NHCH$_2$(CH$_2$)$_5$CH$_3$ | C$_6$H$_5$ | CH$_2$CH(CH$_3$)CH$_2$CH$_2$CH$_3$ |
| NHCH$_2$CH(CH$_3$)$_2$ | 3CF$_3$—C$_6$H$_4$ | CH$_2$CH(CH$_3$)CH$_2$CH$_2$CH$_3$ |
| NHCH$_2$(C$_6$H$_5$) | 2Cl—C$_6$H$_4$ | CH$_2$CH(CH$_2$CH$_3$)CH$_2$CH$_3$ |
| NHCH$_2$(3CF$_3$—C$_6$H$_4$) | 3CH$_3$—C$_6$H$_4$ | CH$_2$CH$_2$CH$_2$OCH$_3$ |
| NHCH$_2$(2Cl—C$_6$H$_4$) | 3OCH$_3$—C$_6$H$_4$ | CH$_2$CH(CH$_2$CH$_3$)OCH$_2$CH$_3$ |
| NHCH$_2$(4CH$_3$—C$_6$H$_4$) | 2CF$_3$—C$_6$H$_4$ | CH$_2$CH$_2$CH$_2$OCH$_3$ |
| NHCH$_2$(2,4Cl—C$_6$H$_3$) | 2,4Cl—C$_6$H$_3$ | CH$_2$CH$_2$—S—CH$_2$CH$_3$ |
| NHCH$_2$(2,6Cl—C$_6$H$_3$) | 2,6Cl—C$_6$H$_3$ | CH$_2$CH$_2$CH$_2$SCH$_3$ |
| NH(C$_6$H$_5$) | 2SCH$_3$—C$_6$H$_4$ | CH$_2$CH$_2$NHCH$_2$CH$_3$ |
| NH(3CF$_3$—C$_6$H$_4$) | CH$_2$(C$_6$H$_5$) | CH$_2$CF$_2$CH$_2$CF$_3$ |
| NH(2Cl—C$_6$H$_4$) | CH$_2$(3CF$_3$—C$_6$H$_4$) | CH$_2$CH$_2$CH$_2$CF$_3$ |
| NH(3CH$_3$—C$_6$H$_4$) | CH$_2$(2Cl—C$_6$H$_4$) | CH$_2$-cyclopropyl |
| NH(2,4Cl—C$_6$H$_3$) | CH$_2$(4Cl—C$_6$H$_3$) | CH$_2$-cyclobutyl |
| NH(2,6Cl—C$_6$H$_3$) | CH$_2$(2,4Cl—C$_6$H$_4$) | CH$_2$-cyclopentyl |
| N(CH$_3$)(3CF$_3$—C$_6$H$_4$) | CH$_2$(3SCH$_3$—C$_6$H$_4$) | CH$_2$-cyclohexyl |
| N(CH$_3$)CH$_2$CH$_2$CH$_3$ | CH$_2$(3OCH$_3$—C$_6$H$_4$) | cyclopropyl |
| N(CH$_2$)$_4$ | CH$_2$(3Cl—C$_6$H$_4$) | cyclobutyl |
| N(CH$_2$)$_5$ | CH$_2$(2,6F—C$_6$H$_4$) | cyclopentyl |
| N(CH$_2$)$_6$ | CH$_2$(2,6Cl—C$_6$H$_3$) | cyclohexyl |
| N(CH$_2$CH$_2$—OCH$_2$CH$_2$)$_2$ | CH$_2$(3,4F—C$_6$H$_3$) | CH$_2$OCH$_2$CH$_3$ |
| CH$_2$OCH$_2$CH(CH$_3$)$_2$ | OCH$_2$CH$_2$CH$_3$ | CH$_2$OCH$_2$CH$_2$CH$_3$ |
| CH$_2$OCH$_2$C(C$_6$H$_5$) | CH$_2$NHCH$_2$CH$_3$ | R$^3$ |
| CH$_2$OCH$_2$(3CF$_3$—C$_6$H$_4$) | CH$_2$NHCH$_2$CH$_2$CH$_3$ | S(CH$_3$)$_3$ |
| CH$_2$OCH$_2$(2CF$_3$—C$_6$H$_4$) | CH$_2$NHCH$_2$C(C$_6$H$_5$) | SCH$_2$CH(CH$_3$)$_2$ |
| CH$_2$OCH$_2$(3SCH$_3$—C$_6$H$_4$) | CH$_2$NHCH$_2$CH(CH$_3$)$_2$ | S(C$_6$H$_5$) |
| CH$_2$OCH$_2$(3CF$_3$—C$_6$H$_4$) | CH$_2$NHCH$_2$(3CF$_3$—C$_6$H$_4$) | S(3CF$_3$—C$_6$H$_4$) |
| CH$_2$OCH$_2$(2,4F—C$_6$H$_4$) | CH$_2$NHCH$_2$(2Cl—C$_6$H$_4$) | S(2Cl—C$_6$H$_4$) |
| CH$_2$OCH$_2$(2,4F—C$_6$H$_3$) | CH$_2$NH(C$_6$H$_5$) | S(4OCH$_3$—C$_6$H$_4$) |
| CH$_2$OCH$_2$(2,6F—C$_6$H$_3$) | CH$_2$NH(2Cl—C$_6$H$_4$) | S(2,4Cl—C$_6$H$_3$) |
| CH$_2$O(C$_6$H$_5$) | CH$_2$N(CH$_3$)(2Cl—C$_6$H$_4$) | S(2,6F—C$_6$H$_3$) |
| CH$_2$O(3CF$_3$—C$_6$H$_4$) | OCH$_2$CH$_2$CH$_3$ | 2(3CH$_3$—C$_6$H$_4$) |
| CH$_2$O(4CF$_3$—C$_6$H$_4$) | OCH$_2$(CH$_2$)$_2$CH$_3$ | NHCH$_2$CH$_2$CH$_3$ |
| CH$_2$O(2Cl—C$_6$H$_4$) | OCH$_2$(CH$_2$)$_3$CH$_3$ | NHCH$_2$(CH$_2$)$_2$CH$_3$ |
| CH$_2$O(3SCH$_3$—C$_6$H$_4$) | OCH$_2$(CH$_2$)$_5$CH$_3$ | NHCH$_2$(CH$_2$)$_4$CH$_3$ |
| | | NHCH$_2$(CH$_2$)$_5$CH$_3$ |

-continued

| | |
|---|---|
| CH₂O(2CH₃—C₆H₄) | NHCH₂CH(CH₃)₂ |
| CH₂O(4Cl—C₆H₄) | NHCH₂(C₆H₅) |
| CH₂O(2,4Cl—C₆H₃) | NHCH₂(3CF₃—C₆H₄) |
| CH₂SCH₂CH₃ | NHCH₂(2Cl—C₆H₄) |
| CH₂SCH₂CH₂CH₃ | NHCH₂(4CH₃—C₆H₄) |
| CH₂SCH₂CH(CH₃)₂ | NHCH₂(2,4Cl—C₆H₃) |
| CH₂SCH₂(C₆H₅) | NHCH₂(2,6Cl—C₆H₃) |
| CH₂SCH₂(3CF₃—C₆H₄) | NH(C₆H₅) |
| CH₂S(2Cl—C₆H₄) | NH(3CF₃—C₆H₄) |
| CH₂S(2,4Cl—C₆H₃) | NH(2Cl—C₆H₄) |
| CH₂S(4CH₃—C₆H₄) | NH(3CH₃—C₆H₄) |
| CH₂S(3SCH₃—C₆H₄) | NH(2,4Cl—C₆H₃) |
| CH₂S(2,6Cl—C₆H₃) | NH(2,6Cl—C₆H₃) |
| CH₂S(C₆H₅) | N(CH₃)(3CF₃—C₆H₄) |
| CH₂S(3SCH₃—C₆H₄) | N(CH₃)CH₂CH₂CH₃ |
| CH₂S(2OCH₃—C₆H₄) | N(CH₂)₄ |
| CH₂S(2Cl—C₆H₄) | N(CH₂)₅ |
| CH₂S(4CH₃—C₆H₃) | N(CH₂)₆ |
| CH₂S(2,6Cl—C₆H₃) | N(CH₂CH₂—OCH₂CH₂)₂ |
| CH₂S(2,4-C₆H₃) | R³ |
| CH₂S(4CF₃—C₆H₄) | |
| R¹ = OCF₃, R² = C≡N | |
| R³ | CH₂OCH₂CH(CH₃)₂ |
| CH₂CO₂CH₃ | CH₂OCH₂(C₆H₅) |
| CH₂CH₂CO₂CH₂CH₃ | CH₂OCH₂(3CF₃—C₆H₄) |
| (CH₂)₂CH₃ | CH₂OCH₂(2Cl—C₆H₄) |
| (CH₂)₃CH₃ | CH₂OCH₂(3SCH₃—C₆H₄) |
| (CH₂)₄CH₃ | CH₂OCH₂(4Cl—C₆H₄) |
| (CH₂)₅CH₃ | CH₂OCH₂(2,4F—C₆H₄) |
| (CH₂)₆CH₃ | CH₂CH₂OCH₂CH₂CH₃ |
| (CH₂)₇CH₃ | CH₂O(C₆H₅) |
| (CH₂)₈CH₃ | CH₂O(3CF₃—C₆H₄) |
| (CH₂)₉CH₃ | CH₂O(4CF₃—C₆H₄) |
| CH₂CH(CH₃)₂ | CH₂O(2Cl—C₆H₄) |
| CH₂CH₂CH(CH₃)₂ | CH₂O(3SCH₃—C₆H₄) |
| CH₂CH₂CH(CH₃)CH(CH₃)₂ | CH₂O(4Cl—C₆H₄) |
| CH₂CH₂CH(CH₃)CH₂CH₂CH₃ | CH₂O(2,4Cl—C₆H₃) |
| CH₂CH(CH₃)CH₂CH₂CH₂CH₃ | CH₂SCH₂CH₃ |
| CH₂CH₂CH₂CH₂OCH₂CH₃ | CH₂SCH₂CH₂CH₃ |
| CH₂CH₂CH₂OCH₂CH₃ | CH₂SCH₂CH(CH₃)₂ |
| CH₂CH₂CH₂—S—CH₂CH₃ | CH₂SCH₂(C₆H₅) |
| CH₂CH₂CH₂CH₂SCH₃ | CH₂S(3CF₃—C₆H₄) |
| CH₂CH₂CH₂NHCH₂CH₃ | CH₂S(2Cl—C₆H₄) |
| CH₂CF₂CH(CH₃)₂ | CH₂S(4CH₃—C₆H₄) |
| CH₂CH₂CF₂CF₂CH₃ | CH₂S(4Cl—C₆H₄) |
| CH₂-cyclopropyl | CH₂S(3SCH₃—C₆H₄) |
| CH₂-cyclobutyl | CH₂S(2,6Cl—C₆H₃) |
| CH₂-cyclopentyl | CH₂S(C₆H₅) |
| CH₂-cyclohexyl | CH₂S(3CF₃—C₆H₄) |
| cyclopropyl | CH₂S(2Cl—C₆H₄) |
| cyclobutyl | CH₂S(4CH₃—C₆H₃) |
| cyclopentyl | CH₂S(2,6Cl—C₆H₃) |
| cyclohexyl | CH₂S(2,4Cl—C₆H₃) |
| CH₂OCH₂CH₃ | R³ |
| CH₂OCH₂CH₂CH₃ | |

3CF₃—C₆H₄
2Cl—C₆H₄
3CH₃—C₆H₄
3OCH₃—C₆H₄
2CF₃—C₆H₄
2,4Cl—C₆H₃
2,6Cl—C₆H₃
2SCH₃—C₆H₄
CH₂(C₆H₅)
CH₂(3CF₃—C₆H₄)
CH₂(2Cl—C₆H₄)
CH₂(4Cl—C₆H₄)
CH₂(2,4Cl—C₆H₃)
CH₂(3SCH₃—C₆H₄)
CH₂(3OCH₃—C₆H₄)
CH₂(3Cl—C₆H₄)
CH₂(2,6F—C₆H₃)
CH₂(2,6Cl—C₆H₃)
CH₂(3,4F—C₆H₃)
R³

CH=CH—CH₃
CH=CH—CH₂—Cl
CH₂CH₂CH—ClCH₂—Cl
C₆H₅

CH=CH=CH₂
CH₂CH₂CH=CH₂

-continued

| | | |
|---|---|---|
| CH$_2$NHCH$_2$CH$_3$ | S(CH$_3$)$_3$ | CH$_2$CO$_2$CH$_3$ |
| CH$_2$NHCH$_2$CH$_2$CH$_3$ | SCH$_2$CH(CH$_3$)$_2$ | CH$_2$CH$_2$CO$_2$CH$_2$CH$_3$ |
| CH$_2$NHCH$_2$C(CH$_3$) | S(C$_6$H$_5$) | CH$_2$CH$_2$CO$_2$CH$_3$ |
| CH$_2$NHCH$_2$CH(CH$_3$)$_2$ | S(3CF$_3$—C$_6$H$_4$) | CH$_2$CH$_2$OCH$_2$CH$_3$ |
| CH$_2$NHCH$_2$(3CF$_3$—C$_6$H$_4$) | S(2Cl—C$_6$H$_4$) | CH$_2$CH$_2$SCH$_2$CH$_3$ |
| CH$_2$NHCH$_2$(2Cl—C$_6$H$_4$) | S(4OCH$_3$—C$_6$H$_4$) | CH$_2$CH$_2$—NHCH$_2$CH$_3$ |
| CH$_2$NH(C$_6$H$_5$) | S(2,4Cl—C$_6$H$_3$) | CH$_2$CH$_2$N(CH$_3$)CH$_2$CH$_3$ |
| CH$_2$N(CH$_3$)(2Cl—C$_6$H$_4$) | S(2,6F—C$_6$H$_3$) | CH=CH(CH$_3$)$_2$ |
| CH$_2$N(CH$_3$)(2Cl—C$_6$H$_4$) | 2(3CH$_3$—C$_6$H$_4$) | CH$_2$CH=CH=CH$_2$ |
| OCH$_2$CH$_2$CH$_3$ | NHCH$_2$CH$_2$CH$_3$ | CH$_2$CH=CH—CH$_3$ |
| OCH$_2$(CH$_2$)$_2$CH$_3$ | NHCH$_2$(CH$_2$)$_2$CH$_3$ | CH=CH—CH$_2$CH$_2$—Cl |
| OCH$_2$(CH$_2$)$_3$CH$_3$ | NHCH$_2$(CH$_2$)$_4$CH$_3$ | CH$_2$CH$_2$CH—ClCH$_2$—Cl |
| OCH$_2$(CH$_2$)$_5$CH$_3$ | NHCH$_2$(CH$_2$)$_5$CH$_3$ | C$_6$H$_5$ |
| OCH$_2$C(C$_6$H$_5$) | NHCH$_2$CH(CH$_3$)$_2$ | 3CF$_3$—C$_6$H$_4$ |
| OCH$_2$(3CF$_3$—C$_6$H$_4$) | NHCH(C$_6$H$_5$) | 2Cl—C$_6$H$_4$ |
| OCH$_2$(2Cl—C$_6$H$_4$) | NHCH$_2$(3CF$_3$—C$_6$H$_4$) | 3CH$_3$—C$_6$H$_4$ |
| O(C$_6$H$_5$) | NHCH$_2$(2Cl—C$_6$H$_4$) | 3OCH$_3$—C$_6$H$_4$ |
| O(3CF$_3$—C$_6$H$_4$) | NHCH$_2$(4CH$_3$—C$_6$H$_4$) | 2CF$_3$—C$_6$H$_4$ |
| O(2Cl—C$_6$H$_4$) | NHCH$_2$(2,4Cl—C$_6$H$_3$) | 2,4Cl—C$_6$H$_3$ |
| O(4SCH$_3$—C$_6$H$_4$) | NHCH$_2$(2,6Cl—C$_6$H$_3$) | 2,6Cl—C$_6$H$_3$ |
| O(2,4Cl—C$_6$H$_3$) | NH(C$_6$H$_5$) | 2SCH$_3$—C$_6$H$_4$ |
| SCH$_2$CH$_2$CH$_3$ | NH(3CF$_3$—C$_6$H$_4$) | NH(C$_6$H$_5$) |
| SCH$_2$(CH$_2$)$_2$CH$_3$ | NH(2Cl—C$_6$H$_4$) | CH$_2$(3CF$_3$—C$_6$H$_4$) |
| SCH$_2$(CH$_2$)$_3$CH$_3$ | NH(3CH$_3$—C$_6$H$_4$) | CH$_2$(2Cl—C$_6$H$_4$) |
| SCH$_2$(CH$_2$)$_5$CH$_3$ | NH(2,4Cl—C$_6$H$_3$) | CH$_2$(4Cl—C$_6$H$_4$) |
| SCH$_2$(C$_6$H$_5$) | NH(2,6Cl—C$_6$H$_3$) | CH$_2$(2,4Cl—C$_6$H$_3$) |
| SCH$_2$(3SCH$_3$—C$_6$H$_4$) | N(CH$_3$)(3CF$_3$—C$_6$H$_4$) | CH$_2$(3SCH$_3$—C$_6$H$_4$) |
| SCH$_2$(2OCH$_3$—C$_6$H$_4$) | N(CH$_3$)CH$_2$CH$_2$CH$_3$ | CH$_2$(3OCH$_3$—C$_6$H$_4$) |
| SCH$_2$(2Cl—C$_6$H$_4$) | N(CH$_2$)$_4$ | CH$_2$(3Cl—C$_6$H$_4$) |
| SCH$_2$(2,4-C$_6$H$_3$) | N(CH$_2$)$_5$ | CH$_2$[2,6F—C$_6$H$_3$] |
| R$^1$ = OCF$_2$H, R$^2$ = C≡N | N(CH$_2$)$_6$ | CH$_2$[2,6Cl—C$_6$H$_3$] |
| R$^3$ | N(CH$_2$CH$_2$—OCH$_2$CH$_2$)$_2$ | CH$_2$[3,4F—C$_6$H$_3$] |
| | R$^3$ | R$^3$ |
| (CH$_2$)$_2$CH$_3$ | CH$_2$OCH$_2$CH(CH$_3$)$_2$ | CH$_2$NHCH$_2$CH$_3$ |
| (CH$_2$)$_3$CH$_3$ | CH$_2$OCH$_2$(C$_6$H$_5$) | CH$_2$NHCH$_2$CH$_2$CH$_3$ |
| (CH$_2$)$_4$CH$_3$ | CH$_2$OCH$_2$(3CF$_3$—C$_6$H$_4$) | CH$_2$NHCH$_2$C(CH$_3$) |
| (CH$_2$)$_5$CH$_3$ | CH$_2$OCH$_2$(2Cl—C$_6$H$_4$) | CH$_2$NHCH$_2$CH(CH$_3$)$_2$ |
| (CH$_2$)$_6$CH$_3$ | CH$_2$OCH$_2$(3SCH$_3$—C$_6$H$_4$) | CH$_2$NHCH$_2$(3CF$_3$—C$_6$H$_4$) |
| (CH$_2$)$_7$CH$_3$ | CH$_2$OCH$_2$(4Cl—C$_6$H$_4$) | CH$_2$NHCH$_2$(2Cl—C$_6$H$_4$) |
| (CH$_2$)$_8$CH$_3$ | CH$_2$OCH$_2$(2,4F—C$_6$H$_3$) | CH$_2$NH(C$_6$H$_5$) |
| (CH$_2$)$_9$CH$_3$ | CH$_2$CH$_2$OCH$_2$CH$_2$CH$_3$ | CH$_2$NH(2Cl—C$_6$H$_4$) |
| CH$_2$CH(CH$_3$)$_2$ | CH$_2$O(C$_6$H$_5$) | CH$_2$N(CH$_3$)(2Cl—C$_6$H$_4$) |
| CH$_2$CH$_2$CH(CH$_3$)$_2$ | CH$_2$O(3CF$_3$—C$_6$H$_4$) | OCH$_2$CH$_2$CH$_3$ |
| CH$_2$CH(CH$_3$)CH(CH$_3$) | CH$_2$O(4CF$_3$—C$_6$H$_4$) | OCH$_2$(CH$_2$)$_2$CH$_3$ |
| CH$_2$CH$_2$CH(CH$_2$)CH$_2$CH$_3$ | CH$_2$O(2Cl—C$_6$H$_4$) | OCH$_2$(CH$_2$)$_3$CH$_3$ |
| CH$_2$CH(CH$_2$CH$_3$)CH$_2$CH$_3$ | CH$_2$O(3SCH$_3$—C$_6$H$_4$) | OCH$_2$(CH$_2$)$_5$CH$_3$ |
| CH$_2$CH(CH$_3$)CH$_2$OCH$_3$ | CH$_2$O(2CH$_3$—C$_6$H$_4$) | OCH$_2$C(C$_6$H$_5$) |
| CH$_2$CH$_2$CH$_2$OCH$_3$ | CH$_2$O(4Cl—C$_6$H$_4$) | OCH$_2$(3CF$_3$—C$_6$H$_4$) |
| CH$_2$CH$_2$CH$_2$OCH$_3$ | CH$_2$O(2,4Cl—C$_6$H$_3$) | OCH$_2$(2Cl—C$_6$H$_4$) |
| CH$_2$CH$_2$CH$_2$—S—CH$_2$CH$_3$ | CH$_2$SCH$_2$CH$_3$ | OCH$_2$CH(CH$_3$)$_2$ |
| CH$_2$CH$_2$CH$_2$SCH$_3$ | CH$_2$SCH$_2$CH$_2$CH$_3$ | O(C$_6$H$_5$) |
| CH$_2$CH$_2$CH$_2$NHCH$_2$CH$_3$ | CH$_2$SCH$_2$CH(CH$_3$)$_2$ | O(3CF$_3$—C$_6$H$_4$) |
| | CH$_2$SCH$_2$[C$_6$H$_5$] | O(2Cl—C$_6$H$_4$) |

-continued

| | | |
|---|---|---|
| CH₂CF₂CH(CH₃)₂ | CH₂SCH₂(3CF₃—C₆H₄) | O(4SCH₃—C₆H₄) |
| CH₂CH₂CH₂CF₂CH₃ | CH₂S(2Cl—C₆H₄) | O(2,4Cl—C₆H₃) |
| CH₂-cyclopropyl | CH₂S(4CH₃—C₆H₃) | SCH₂CH₂CH₃ |
| CH₂-cyclobutyl | CH₂S(2,4Cl—C₆H₃) | SCH₂(CH₂)₂CH₃ |
| CH₂-cyclopentyl | CH₂S(3SCH₃—C₆H₄) | SCH₂(CH₂)₃CH₃ |
| CH₂-cyclohexyl | CH₂S(2,6Cl—C₆H₃) | SCH₂(CH₂)₅CH₃ |
| cyclopropyl | CH₂S(C₆H₅) | SCH₂(C₆H₅) |
| cyclobutyl | CH₂S(3CF₃—C₆H₄) | SCH₂(3SCH₃—C₆H₄) |
| cyclopentyl | CH₂S(2Cl—C₆H₄) | SCH₂(2OCH₃—C₆H₄) |
| cyclohexyl | CH₂S(4CH₃—C₆H₄) | SCH₂(2Cl—C₆H₄) |
| CH₂OCH₂CH₃ | CH₂S(2,6Cl—C₆H₃) | SCH₂,2,4-C₆H₃) |
| CH₂OCH₂CH₂CH₃ | CH₂S(2,4Cl—C₆H₃) | SCH₂(4CF₃—C₆H₄) |
| R³ | R³ | R¹ = Cl, R² = CO₂H |
| S(CH₃)₃ | CH₂CO₂CH₃ | R³ |
| SCH₂CH(CH₃)₂ | CH₂CH₂CO₂CH₂CH₃ | (CH₂)₂CH₃ |
| S(C₆H₅) | CH₂CH₂CO₂CH₃ | (CH₂)₃CH₃ |
| S(3CF₃—C₆H₄) | CH₂CH₂OCH₂CH₃ | (CH₂)₄CH₃ |
| S(2Cl—C₆H₄) | CH₂CH₂SCH₂CH₃ | (CH₂)₅CH₃ |
| S(4OCH₃—C₆H₄) | CH₂CH₂—NHCH₂CH₃ | (CH₂)₆CH₃ |
| S(2,4Cl—C₆H₄) | CH₂CH₂N(CH₃)CH₂CH₃ | (CH₂)₇CH₃ |
| S(2,6F—C₆H₃) | CH═CH(CH₂)₂ | (CH₂)₈CH₃ |
| 2(3CH₃—C₆H₄) | CH₂CH═CH═CH₂ | (CH₂)₉CH₃ |
| NHCH₂CH₃ | CH═CH—CH═CH₂ | CH₂CH(CH₃)₂ |
| NHCH₂(CH₂)₂CH₃ | CH═CH—CH₂CH₂—Cl | CH₂CH₂CH(CH₃)₂ |
| NHCH₂(CH₂)₄CH₃ | CH₂CH₂CH—ClCH₂—Cl | CH₂CH₂CH(CH₃)CH₂CH₂CH₃ |
| NHCH₂(CH₂)₅CH₃ | C₆H₅ | CH₂CH(CH₃)CH₂CH₂CH₃ |
| NHCH₂CH(CH₃)₂ | 3CF₃—C₆H₄ | CH₂CH(CH₃)CH₂CH₂OCH₃ |
| NHCH₂(C₆H₅) | 2Cl—C₆H₄ | CH₂CH(CH₃)CH₂OCH₃ |
| NHCH₂(3CF₃—C₆H₄) | 3CH₃—C₆H₄ | CH₂CH(CH₃)CH₂OCH₂CH₃ |
| NHCH₂(2Cl—C₆H₄) | 3OCH₃—C₆H₄ | CH₂CH(CH₃)CH₂OCH₂OCH₃ |
| NHCH₂(4CH₃—C₆H₄) | 2CF₃—C₆H₄ | CH₂CH₂CH₂—S—CH₂CH₃ |
| NHCH₂(2,4Cl—C₆H₃) | 2,4Cl—C₆H₃ | CH₂CH₂CH₂CH₂SCH₃ |
| NHCH₂(2,6Cl—C₆H₃) | 2,6Cl—C₆H₃ | CH₂CH₂CH₂NHCH₂CH₃ |
| NH(C₆H₅) | 2SCH₃—C₆H₄ | CH₂CF₂CH(CH₃)₂ |
| NH(3CF₃—C₆H₄) | CH₂(C₆H₅) | CH₂CH₂CH₂CF₂CH₃ |
| NH(2Cl—C₆H₄) | CH₂(3CF₃—C₆H₄) | CH₂-cyclopropyl |
| NH(3CH₃—C₆H₄) | CH₂(2Cl—C₆H₄) | CH₂-cyclobutyl |
| NH(2,4Cl—C₆H₃) | CH₂(4Cl—C₆H₄) | CH₂-cyclopentyl |
| NH(2,6Cl—C₆H₃) | CH₂(2,4Cl—C₆H₃) | CH₂-cyclohexyl |
| N(CH₃)(3CF₃—C₆H₄) | CH₂(3SCH₃—C₆H₄) | cyclopropyl |
| N(CH₃)CH₂CH₂CH₃ | CH₂NHCH₂(3CF₃—C₆H₄) | cyclobutyl |
| N(CH₂)₄ | CH₂(3Cl—C₆H₄) | cyclopentyl |
| N(CH₂)₅ | CH₂(2,6F—C₆H₃) | cyclohexyl |
| N(CH₂)₆ | CH₂(2,6Cl—C₆H₃) | CH₂OCH₂CH₃ |
| N(CH₂CH₂—OCH₂CH₂)₂ | CH₂(3,4F—C₆H₃) | CH₂OCH₂CH₂CH₃ |
| R³ | R³ | R³ |
| CH₂OCH₂CH(CH₃)₂ | CH₂NHCH₂CH₃ | S(CH₃)₃ |
| CH₂OCH₂(C₆H₅) | CH₂NHCH₂CH₂CH₃ | SCH₂CH(CH₃)₂ |
| CH₂OCH₂(3CF₃—C₆H₄) | CH₂NHCH₂C(C₆H₅) | S(C₆H₅) |
| CH₂OCH₂(2Cl—C₆H₄) | CH₂NHCH₂CH(CH₃)₂ | S(3CF₃—C₆H₄) |
| CH₂OCH₂(3SCH₃—C₆H₄) | CH₂NHCH₂CH(3CF₃—C₆H₄) | S(2Cl—C₆H₄) |
| CH₂OCH₂(4Cl—C₆H₄) | CH₂NHCH₂(2Cl—C₆H₄) | S(4OCH₃—C₆H₄) |
| CH₂OCH₂(2,4F—C₆H₃) | CH₂NH(C₆H₅) | S(2,4Cl—C₆H₃) |

-continued

| | | |
|---|---|---|
| CH₂CH₂OCH₂CH₂CH₃ | CH₂NH(2Cl—C₆H₄) | S(2,6F—C₆H₃) |
| CH₂O(C₆H₅) | CH₂N(CH₃)(2Cl—C₆H₄) | 2(3CH₃—C₆H₄) |
| CH₂O(3CF₃—C₆H₄) | OCH₂CH₂CH₃ | NHCH₂CH₂CH₃ |
| CH₂O(4CF₃—C₆H₄) | OCH₂(CH₂)₂CH₃ | NHCH₂(CH₂)₂CH₃ |
| CH₂O(2Cl—C₆H₄) | OCH₂(CH₂)₃CH₃ | NHCH₂(CH₂)₄CH₃ |
| CH₂O(3SCH₃—C₆H₄) | OCH₂(CH₂)₅CH₃ | NHCH₂(CH₂)₅CH₃ |
| CH₂O(2Cl(C₆H₄) | OCH₂C(C₆H₅) | NHCH₂CH(CH₃)₂ |
| CH₂O(4Cl—C₆H₄) | OCH₂(3CF₃—C₆H₄) | NHCH₂(C₆H₅) |
| CH₂O(2,4Cl—C₆H₃) | OCH₂(2Cl—C₆H₄) | NHCH₂(3CF₃—C₆H₄) |
| CH₂SCH₂CH₂CH₃ | OCH₂CH(CH₃)₂ | NHCH₂(4CH₃—C₆H₄) |
| CH₂SCH₂CH₂CH₃ | O(C₆H₅) | NHCH₂(2,4Cl—C₆H₃) |
| CH₂SCH₂CH(CH₃)₂ | O(3CF₃—C₆H₄) | NHCH₂(2,6Cl—C₆H₃) |
| CH₂SCH₂(C₆H₅) | O(2Cl—C₆H₄) | NH(C₆H₅) |
| CH₂SCH₂(3CF₃—C₆H₄) | O(4SCH₃—C₆H₄) | NH(3CF₃—C₆H₄) |
| CH₂S(2Cl—C₆H₄) | O(2,4Cl—C₆H₃) | NH(2Cl—C₆H₄) |
| CH₂S(4CH₃—C₆H₄) | SCH₂CH₂CH₃ | NH(3CH₃—C₆H₄) |
| CH₂S(2,4Cl—C₆H₃) | SCH₂(CH₂)₂CH₃ | NH(2,4Cl—C₆H₃) |
| CH₂S(3SCH₃—C₆H₄) | SCH₂(CH₂)₃CH₃ | NH(2,6Cl—C₆H₃) |
| CH₂S(2,6Cl—C₆H₃) | SCH₂(CH₂)₅CH₃ | N(CH₃)(3CF₃—C₆H₄) |
| CH₂S(C₆H₅) | SCH₂(C₆H₅) | N(CH₃)CH₂CH₂CH₃ |
| CH₂S(3CF₃—C₆H₄) | SCH₂(3SCH₃—C₆H₄) | N(CH₂)₄ |
| CH₂S(2Cl—C₆H₄) | SCH₂(2OCH₃—C₆H₄) | N(CH₂)₅ |
| CH₂S(4Cl—C₆H₄) | SCH₂(2Cl—C₆H₄) | N(CH₂)₆ |
| CH₂S(2,6Cl—C₆H₃) | SCH₂(2,4-C₆H₃) | N(CH₂CH₂—OCH₂CH₂)₂ |
| CH₂S(2,4Cl—C₆H₃) | SCH₂(4CF₃—C₆H₄) | |

| R³ | R¹ = Br, R² = CO₂H R³ | R³ |
|---|---|---|
| CH₂CO₂CH₃ | (CH₂)₂CH₃ | CH₂OCH₂CH(CH₃)₂ |
| CH₂CH₂CO₂CH₃ | (CH₂)₃CH₃ | CH₂OCH₂(C₆H₅) |
| CH₂CH₂OCH₃ | (CH₂)₄CH₃ | CH₂OCH₂(3CF₃—C₆H₄) |
| CH₂CH₂SCH₂CH₃ | (CH₂)₅CH₃ | CH₂OCH₂(2Cl—C₆H₄) |
| CH₂CH₂—NHCH₂CH₃ | (CH₂)₆CH₃ | CH₂OCH₂(3SCH₃—C₆H₄) |
| CH₂CH₂N(CH₃)CH₂CH₃ | (CH₂)₇CH₃ | CH₂OCH₂(4Cl—C₆H₄) |
| CH=CH(CH₃)₂ | (CH₂)₈CH₃ | CH₂OCH₂(2,4F—C₆H₄) |
| CH₂CH₂CH=CH₂ | (CH₂)₉CH₃ | CH₂OCH₂OCH₂CH₂CH₃ |
| CH₂CH=CH—CH₃ | CH₂CH(CH₃)₂ | CH₂O(C₆H₅) |
| CH=CH—CH₂CH₂—Cl | CH₂CH₂CH(CH₃)₂ | CH₂O(3CF₃—C₆H₄) |
| CH₂CH₂CH—ClCH₂—Cl | CH₂CH₂CH(CH₃)₂ | CH₂O(4CF₃—C₆H₄) |
| C₆H₅ | CH₂CH₂CH(CH₃)CH₂CH₂CH₃ | CH₂O(2Cl—C₆H₄) |
| 3CF₃—C₆H₄ | CH₂CH(CH₃)CH₂CH₂CH₃ | CH₂O(3SCH₃—C₆H₄) |
| 2Cl—C₆H₄ | CH₂CH(CH₃)CH₂CH₂CH₃ | CH₂O(2CH₃—C₆H₄) |
| 3CH₃—C₆H₄ | CH₂CH(CH₃)CH₂CH₂CH₃ | CH₂O(4Cl—C₆H₄) |
| 3OCH₃—C₆H₄ | CH₂CH₂CH₂OCH₂CH₃ | CH₂O(2,4Cl—C₆H₄) |
| 2CF₃—C₆H₄ | CH₂CH₂CH₂—S—CH₂CH₃ | CH₂SCH₂CH₃ |
| 2,4Cl—C₆H₃ | CH₂CH₂CH₂—S—CH₂CH₃ | CH₂SCH₂CH(CH₃)₂ |
| 2,6Cl—C₆H₃ | CH₂CH₂CH₂CH₂SCH₃ | CH₂SCH₂CH(CH₃)₂ |
| 2SCH₃—C₆H₄ | CH₂CH₂CH₂NHCH₂CH₃ | CH₂SCH₂(C₆H₅) |
| CH₂(C₆H₅) | CH₂CF₂CH₂CF₂CH₃ | CH₂S(2CF₃—C₆H₄) |
| CH₂(3CF₃—C₆H₄) | CH₂-cyclopropyl | CH₂S(4CH₃—C₆H₄) |
| CH₂(2Cl—C₆H₄) | CH₂-cyclobutyl | CH₂S(2,4Cl—C₆H₃) |
| CH₂(4Cl—C₆H₄) | CH₂-cyclopentyl | CH₂S(3SCH₃—C₆H₄) |
| CH₂(2,4Cl—C₆H₃) | CH₂-cyclohexyl | CH₂S(2,6Cl—C₆H₃) |
| CH₂(3SCH₃—C₆H₄) | cyclopropyl | CH₂S(C₆H₅) |
| CH₂(3OCH₃—C₆H₄) | cyclobutyl | CH₂S(3CF₃—C₆H₄) |
| CH₂(3Cl—C₆H₄) | cyclopentyl | CH₂S(2Cl—C₆H₄) |
| CH₂(2,6F—C₆H₃) | cyclohexyl | CH₂S(4CH₃—C₆H₄) |
| CH₂(2,6Cl—C₆H₃) | CH₂OCH₂CH₃ | CH₂S(2,6Cl—C₆H₃) |
| CH₂(3,4F—C₆H₃) | CH₂OCH₂CH₂CH₃ | CH₂S(2,4Cl—C₆H₃) |
| R³ | R³ | R³ |
| CH₂NHCH₂CH₃ | S(CH₃)₃ | CH₂CO₂CH₃ |
| CH₂NHCH₂CH₂CH₃ | SCH₂CH(CH₃)₂ | CH₂CH₂CO₂CH₂CH₃ |
| CH₂NHCH₂C(CH₃)₃ | S(C₆H₅) | CH₂CH₂CO₂CH₃ |
| CH₂NHCH₂(CH₃)CH₃ | S(3CF₃—C₆H₄) | CH₂CH₂OCH₂CH₃ |
| CH₂NHCH₂(3CF₃—C₆H₄) | S(2Cl—C₆H₄) | CH₂CH₂SCH₂CH₃ |
| CH₂NHCH₂(2Cl—C₆H₄) | S(4OCH₃—C₆H₄) | CH₂CH₂—NHCH₂CH₃ |
| CH₂NH(C₆H₅) | S(2,4Cl—C₆H₃) | CH₂CH₂N(CH₃)CH₂CH₃ |
| CH₂NH(2Cl—C₆H₄) | S(2,6F—C₆H₃) | CH=CH(CH₃)₂ |
| CH₂N(CH₃)(2Cl—C₆H₄) | 2(3CH₃—C₆H₃) | CH₂CH₂CH=CH₂ |
| OCH₂CH₂CH₃ | NHCH₂(C₆H₅) | CH₂CH=CH—CH₃ |
| OCH₂(CH₂)₂CH₃ | NHCH₂(3CF₃—C₆H₄) | CH=CH—CH₂CH₂—Cl |
| OCH₂(CH₂)₃CH₃ | NHCH₂(2Cl—C₆H₄) | CH₂CH₂CH—ClCH₂—Cl |
| OCH₂(CH₂)₄CH₃ | NHCH₂(CH₂)₃CH₃ | C₆H₅ |
| OCH₂(CH₂)₅CH₃ | NHCH₂CH(CH₃)₂ | 3CF₃—C₆H₄ |
| OCH₂C(C₆H₅) | NHCH₂(C₆H₅) | 2Cl—C₆H₄ |
| OCH₂(3CF₃—C₆H₄) | NHCH₂(3CF₃—C₆H₄) | 3CH₃—C₆H₄ |
| OCH₂(2Cl—C₆H₄) | NHCH₂(2Cl—C₆H₄) | 3OCH₃—C₆H₄ |
| OCH₂CH(CH₃)₂ | NHCH₂(4CH₃—C₆H₃) | 2CF₃—C₆H₄ |
| O(C₆H₅) | NHCH₂(2,4Cl—C₆H₃) | 2,4Cl—C₆H₄ |
| O(3CF₃—C₆H₄) | | |

-continued

| | | |
|---|---|---|
| O(2Cl—C₆H₄) | NHCH₂(2,6Cl—C₆H₃) | 2,6Cl—C₆H₃ |
| O(4SCH₃—C₆H₄) | NH(C₆H₅) | 2SCH₃—C₆H₄ |
| O(2,4Cl—C₆H₃) | NH(3CF₃—C₆H₄) | CH₂(C₆H₅) |
| SCH₂CH₂CH₃ | NH(2Cl—C₆H₄) | CH₂(3CF₃—C₆H₄) |
| SCH₂(CH₂)₂CH₃ | NH(3CH₃—C₆H₄) | CH₂(2Cl—C₆H₄) |
| SCH₂(CH₂)₃CH₃ | NH(2,4Cl—C₆H₃) | CH₂(4Cl—C₆H₄) |
| SCH₂(CH₂)₅CH₃ | NH(2,6Cl—C₆H₃) | CH₂(2,4Cl—C₆H₃) |
| SCH₂(C₆H₅) | N(CH₃)(3CF₃—C₆H₄) | CH₂(3SCH₃—C₆H₄) |
| SCH₂(3SCH₃—C₆H₄) | N(CH₃)CH₂CH₂CH₃ | CH₂(3OCH₃—C₆H₄) |
| SCH₂(2OCH₃—C₆H₄) | N(CH₂)₄ | CH₂(3Cl—C₆H₄) |
| SCH₂(2Cl—C₆H₄) | N(CH₂)₅ | CH₂(2,6F—C₆H₃) |
| SCH₂(2,4-C₆H₃) | N(CH₂)₆ | CH₂(2,6Cl—C₆H₃) |
| SCH₂(4CF₃—C₆H₄) | N(CH₂CH₂—OCH₂CH₂)₂ | CH₂(3,4F—C₆H₃) |
| R¹ = I, R² = CO₂H | R³ | R³ |
| R³ | CH₂OCH₂CH(CH₃)₂ | CH₂NHCH₂CH₃ |
| (CH₂)₂CH₃ | CH₂OCH₂CH₂(C₆H₅) | CH₂NHCH₂CH₂CH₃ |
| (CH₂)₃CH₃ | CH₂OCH₂(3CF₃—C₆H₄) | CH₂NHCH₂C(CH₃)₃ |
| (CH₂)₄CH₃ | CH₂OCH₂(2Cl—C₆H₄) | CH₂NHCH₂CH(CH₃)₂ |
| (CH₂)₅CH₃ | CH₂OCH₂(3SCH₃—C₆H₄) | CH₂NHCH₂(3CF₃—C₆H₄) |
| (CH₂)₆CH₃ | CH₂OCH₂(4Cl—C₆H₄) | CH₂NHCH₂(2Cl—C₆H₄) |
| (CH₂)₇CH₃ | CH₂OCH₂(2,4F—C₆H₃) | CH₂NH(C₆H₅) |
| (CH₂)₈CH₃ | CH₂CH₂OCH₂CH₂CH₃ | CH₂NH(2Cl—C₆H₄) |
| (CH₂)₉CH₃ | CH₂O(C₆H₅) | CH₂N(CH₃)(2Cl—C₆H₄) |
| CH₂CH(CH₃)₂ | CH₂O(3CF₃—C₆H₄) | OCH₂CH₂CH₃ |
| CH₂CH₂CH(CH₃)₂ | CH₂O(4CF₃—C₆H₄) | OCH(CH₂)₂CH₃ |
| CH₂CH₂CH₂CH(CH₃)₂ | CH₂O(2Cl—C₆H₄) | OCH₂(CH₂)₃CH₃ |
| CH₂CH(CH₃)CH₂CH₂CH₃ | CH₂O(3SCH₃—C₆H₄) | OCH₂(CH₂)₅CH₃ |
| CH₂CH(CH₃)CH₂CH₂CH₃ | CH₂O(2CH₃—C₆H₄) | OCH₂C(C₆H₅) |
| CH₂CH(CH(CH₃)₂)CH₂CH₂CH₃ | CH₂O(4Cl—C₆H₄) | OCH₂(3CF₃—C₆H₄) |
| CH₂CH(CH₃)CH₂OCH₃ | CH₂O(2,4Cl—C₆H₃) | OCH₂(2Cl—C₆H₄) |
| CH₂CH₂CH₂OCH₂CH₃ | CH₂SCH₂CH₃ | OCH₂CH(CH₃)₂ |
| CH₂SCH₂CH₂—S—CH₂CH₃ | CH₂SCH₂CH₂CH₃ | O(C₆H₅) |
| CH₂CH₂CH₂NHCH₂CH₃ | CH₂SCH₂CH(CH₃)₂ | O(3CF₃—C₆H₄) |
| CH₂CF₂CH₂CF₂CH₃ | CH₂SCH₂(C₆H₅) | O(2Cl—C₆H₄) |
| CH₂CF₂CH₂CF₂CH₃ | CH₂SCH₂(3CF₃—C₆H₄) | O(4SCH₃—C₆H₄) |
| CH₂-cyclopropyl | CH₂S(2Cl—C₆H₄) | O(2,4Cl—C₆H₃) |
| CH₂-cyclobutyl | CH₂S(4CH₃—C₆H₄) | SCH₂CH₂CH₃ |
| CH₂-cyclopentyl | CH₂S(2,4Cl—C₆H₃) | SCH₂(CH₂)₂CH₃ |
| CH₂-cyclohexyl | CH₂S(3SCH₃—C₆H₄) | SCH₂(CH₂)₃CH₃ |
| cyclopropyl | CH₂S(2,6Cl—C₆H₃) | SCH₂(CH₂)₅CH₃ |
| cyclobutyl | CH₂S(C₆H₅) | SCH₂(C₆H₅) |
| cyclopentyl | CH₂S(3CF₃—C₆H₄) | SCH₂(3SCH₃—C₆H₄) |
| cyclohexyl | CH₂S(2Cl—C₆H₄) | SCH₂(2OCH₃—C₆H₄) |
| CH₂OCH₂CH₃ | CH₂S(4CH₃—C₆H₄) | SCH₂(2Cl—C₆H₄) |
| CH₂OCH₂CH₂CH₃ | CH₂S(2,6Cl—C₆H₃) | SCH₂(2,4-C₆H₃) |
| | CH₂S(2,4Cl—C₆H₃) | SCH₂(4CF₃—C₆H₄) |
| | R³ | R¹ = OCH₃, R² = CO₂H |
| S(CH₃)₃ | CH₂CO₂CH₃ | R³ |
| SCH₂CH(CH₃)₂ | CH₂CH₂CH(CO₂CH₂CH₃ | (CH₂)₂CH₃ |
| S(C₆H₅) | CH₂CH₂CO₂CH₃ | (CH₂)₃CH₃ |
| S(3CF₃—C₆H₄) | CH₂CH₂OCH₂CH₃ | (CH₂)₄CH₃ |
| S(2Cl—C₆H₄) | CH₂CH₂SCH₂CH₃ | (CH₂)₅SCH₃ |
| S(4OCH₃—C₆H₄) | CH₂CH₂—NHCH₂CH₃ | (CH₂)₆CH₃ |

-continued

| | | |
|---|---|---|
| S(2,4Cl—C6H3) | CH2CH2N(CH3)CH2CH3 | (CH2)7CH3 |
| S(2,6F—C6H3) | CH=CH(CH3)2 | (CH2)8CH3 |
| 2(3CH3—C6H4) | CH2CH2CH=CH2 | (CH2)9CH3 |
| NHCH2CH2CH3 | CH2CH=CH—CH3 | CH2CH(CH3)2 |
| NHCH2(CH2)2CH3 | CH=CH—CH2CH2—Cl | CH2CH2CH(CH3)2 |
| NHCH2(CH2)4CH3 | CH2CH2CH—ClCH2—Cl | CH2CH2CH(CH3)CH2 |
| NHCH2(CH2)5CH3 | C6H5 | CH2CH2CH(CH3)CH2CH2CH3 |
| NHCH2CH(CH3)2 | 3CF3—C6H4 | CH2CH(CH3)CH2CH3 |
| NHCH2(C6H5) | 2Cl—C6H4 | CH2CH(CH3)CH2CH3 |
| NHCH2(3CF3—C6H4) | 3CF3—C6H4 | CH2CH2CH2OCH3 |
| NHCH2(2Cl—C6H4) | 3OCH3—C6H4 | CH2CH2CH2OCH3 |
| NHCH2(4CH3—C6H4) | 2CF3—C6H4 | CH2CH2CH2—S—CH2CH3 |
| NHCH2(2,4Cl—C6H3) | 2,4Cl—C6H3 | CH2CH2CH2SCH3 |
| NHCH2(2,6Cl—C6H3) | 2,6Cl—C6H3 | CH2CH2CH2NHCH2CH3 |
| NH(C6H5) | 2SCH3—C6H4 | CH2CF2CH(CH3)2 |
| NH(3CF3—C6H4) | CH2(C6H5) | CH2CH2CH2CF2CH3 |
| NH(2Cl—C6H4) | CH2(3CF3—C6H4) | CH2-cyclopropyl |
| NH(3CH3—C6H4) | CH2(2Cl—C6H4) | CH2-cyclobutyl |
| NH(2,4Cl—C6H3) | CH2(4Cl—C6H4) | CH2-cyclopentyl |
| NH(2,6Cl—C6H3) | CH2(2,4Cl—C6H3) | CH2-cyclohexyl |
| N(CH3)(3CF3—C6H4) | CH2(3SCH3—C6H4) | cyclopropyl |
| N(CH3)CH2CH2CH3 | CH2(3OCH3—C6H4) | cyclobutyl |
| N(CH2)4 | CH2(3Cl—C6H3) | cyclopentyl |
| N(CH2)5 | CH2(2,6F—C6H3) | cyclohexyl |
| N(CH2)6 | CH2(2,6Cl—C6H3) | CH2OCH2CH3 |
| N(CH2CH2—OCH2CH2)2 | CH2(3,4F—C6H3) | CH2OCH2CH2CH3 |
| R3 | R3 | R3 |
| CH2OCH2CH(CH3)2 | CH2NHCH2CH3 | S(CH3)3 |
| CH2OCH2(C6H5) | CH2NHCH2CH2CH3 | SCH2CH(CH3)2 |
| CH2OCH2(3CF3—C6H4) | CH2NHCH2C(C6H5) | S(C6H5) |
| CH2OCH2(2Cl—C6H4) | CH2NHCH2CH(CH3)2 | S(3CF3—C6H4) |
| CH2OCH2(3SCH3—C6H4) | CH2NHCH2(3CF3—C6H4) | S(2Cl—C6H4) |
| CH2OCH2(4Cl—C6H4) | CH2NHCH2(2Cl—C6H4) | S(4OCH3—C6H4) |
| CH2O(C6H5) | CH2NH(C6H5) | S(2,4Cl—C6H3) |
| CH2O(3CF3—C6H4) | CH2NH(2Cl—C6H4) | S(2,6F—C6H3) |
| CH2O(4CF3—C6H4) | CH2NH(2,Cl—C6H4) | 2(3CH3—C6H4) |
| CH2O(3SCH3—C6H4) | CH2N(CH3)(2Cl—C6H4) | NHCH2CH2CH3 |
| CH2O(2CH3—C6H4) | OCH2CH2CH3 | NHCH2(CH2)2CH3 |
| CH2O(4Cl—C6H4) | OCH2(CH2)2CH3 | NHCH2(CH2)4CH3 |
| CH2O(2,4Cl—C6H4) | OCH2(CH2)3CH3 | NHCH2(CH2)5CH3 |
| CH2O(2,6Cl—C6H3) | OCH2(CH2)5CH3 | NHCH2CH(CH3)2 |
| CH2SCH2CH3 | OCH2C(C6H5) | NHCH2(C6H5) |
| CH2SCH2CH2CH3 | O(C6H5) | NHCH2(3CF3—C6H4) |
| CH2SCH2CH(CH3)2 | O(3CF3—C6H4) | NHCH2(2Cl—C6H4) |
| CH2SCH2(C6H5) | O(2Cl—C6H4) | NHCH2(4CH3—C6H4) |
| CH2SCH2(3CF3—C6H4) | O(4SCH3—C6H4) | NHCH2(2,4Cl—C6H3) |
| CH2S(2Cl—C6H4) | O(2,4Cl—C6H3) | NHCH2(2,6Cl—C6H3) |
| CH2S(4CH3—C6H4) | SCH2CH3 | NH(C6H5) |
| CH2S(2,4Cl—C6H3) | SCH2(CH2)2CH3 | NH(3CF3—C6H4) |
| CH2S(3SCH3—C6H4) | SCH2(CH2)3CH3 | NH(2Cl—C6H4) |
| CH2S(3,6Cl—C6H3) | SCH2(CH2)5CH3 | NH(3CH3—C6H4) |
| | | NH(2,4Cl—C6H3) |
| | | NH(2,6Cl—C6H3) |

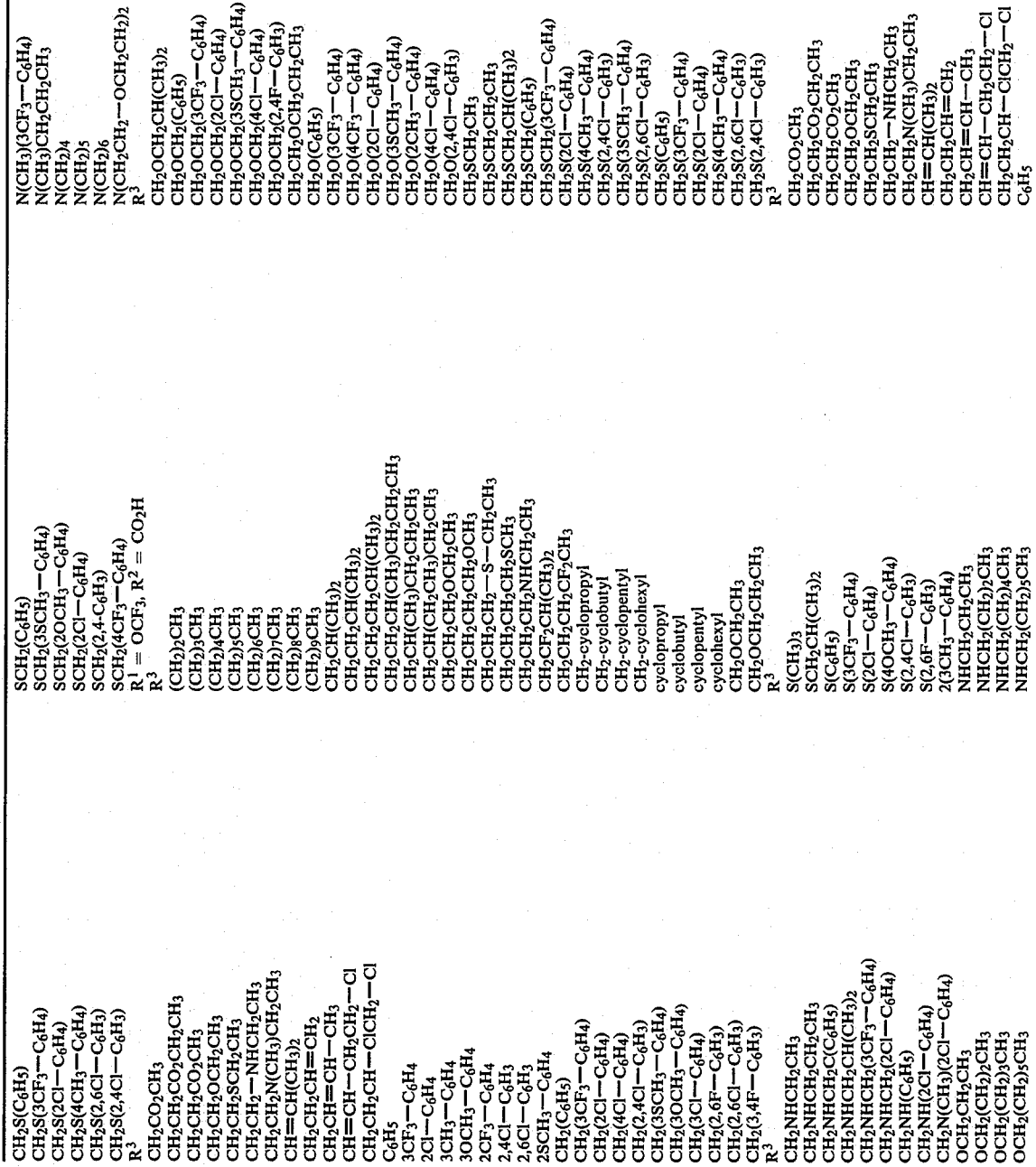

-continued

| | | |
|---|---|---|
| OCH₂C(C₆H₅) | NHCH₂CH(CH₃)₂ | 3CF₃—C₆H₄ |
| OCH₂(3CF₃—C₆H₄) | NHCH₂(C₆H₅) | 2Cl—C₆H₄ |
| OCH₂(2Cl—C₆H₄) | NHCH₂(3CF₃—C₆H₄) | 3CH₃—C₆H₄ |
| OCH₂CH(CH₃)₂ | NHCH₂(2Cl—C₆H₄) | 3OCH₃—C₆H₄ |
| O(C₆H₅) | NHCH₂(4CH₃—C₆H₄) | 2CF₃—C₆H₄ |
| O(3CF₃—C₆H₄) | NHCH₂(2,4Cl—C₆H₃) | 2,4Cl—C₆H₃ |
| O(2Cl—C₆H₄) | NHCH₂(2,6Cl—C₆H₃) | 2,6Cl—C₆H₃ |
| O(4SCH₃—C₆H₄) | NH(C₆H₅) | 2SCH₃—C₆H₄ |
| O(2,4Cl—C₆H₃) | NH(3CF₃—C₆H₄) | CH₂(C₆H₅) |
| SCH₂CH₂CH₃ | NH(2Cl—C₆H₄) | CH₂(3CF₃—C₆H₄) |
| SCH₂(CH₂)₂CH₃ | NH(3CH₃—C₆H₄) | CH₂(2Cl—C₆H₄) |
| SCH₂(CH₂)₃CH₃ | NH(2,4Cl—C₆H₃) | CH₂(4Cl—C₆H₄) |
| SCH₂(CH₂)₅CH₃ | NH(2,6Cl—C₆H₃) | CH₂(2,4Cl—C₆H₃) |
| SCH₂(C₆H₅) | N(CH₃)(3CF₃—C₆H₄) | CH₂(3SCH₃—C₆H₄) |
| SCH₂(3SCH₃—C₆H₄) | N(CH₃)CH₂CH₂CH₃ | CH₂(3OCH₃—C₆H₄) |
| SCH₂(2OCH₃—C₆H₄) | N(CH₂)₄ | CH₂(3Cl—C₆H₄) |
| SCH₂(2Cl—C₆H₄) | N(CH₂)₅ | CH₂(2,6F—C₆H₃) |
| SCH₂(2,4-C₆H₃) | N(CH₂)₆ | CH₂(2,6Cl—C₆H₃) |
| SCH₂(4CF₃—C₆H₄) | N(CH₂CH₂—OCH₂CH₂)₂ | CH₂(3,4F—C₆H₃) |
| R¹ = OCF₂H, R² = CO₂H | R³ | R³ |
| R³ | CH₂OCH₂CH(CH₃)₂ | CH₂NHCH₂CH₃ |
| (CH₂)₃CH₃ | CH₂OCH₂(C₆H₅) | CH₂NHCH₂CH₂CH₃ |
| (CH₂)₄CH₃ | CH₂OCH₂(3CF₃—C₆H₄) | CH₂NHCH₂CH(CH₃)₂ |
| (CH₂)₅CH₃ | CH₂OCH₂(2Cl—C₆H₄) | CH₂NHCH(CH₃)₂ |
| (CH₂)₆CH₃ | CH₂OCH₂(3SCH₃—C₆H₄) | CH₂NHCH₂(3CF₃—C₆H₄) |
| (CH₂)₇CH₃ | CH₂OCH₂(4Cl—C₆H₄) | CH₂NHCH₂(2Cl—C₆H₄) |
| (CH₂)₈CH₃ | CH₂OCH₂(2,4F—C₆H₃) | CH₂NH(C₆H₅) |
| (CH₂)₉CH₃ | CH₂CH₂OCH₂CH₂CH₃ | CH₂NH(2Cl—C₆H₄) |
| CH₂CH(CH₃)₂ | CH₂O(C₆H₅) | CH₂N(CH₃)(2Cl—C₆H₄) |
| CH₂CH₂CH(CH₃)₂ | CH₂O(3CF₃—C₆H₄) | OCH₂CH₂CH₃ |
| CH₂CH₂CH(CH₃)CH(CH₃)₂ | CH₂O(4CF₃—C₆H₄) | OCH₂(CH₂)₂CH₃ |
| CH₂CH(CH₃)CH(CH₃)CH₂CH₃ | CH₂O(2Cl—C₆H₄) | OCH₂(CH₂)₃CH₃ |
| CH₂CH(CH₃)CH₂CH₂CH₂CH₃ | CH₂O(3SCH₃—C₆H₄) | OCH₂(CH₂)₅CH₃ |
| CH₂CH(CH₃)CH₂CH₂CH₃ | CH₂O(4CH₃—C₆H₄) | OCH₂C(C₆H₅) |
| CH₂CH(CH₃)CH₂CH₃ | CH₂O(2,4Cl—C₆H₃) | OCH₂(3CF₃—C₆H₄) |
| CH₂CH₂CH₂CH₂OCH₃ | CH₂O(2,6Cl—C₆H₃) | OCH₂(2Cl—C₆H₄) |
| CH₂CH₂CH₂—S—CH₂CH₃ | CH₂SCH₂CH₃ | OCH₂CH(CH₃)₂ |
| CH₂CH₂CH₂NHCH₂CH₃ | CH₂SCH₂CH₂CH₃ | O(C₆H₅) |
| CH₂CH₂NHCH₂CH₃ | CH₂SCH₂CH(CH₃)₂ | O(3CF₃—C₆H₄) |
| CH₂CF₂CH(CH₃)₂ | CH₂SCH₂(C₆H₅) | O(2Cl—C₆H₄) |
| CH₂CH₂CF₂CH₃ | CH₂SCH₂(3CF₃—C₆H₄) | O(4SCH₃—C₆H₄) |
| CH₂-cyclopropyl | CH₂S(2Cl—C₆H₄) | O(2,4Cl—C₆H₃) |
| CH₂-cyclobutyl | CH₂S(4CH₃—C₆H₄) | SCH₂CH₂CH₃ |
| CH₂-cyclopentyl | CH₂S(2,4Cl—C₆H₃) | SCH₂(CH₂)₂CH₃ |
| CH₂-cyclohexyl | CH₂S(3SCH₃—C₆H₄) | SCH₂(CH₂)₃CH₃ |
| cyclopropyl | CH₂S(2,6Cl—C₆H₃) | SCH₂(CH₂)SCH₃ |
| cyclobutyl | CH₂S(C₆H₅) | SCH₂(C₆H₅) |
| cyclopentyl | CH₂S(3CF₃—C₆H₄) | SCH₂(3SCH₃—C₆H₄) |
| cyclohexyl | CH₂S(2Cl—C₆H₄) | SCH₂(2OCH₃—C₆H₄) |
| CH₂OCH₂CH₃ | CH₂S(4CH₃—C₆H₄) | SCH₂(2Cl—C₆H₄) |
| CH₂OCH₂CH₂CH₃ | CH₂S(2,6Cl—C₆H₃) | SCH₂(2,4-C₆H₃) |
| | CH₂S(2,4Cl—C₆H₃) | SCH₂(4CF₃—C₆H₄) |
| | R³ | R¹ = Cl, R² = CO₂CH₃ |

| | | |
|---|---|---|
| S(CH3)3 | CH2CO2CH3 | (CH2)3CH3 |
| SCH2CH(CH3)2 | CH2CH2CO2CH2CH3 | CH2CH(CH3)2 |
| S(C6H5) | CH2CH2OCH2CH3 | CH2CH2CH(CH3)2 |
| S(3CF3—C6H4) | CH2NHCH2CH3 | CH2-cyclopentyl |
| S(2Cl—C6H4) | CH2CH2SCH2CH3 | CH2O(C6H5) |
| S(4OCH3—C6H4) | CH2CH2—NHCH2CH3 | CH3SCH2CH(CH3)2 |
| S(2,4Cl—C6H3) | CH2CH2N(CH3)CH2CH3 | CH2NHCH2CH(CH3)2 |
| S(2,6F—C6H3) | CH=CH(CH3)2 | OCH2CH(CH3)2 |
| 2(3CH3—C6H4) | CH2CH2CH=CH2 | NHCH2CH(CH3)2 |
| NHCH2CH2CH3 | CH2CH=CH—CH3 | C6H5 |
| NHCH2(CH2)2CH3 | CH=CH—CH2CH2—Cl | 3CF3—C6H4 |
| NHCH2(CH2)4CH3 | CH2CH2CH—ClCH2—Cl | 2Cl—C6H4 |
| NHCH2(CH2)5CH3 | C6H5 | |
| NHCH2CH(CH3)2 | 3CF3—C6H4 | R1 = Br, R2 = CO2CH3 |
| NHCH2(C6H5) | 2Cl—C6H4 | R3 |
| NHCH2(3CF3—C6H4) | 3CH3—C6H4 | (CH2)3CH3 |
| NHCH2(2Cl—C6H4) | 3OCH3—C6H4 | CH2CH(CH3)2 |
| NHCH2(4CH3—C6H4) | 2CF3—C6H4 | CH2CH2CH(CH3)2 |
| NHCH2(2,4Cl—C6H3) | 2,4Cl—C6H3 | CH2-cyclopentyl |
| NHCH2(2,6Cl—C6H3) | 2,6Cl—C6H3 | CH2O(C6H5) |
| NH(C6H5) | 2SCH3—C6H4 | CH3SCH2CH(CH3)2 |
| NH(3CF3—C6H4) | CH2(C6H5) | CH2NHCH2CH(CH3)2 |
| NH(2Cl—C6H4) | CH2(3CF3—C6H4) | OCH2CH(CH3)2 |
| NH(3CH3—C6H4) | CH2(2Cl—C6H4) | NHCH2CH(CH3)2 |
| NH(2,4Cl—C6H3) | CH2(4Cl—C6H4) | C6H5 |
| NH(2,6Cl—C6H3) | CH2(2,4Cl—C6H3) | 3CF3—C6H4 |
| N(CH3)(3CF3—C6H4) | CH2(3SCH3—C6H4) | 2Cl—C6H4 |
| N(CH3)CH2CH2CH3 | CH2(3OCH3—C6H4) | |
| N(CH2)4 | CH2(3Cl—C6H4) | R1 = I, R2 = CO2CH3 |
| N(CH2)5 | CH2(2,6F—C6H3) | R3 |
| N(CH2)6 | CH2(2,6Cl—C6H3) | (CH2)3CH3 |
| N(CH2CH2—OCH2CH2)2 | CH2(3,4F—C6H3) | CH2CH(CH3)2 |
| R3 | R3 | CH2CH2CH(CH3)2 |
| CH2CH(CH3)2 | CH2-cyclopentyl | CH2-cyclopentyl |
| CH2CH2CH(CH3)2 | CH2O(C6H5) | CH2O(C6H5) |
| CH2-cyclopentyl | CH3SCH2CH(CH3)2 | CH3SCH2CH(CH3)2 |
| CH2O(C6H5) | CH2NHCH2CH(CH3)2 | CH2NHCH2CH(CH3)2 |
| CH3SCH2CH(CH3)2 | OCH2CH(CH3)2 | OCH2CH(CH3)2 |
| CH2NHCH2CH(CH3)2 | NHCH2CH(CH3)2 | NHCH2CH(CH3)2 |
| OCH2CH(CH3)2 | C6H5 | C6H5 |
| NHCH2CH(CH3)2 | 3CF3—C6H4 | 3CF3—C6H4 |
| C6H5 | 2Cl—C6H4 | 2Cl—C6H4 |
| 3CF3—C6H4 | | |
| 2Cl—C6H4 | R1 = OCF2H, R2 = CO2CH3 | R1 = Br, R2 = CO2CH2CH3 |
| | R3 | R3 |
| R1 = OCH3, R2 = O2CH3 | (CH2)3CH3 | (CH2)3CH3 |
| R3 | CH2CH(CH3)2 | CH2CH(CH3)2 |
| (CH2)3CH3 | CH2CH2CH(CH3)2 | CH2CH2CH(CH3)2 |
| CH2CH(CH3)2 | CH2-cyclopentyl | CH2-cyclopentyl |
| CH2CH2CH(CH3)2 | CH2O(C6H5) | CH2O(C6H5) |
| CH2-cyclopentyl | CH3SCH2CH(CH3)2 | CH3SCH2CH(CH3)2 |
| CH2O(C6H5) | CH2NHCH2CH(CH3)2 | CH2NHCH2CH(CH3)2 |
| CH3SCH2CH(CH3)2 | OCH2CH(CH3)2 | OCH2CH(CH3)2 |
| CH2NHCH2CH(CH3)2 | NHCH2CH(CH3)2 | NHCH2CH(CH3)2 |
| OCH2CH(CH3)2 | C6H5 | C6H5 |

| | | |
|---|---|---|
| CH₂NHCH₂CH(CH₃)₂ | NHCH₂CH(CH₃)₂ | 3CF₃—C₆H₄ |
| OCH₂CH(CH₃)₂ | C₆H₅ | 2Cl—C₆H₄ |
| NHCH₂CH(CH₃)₂ | 3CF₃—C₆H₄ | |
| C₆H₅ | 2Cl—C₆H₄ | R¹ = I, R² = CO₂CH₂CH₃ |
| 3CF₃—C₆H₄ | | R³ |
| 2Cl—C₆H₄ | R¹ = Cl, R² = CO₂CH₂CH₃ | (CH₂)₃CH₃ |
| | R³ | CH₂CH(CH₃)₂ |
| R¹ = OCF₃, R² = CO₂CH₃ | (CH₂)₃CH₃ | CH₂CH₂CH(CH₃)₂ |
| R³ | CH₂CH(CH₃)₂ | CH₂-cyclopentyl |
| (CH₂)₃CH₃ | CH₂CH₂CH(CH₃)₂ | CH₂O(C₆H₅) |
| CH₂CH(CH₃)₂ | CH₂-cyclopentyl | CH₂SCH₂CH(CH₃)₂ |
| CH₂CH₂CH(CH₃)₂ | CH₂O(C₆H₅) | CH₂NHCH₂CH(CH₃)₂ |
| CH₂-cyclopentyl | | R³ |
| CH₂O(C₆H₅) | | 2Cl—C₆H₄ |
| CH₂SCH₂CH(CH₃)₂ | C₆H₅ | |
| CH₂NHCH₂CH(CH₃)₂ | 3CF₃—C₆H₄ | R¹ = Br, R² = CHO |
| OCH₂CH(CH₃)₂ | 2Cl—C₆H₄ | R³ |
| NHCH₂CH(CH₃)₂ | | (CH₂)₃CH₃ |
| C₆H₅ | R¹ = OCF₂H, R² = CO₂CH₂CH₃ | CH₂CH(CH₃)₂ |
| 3CF₃—C₆H₄ | R³ | CH₂CH₂CH(CH₃)₂ |
| 2Cl—C₆H₄ | (CH₂)₃CH₃ | CH₂-cyclopentyl |
| | CH₂CH(CH₃)₂ | CH₂O(C₆H₅) |
| R¹ = OCH₃, R² = CO₂¹CH₂CH₃ | CH₂CH₂CH(CH₃)₂ | CH₂SCH₂CH(CH₃)₂ |
| R³ | CH₂-cyclopentyl | CH₂NHCH₂CH(CH₃)₂ |
| (CH₂)₃CH₃ | CH₂O(C₆H₅) | OCH₂CH(CH₃)₂ |
| CH₂CH(CH₃)₂ | CH₂SCH₂CH(CH₃)₂ | NHCH₂CH(CH₃)₂ |
| CH₂CH₂CH(CH₃)₂ | CH₂NHCH₂CH(CH₃)₂ | C₆H₅ |
| CH₂-cyclopentyl | OCH₂CH(CH₃)₂ | 3CF₃—C₆H₄ |
| CH₂O(C₆H₅) | NHCH₂CH(CH₃)₂ | 2Cl—C₆H₄ |
| CH₂SCH₂CH(CH₃)₂ | C₆H₅ | |
| CH₂NHCH₂CH(CH₃)₂ | 3CF₃—C₆H₄ | R¹ = I, R² = CHO |
| OCH₂CH(CH₃)₂ | 2Cl—C₆H₄ | R³ |
| NHCH₂CH(CH₃)₂ | | (CH₂)₃CH₃ |
| C₆H₅ | R¹ = Cl, R² = CHO | CH₂CH(CH₃)₂ |
| 3CF₃—C₆H₄ | R³ | CH₂CH₂CH(CH₃)₂ |
| 2Cl—C₆H₄ | (CH₂)₃CH₃ | CH₂-cyclopentyl |
| R¹ = OCH₃, R² = CHO | CH₂CH(CH₃)₂ | CH₂O(C₆H₅) |
| R³ | CH₂CH₂CH(CH₃)₂ | CH₂SCH₂CH(CH₃)₂ |
| (CH₂)₃CH₃ | CH₂-cyclopentyl | CH₂NHCH₂CH(CH₃)₂ |
| CH₂CH(CH₃)₂ | CH₂O(C₆H₅) | OCH₂CH(CH₃)₂ |
| CH₂CH₂CH(CH₃)₂ | CH₂SCH₂CH(CH₃)₂ | NHCH₂CH(CH₃)₂ |
| CH₂-cyclopentyl | CH₂NHCH₂CH(CH₃)₂ | C₆H₅ |
| CH₂O(C₆H₅) | OCH₂CH(CH₃)₂ | 3CF₃—C₆H₄ |
| CH₂SCH₂CH(CH₃)₂ | | 2Cl—C₆H₄ |
| | | |
| | | R³ |
| | | CH₂-cyclopentyl |
| | | CH₂O(C₆H₅) |
| | | CH₂SCH₂CH(CH₃)₂ |
| | | CH₂NHCH₂CH(CH₃)₂ |
| | | OCH₂CH(CH₃)₂ |
| | | NHCH₂CH(CH₃)₂ |
| | | C₆H₅ |

-continued

| | | |
|---|---|---|
| CH₂NHCH₂CH(CH₃)₂ | NHCH₂CH(CH₃)₂ | 3CF₃—C₆H₄ |
| OCH₂CH(CH₃)₂ | C₆H₅ | 2Cl—C₆H₄ |
| NHCH₂CH(CH₃)₂ | 3CF₃—C₆H₄ | |
| C₆H₅ | 2Cl—C₆H₄ | |
| 3CF₃—C₆H₄ | | |
| 2Cl—C₆H₄ | | |
| | R¹ = Cl, R² = C≡CH | R¹ = I, R² = C≡CH |
| R¹ = OCF₃, R² = CHO | R³ | R³ |
| R³ | (CH₂)₃CH₃ | (CH₂)₃CH₃ |
| (CH₂)₃CH₃ | CH₂CH(CH₃)₂ | CH₂CH(CH₃)₂ |
| CH₂CH(CH₃)₂ | CH₂CH₂CH(CH₃)₂ | CH₂CH₂CH(CH₃)₂ |
| CH₂CH₂CH(CH₃)₂ | CH₂-cyclopentyl | CH₂-cyclopentyl |
| CH₂-cyclopentyl | CH₂O(C₆H₅) | CH₂O(C₆H₅) |
| CH₂O(C₆H₅) | CH₂SCH₂CH(CH₃)₂ | CH₂SCH₂CH(CH₃)₂ |
| CH₂SCH₂CH(CH₃)₂ | CH₂NHCH₂CH(CH₃)₂ | CH₂NHCH₂CH(CH₃)₂ |
| CH₂NHCH₂CH(CH₃)₂ | OCH₂CH(CH₃)₂ | OCH₂CH(CH₃)₂ |
| OCH₂CH(CH₃)₂ | NHCH₂CH(CH₃)₂ | NHCH₂CH(CH₃)₂ |
| NHCH₂CH(CH₃)₂ | C₆H₅ | C₆H₅ |
| C₆H₅ | 3CF₃—C₆H₄ | 3CF₃—C₆H₄ |
| 3CF₃—C₆H₄ | 2Cl—C₆H₄ | 2Cl—C₆H₄ |
| 2Cl—C₆H₄ | | |
| | R¹ = Br, R² = C≡CH | R¹ = OCH₃, R² = C≡CH |
| R¹ = OCF₂H, R² = CHO | R³ | R³ |
| R³ | (CH₂)₃CH₃ | (CH₂)₃CH₃ |
| (CH₂)₃CH₃ | CH₂CH(CH₃)₂ | CH₂CH(CH₃)₂ |
| CH₂CH(CH₃)₂ | CH₂CH₂CH(CH₃)₂ | CH₂CH₂CH(CH₃)₂ |
| CH₂SCH₂CH(CH₃)₂ | CH₂-cyclopentyl | CH₂-cyclopentyl |
| OCH₂CH(CH₃)₂ | CH₂O(C₆H₅) | CH₂O(C₆H₅) |
| NHCH₂CH(CH₃)₂ | | |
| C₆H₅ | | |
| 3CF₃—C₆H₄ | | |
| 2Cl—C₆H₄ | | |
| | R¹ = Cl, R² = CH=N—OH | R¹ = I, R² = CH=N—OH |
| R¹ = OCF₃, R² = C≡CH | R³ | R³ |
| R³ | (CH₂)₃CH₃ | (CH₂)₃CH₃ |
| (CH₂)₃CH₃ | CH₂CH(CH₃)₂ | CH₂CH(CH₃)₂ |
| CH₂CH(CH₃)₂ | CH₂CH₂CH(CH₃)₂ | CH₂CH₂CH(CH₃)₂ |
| CH₂CH₂CH(CH₃)₂ | CH₂-cyclopentyl | CH₂-cyclopentyl |
| CH₂-cyclopentyl | CH₂O(C₆H₅) | CH₂O(C₆H₅) |
| CH₂O(C₆H₅) | CH₂SCH₂CH(CH₃)₂ | CH₂SCH₂CH(CH₃)₂ |
| CH₂SCH₂CH(CH₃)₂ | CH₂NHCH₂CH(CH₃)₂ | CH₂NHCH₂CH(CH₃)₂ |
| CH₂NHCH₂CH(CH₃)₂ | OCH₂CH(CH₃)₂ | OCH₂CH(CH₃)₂ |
| OCH₂CH(CH₃)₂ | NHCH₂CH(CH₃)₂ | NHCH₂CH(CH₃)₂ |
| NHCH₂CH(CH₃)₂ | C₆H₅ | C₆H₅ |
| C₆H₅ | 3CF₃—C₆H₄ | 3CF₃—C₆H₄ |
| 3CF₃—C₆H₄ | 2Cl—C₆H₄ | 2Cl—C₆H₄ |
| 2Cl—C₆H₄ | | |
| | R¹ 32 Br, R² = CH=N—OH | R¹ = OCH₃, R² = CH=N—OH |
| R¹ = OCF₂H, R² = C≡CH | R³ | R³ |
| R³ | (CH₂)₃CH₃ | (CH₂)₃CH₃ |
| (CH₂)₃CH₃ | CH₂CH(CH₃)₂ | CH₂CH(CH₃)₂ |
| CH₂CH(CH₃)₂ | CH₂CH₂CH(CH₃)₂ | CH₂CH₂CH(CH₃)₂ |
| | CH₂-cyclopentyl | CH₂-cyclopentyl |
| | | CH₂O(C₆H₅) |
| | | CH₂SCH₂CH(CH₃)₂ |

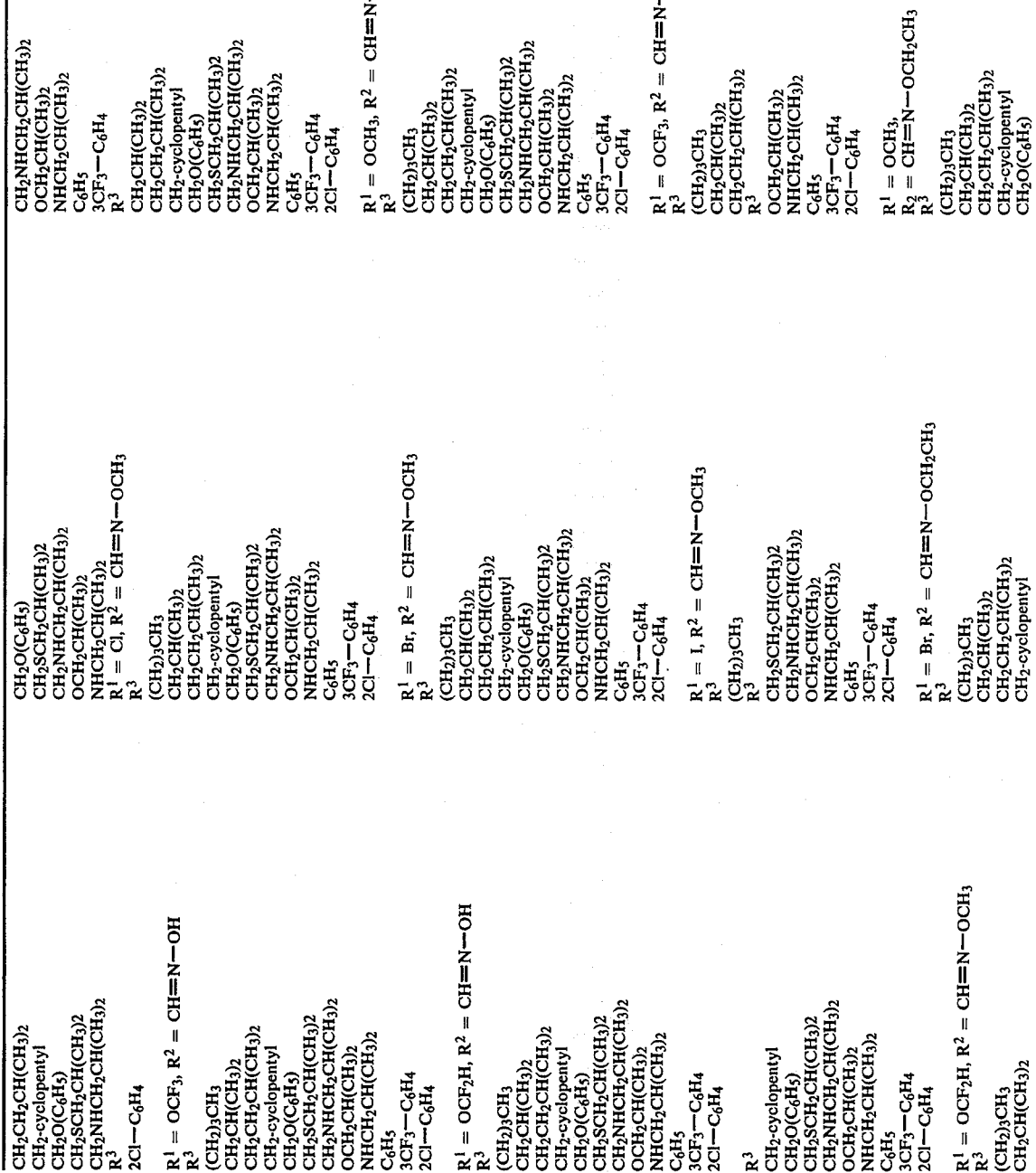

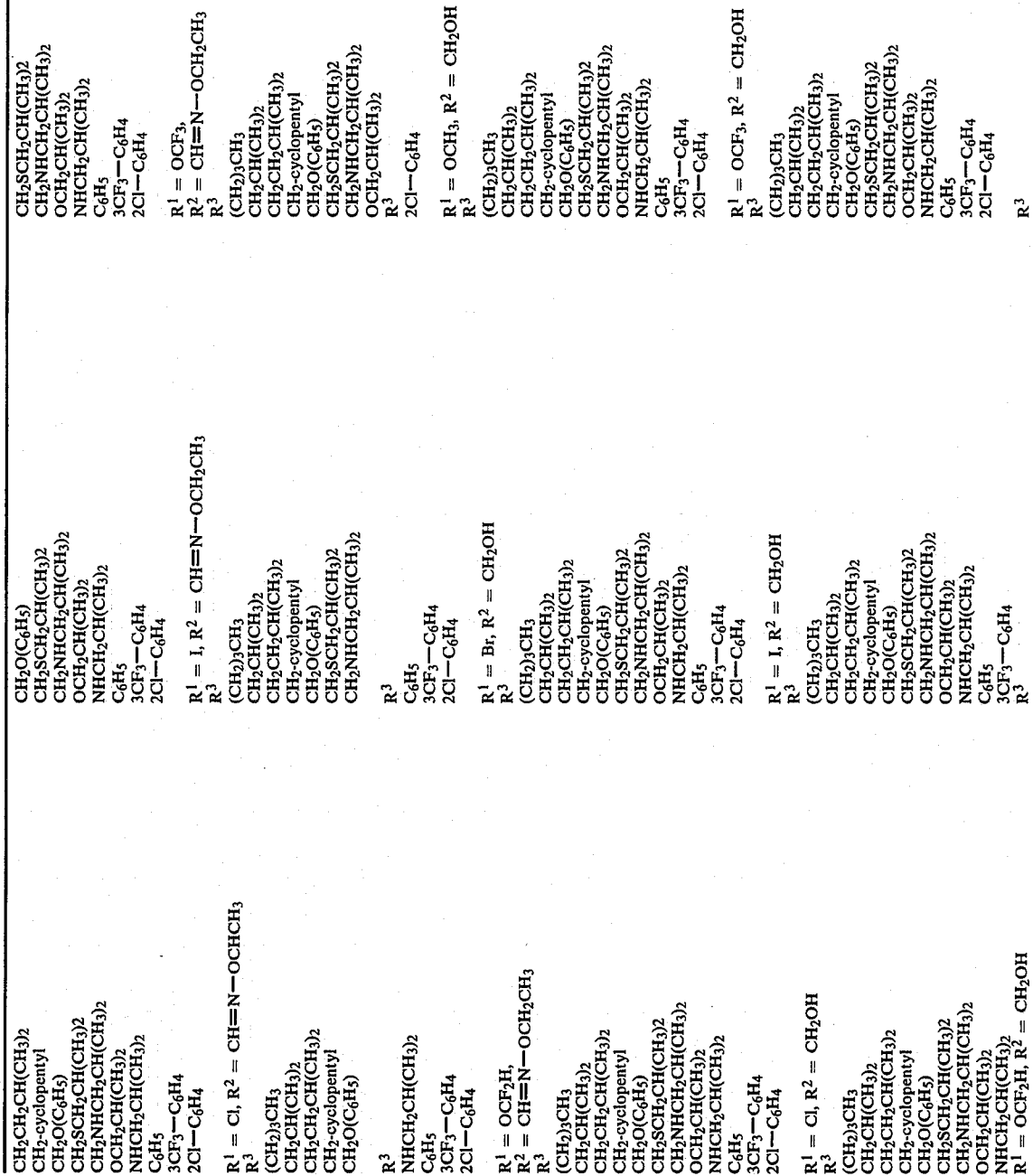

| $R^3$ | |
|---|---|
| (CH$_2$)$_3$CH$_3$ | 2Cl—C$_6$H$_4$ |
| CH$_2$CH(CH$_3$)$_2$ | $R^1$ = Br, 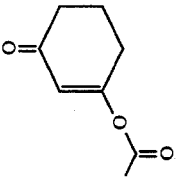  $R^2$=Z |
| CH$_2$CH$_2$CH(CH$_3$)$_2$ | CH$_2$CH$_2$CH(CH$_3$)$_2$ |
| CH$_2$-cyclopentyl | CH$_2$-cyclopentyl |
| CH$_2$O(C$_6$H$_5$) | CH$_2$O(C$_6$H$_5$) |
| CH$_2$SCH$_2$CH(CH$_3$)$_2$ | CH$_2$SCH$_2$CH(CH$_3$)$_2$ |
| CH$_2$NHCH$_2$CH(CH$_3$)$_2$ | CH$_2$NHCH$_2$CH(CH$_3$)$_2$ |
| | OCH$_2$CH(CH$_3$)$_2$ |
| OCH$_2$CH(CH$_3$)$_2$ | NHCH$_2$CH(CH$_3$)$_2$ |
| NHCH$_2$CH(CH$_3$)$_2$ | C$_6$H$_5$ |
| C$_6$H$_5$ | 3CF$_3$—C$_6$H$_4$ |
| 3CF$_3$—C$_6$H$_4$ | 2Cl—C$_6$H$_4$ |
| 2Cl—C$_6$H$_4$ | $R^1$ = OCH$_3$ 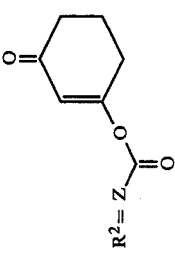  $R^2$=Z |
| $R^1$ = Cl, 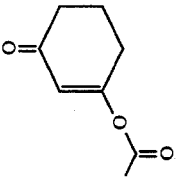  $R^2$=Z | |
| $R^3$ | $R^3$ |
| (CH$_2$)$_3$CH$_3$ | (CH$_2$)$_3$CH$_3$ |
| CH$_2$CH(CH$_3$)$_2$ | CH$_2$CH(CH$_3$)$_2$ |
| CH$_2$CH$_2$CH(CH$_3$)$_2$ | CH$_2$CH$_2$CH(CH$_3$)$_2$ |
| CH$_2$-cyclopentyl | CH$_2$-cyclopentyl |
| CH$_2$O(C$_6$H$_5$) | CH$_2$O(C$_6$H$_5$) |
| CH$_2$SCH$_2$CH(CH$_3$)$_2$ | CH$_2$SCH$_2$CH(CH$_3$)$_2$ |
| CH$_2$NHCH$_2$CH(CH$_3$)$_2$ | CH$_2$NHCH$_2$CH(CH$_3$)$_2$ |
| OCH$_2$CH(CH$_3$)$_2$ | OCH$_2$CH(CH$_3$)$_2$ |
| | NHCH$_2$CH(CH$_3$)$_2$ |
| | C$_6$H$_5$ |
| | 3CF$_3$—C$_6$H$_4$ |
| | 2Cl—C$_6$H$_4$ |
| | $R^1$ = I, 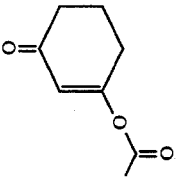  $R^2$=Z |
| | $R^3$ |
| | 3CF$_3$—C$_6$H$_4$ |

-continued

| | | |
|---|---|---|
| NHCH$_2$CH(CH$_3$)$_2$<br>C$_6$H$_5$<br>3CF$_3$—C$_6$H$_4$<br>R$^1$ = OCF$_3$,<br>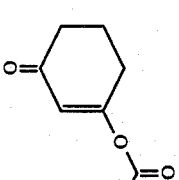<br>R$^2$= Z—CO | (CH$_2$)$_3$CH$_3$<br>CH$_2$CH(CH$_3$)$_2$<br>R$^3$ | 2Cl—C$_6$H$_4$<br>R$^3$<br>CH$_2$CH(CH$_3$)$_2$<br>CH$_2$CH$_2$CH(CH$_3$)$_2$<br>CH$_2$-cyclopent yl<br>CH$_2$O(C$_6$H$_5$)<br>CH$_2$SCH$_2$CH(CH$_3$)$_2$<br>CH$_2$NHCH$_2$CH(CH$_3$)$_2$ |
| R$^3$<br>(CH$_2$)$_3$CH$_3$<br>CH$_2$CH(CH$_3$)$_2$<br>CH$_2$CH$_2$CH(CH$_3$)$_2$<br>CH$_2$-cyclopentyl<br>CH$_2$O(C$_6$H$_5$)<br>CH$_3$SCH$_2$CH(CH$_3$)$_2$<br>CH$_2$NHCH$_2$CH(CH$_3$)$_2$<br>OCH$_2$CH(CH$_3$)$_2$<br>NHCH$_2$CH(CH$_3$)$_2$<br>C$_6$H$_5$<br>3CF$_3$—C$_6$H$_4$<br>2Cl—C$_6$H$_4$<br>R$^1$ = OCF$_2$H, | 2Cl—C$_6$H$_4$<br>R$^1$ = Cl,<br>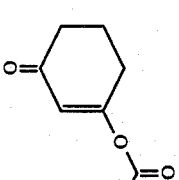<br>R$^2$ = —CO | OCH$_2$CH(CH$_3$)$_2$<br>NHCH$_2$CH(CH$_3$)$_2$<br>C$_6$H$_5$<br>3CF$_3$—C$_6$H$_4$<br>2Cl—C$_6$H$_4$<br>R$^1$ = OCH$_3$,<br><br>R$^2$ = —CO |
| <br>R$^2$= Z—CO<br>R$^3$<br>(CH$_2$)$_3$CH$_3$<br>CH$_2$CH(CH$_3$)$_2$<br>CH$_2$CH$_2$CH(CH$_3$)$_2$ | R$^3$<br>(CH$_2$)$_3$CH$_3$<br>CH$_2$CH(CH$_3$)$_2$<br>CH$_2$CH$_2$CH(CH$_3$)$_2$<br>CH$_2$-cyclopentyl<br>CH$_2$O(C$_6$H$_5$)<br>CH$_3$SCH$_2$CH(CH$_3$)$_2$<br>CH$_2$NHCH$_2$CH(CH$_3$)$_2$<br>OCH$_2$CH(CH$_3$)$_2$<br>NHCH$_2$CH(CH$_3$)$_2$<br>C$_6$H$_5$<br>3CF$_3$—C$_6$H$_4$<br>2Cl—C$_6$H$_4$<br>R$^1$ = Br,<br><br>R$^2$ = —CO | R$^3$<br>(CH$_2$)$_3$CH$_3$<br>CH$_2$CH(CH$_3$)$_2$<br>CH$_2$CH$_2$CH(CH$_3$)$_2$<br>CH$_2$-cyclopentyl<br>CH$_2$O(C$_6$H$_5$)<br>CH$_2$NHCH$_2$CH(CH$_3$)$_2$<br>OCH$_2$CH(CH$_3$)$_2$<br>NHCH$_2$CH(CH$_3$)$_2$<br>C$_6$H$_5$<br>3CF$_3$—C$_6$H$_4$<br>2Cl—C$_6$H$_4$ |

-continued

| | | |
|---|---|---|
| CH₂-cyclopentyl<br>CH₂O(C₆H₅)<br>R¹ = OCF₃, | ![cyclopentenone structure]<br><br>R² = —CO | R³<br>(CH₂)₃CH₃<br>R³ |
| | | NHCH₂CH(CH₃)₂<br>C₆H₅<br>3CF₃—C₆H₄ |
| R² = —CO | | |
| | | 2Cl—C₆H₄ |
| R³<br>(CH₂)₃CH₃ | | |
| CH₂CH(CH₃)₂<br>CH₂CH₂CH(CH₃)₂ | R¹ = Cl, R² = CH₂—O—C(O)—CH₃ | R¹ = I, R² = CH₂—O—C(O)—CH₃ |
| CH₂-cyclopentyl<br>CH₂O(C₆H₅)<br>CH₂SCH₂CH(CH₃)₂<br>CH₂NHCH₂CH(CH₃)₂<br>OCH₂CH(CH₃)₂<br>NHCH₂CH(CH₃)₂<br>C₆H₅<br>3CF₃—C₆H₄<br>2Cl—C₆H₄<br>R¹ = OCF₃H, | R³<br>(CH₂)₃CH₃<br>CH₂CH(CH₃)₂<br>CH₂CH₂CH(CH₃)₂<br>CH₂-cyclopentyl<br>CH₂O(C₆H₅)<br>CH₂SCH₂CH(CH₃)₂<br>CH₂NHCH₂CH(CH₃)₂<br>OCH₂CH(CH₃)₂<br>NHCH₂CH(CH₃)₂ | R³<br>(CH₂)₃CH₃<br>CH₂CH(CH₃)₂<br>CH₂CH₂CH(CH₃)₂<br>CH₂-cyclopentyl<br>CH₂O(C₆H₅)<br>CH₂SCH₂CH(CH₃)₂<br>CH₂NHCH₂CH(CH₃)₂<br>OCH₂CH(CH₃)₂<br>NHCH₂CH(CH₃)₂ |
| | R¹ = Br, R² = CH₂—O—C(O)—CH₃ | C₆H₅<br>3CF₃—C₆H₄<br>2Cl—C₆H₄<br>R¹ = OCH₃, |
| R² = Z—C(=O)—G (cyclopentenone) | R³ | R¹ = CH₂—O—C(O)—CH₃ |
| R³<br>CH₂NHCH₂CH(CH₃)₂<br>OCH₂CH(CH₃)₂ | (CH₂)₃CH₃<br>CH₂CH(CH₃)₂<br>CH₂CH₂CH(CH₃)₂<br>CH₂-cyclopentyl<br>CH₂O(C₆H₅)<br>CH₂SCH₂CH(CH₃)₂<br>CH₂NHCH₂CH(CH₃)₂<br>OCH₂CH(CH₃)₂<br>R³<br>CH₂O(C₆H₅)<br>CH₂SCH₂CH(CH₃)₂ | R³<br>(CH₂)₃CH₃<br>CH₂CH(CH₃)₂<br>CH₂CH₂CH(CH₃)₂<br>CH₂-cyclopentyl<br>CH₂O(C₆H₅)<br>CH₂SCH₂CH(CH₃)₂<br>CH₂NHCH₂CH(CH₃)₂<br>OCH₂CH(CH₃)₂<br>R³<br>CH₂O(C₆H₅)<br>CH₂SCH₂CH(CH₃)₂ |

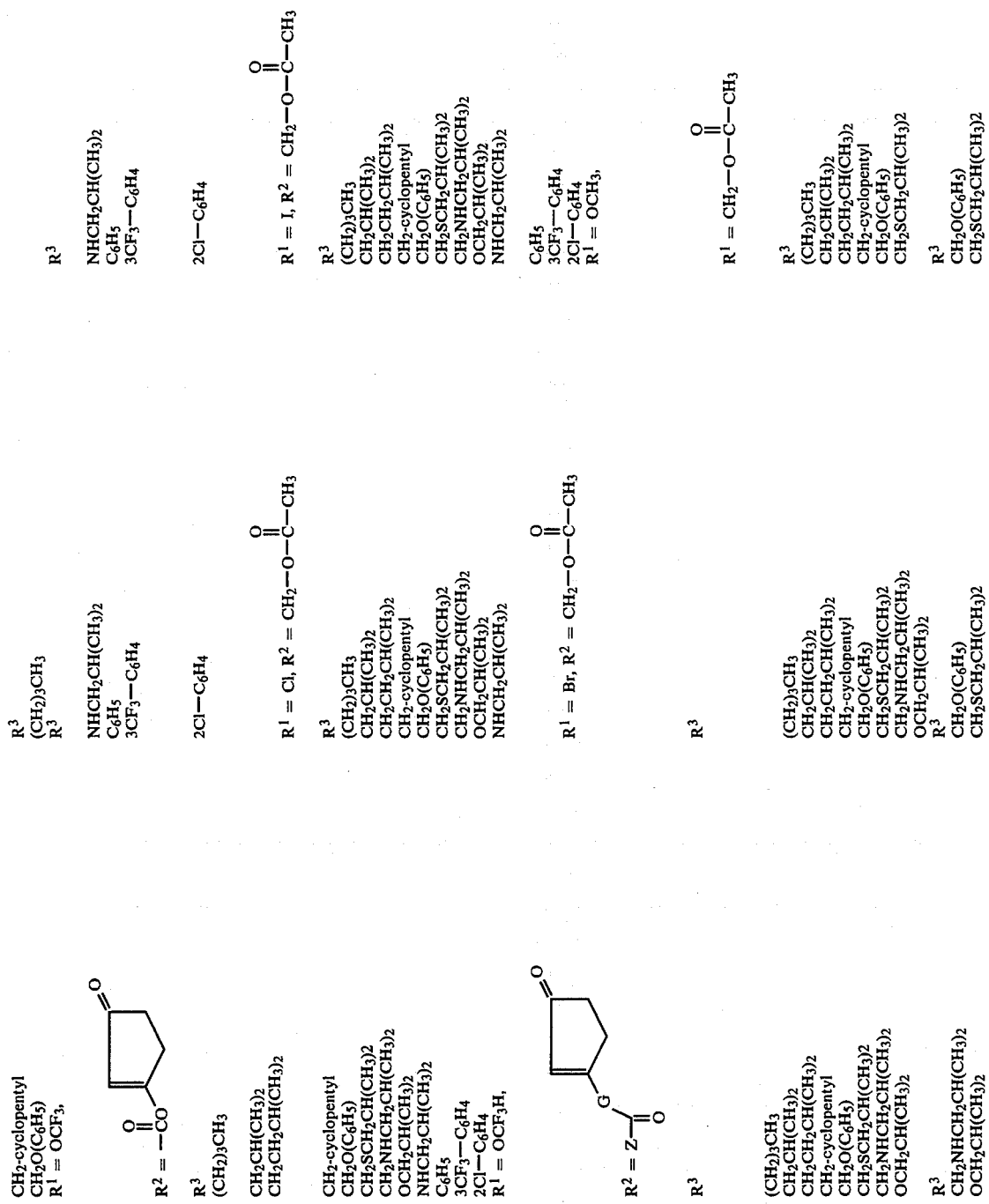

-continued

| | |
|---|---|
| NHCH₂CH(CH₃)₂ | CH₂NHCH₂CH(CH₃)₂ |
| C₆H₅ | OCH₂CH(CH₃)₂ |
| 3CF₃—C₆H₄ | NHCH₂CH(CH₃)₂ |
| 2Cl—C₆H₄ | C₆H₅ |
| | 3CF₃—C₆H₄ |
| R¹ = OCF₃, | 2Cl—C₆H₄ |

$R^1 = CH_2 - O - \overset{\overset{O}{\|}}{C} - CH_3$ $\quad$ $R^1 = Cl, R^2 = \overset{\overset{S}{\|}}{C} - OCH_3$ $\quad$ $R^1 = I, R^2 = \overset{\overset{S}{\|}}{C} - OCH_3$

| R³ | R³ | R³ |
|---|---|---|
| (CH₂)₃CH₃ | (CH₂)₃CH₃ | (CH₂)₃CH₃ |
| CH₂CH(CH₃)₂ | CH₂CH(CH₃)₂ | CH₂CH(CH₃)₂ |
| CH₂CH₂CH(CH₃)₂ | CH₂CH₂CH(CH₃)₂ | CH₂CH₂CH(CH₃)₂ |
| CH₂-cyclopentyl | CH₂-cyclopentyl | CH₂-cyclopentyl |
| CH₂O(C₆H₅) | CH₂O(C₆H₅) | |
| CH₂SCH₂CH(CH₃)₂ | CH₂SCH₂CH(CH₃)₂ | |
| CH₂NHCH₂CH(CH₃)₂ | CH₂NHCH₂CH(CH₃)₂ | |
| OCH₂CH(CH₃)₂ | OCH₂CH(CH₃)₂ | |
| NHCH₂CH(CH₃)₂ | NHCH₂CH(CH₃)₂ | |
| C₆H₅ | C₆H₅ | |
| 3CF₃—C₆H₄ | 3CF₃—C₆H₄ | |
| 2Cl—C₆H₄ | 2Cl—C₆H₄ | |

$R^1 = OCF_2H, R^2 = CH_2 - \overset{\overset{O}{\|}}{C} - CH_3$ $\quad$ $R^1 = Br, R^2 = \overset{\overset{S}{\|}}{C} - OCH_3$ $\quad$ $R^1 = OCH_3, R^2 = \overset{\overset{S}{\|}}{C} - OCH_3$

| R³ | R³ | R³ |
|---|---|---|
| (CH₂)₃CH₃ | (CH₂)₃CH₃ | (CH₂)₃CH₃ |
| CH₂CH(CH₃)₂ | CH₂CH(CH₃)₂ | CH₂CH(CH₃)₂ |
| CH₂CH₂CH(CH₃)₂ | CH₂CH₂CH(CH₃)₂ | CH₂CH₂CH(CH₃)₂ |
| CH₂-cyclopentyl | CH₂-cyclopentyl | CH₂-cyclopentyl |

| | |
|---|---|
| R³ | R³ |
| CH₂O(C₆H₅) | CH₂O(C₆H₅) |
| CH₂SCH₂CH(CH₃)₂ | CH₂SCH₂CH(CH₃)₂ |
| CH₂NHCH₂CH(CH₃)₂ | CH₂NHCH₂CH(CH₃)₂ |
| OCH₂CH(CH₃)₂ | OCH₂CH(CH₃)₂ |
| NHCH₂CH(CH₃)₂ | NHCH₂CH(CH₃)₂ |
| C₆H₅ | C₆H₅ |
| 3CF₃—C₆H₄ | 3CF₃—C₆H₄ |
| 2Cl—C₆H₄ | 2Cl—C₆H₄ |
| | |
| $R^1 = OCF_3, R^2 = \overset{S}{\underset{\|}{C}}-OCH_3$ | $R^1 = I, R^2 = \overset{O}{\underset{\|}{C}}-NHCH_3$ |
| R³ | R³ |
| (CH₂)₃CH₃ | (CH₂)₃CH₃ |
| CH₂CH(CH₃)₂ | CH₂CH(CH₃)₂ |
| CH₂CH₂CH(CH₃)₂ | CH₂CH₂CH(CH₃)₂ |
| CH₂-cyclopentyl | CH₂-cyclopentyl |
| CH₂O(C₆H₅) | CH₂O(C₆H₅) |
| CH₂SCH₂CH(CH₃)₂ | CH₂SCH₂CH(CH₃)₂ |
| CH₂NHCH₂CH(CH₃)₂ | CH₂NHCH₂CH(CH₃)₂ |
| OCH₂CH(CH₃)₂ | OCH₂CH(CH₃)₂ |
| NHCH₂CH(CH₃)₂ | NHCH₂CH(CH₃)₂ |
| C₆H₅ | C₆H₅ |
| 3CF₃—C₆H₄ | 3CF₃—C₆H₄ |
| 2Cl—C₆H₄ | 2Cl—C₆H₄ |
| | |
| $R^1 = OCF_2H, R^2 = \overset{S}{\underset{\|}{C}}-OCH_3$ | $R^1 = OCH_3, R^2 = \overset{O}{\underset{\|}{C}}-NHCH_3$ |
| R³ | R³ |
| (CH₂)₃CH₃ | (CH₂)₃CH₃ |
| CH₂CH(CH₃)₂ | CH₂CH(CH₃)₂ |
| CH₂CH₂CH(CH₃)₂ | CH₂CH₂CH(CH₃)₂ |
| CH₂-cyclopentyl | CH₂-cyclopentyl |
| CH₂O(C₆H₅) | CH₂O(C₆H₅) |
| CH₂SCH₂CH(CH₃)₂ | CH₂SCH₂CH(CH₃)₂ |
| CH₂NHCH₂CH(CH₃)₂ | CH₂NHCH₂CH(CH₃)₂ |
| OCH₂CH(CH₃)₂ | OCH₂CH(CH₃)₂ |
| NHCH₂CH(CH₃)₂ | NHCH₂CH(CH₃)₂ |
| C₆H₅ | C₆H₅ |
| 3CF₃—C₆H₄ | 3CF₃—C₆H₄ |
| 2Cl—C₆H₄ | 2Cl—C₆H₄ |
| | |
| $R^1 = Br, R^2 = \overset{O}{\underset{\|}{C}}-NHCH_3$ | |
| R³ | |
| (CH₂)₃CH₃ | |
| CH₂CH(CH₃)₂ | |
| CH₂CH₂CH(CH₃)₂ | |
| CH₂-cyclopentyl | |
| CH₂O(C₆H₅) | |
| CH₂SCH₂CH(CH₃)₂ | |
| CH₂NHCH₂CH(CH₃)₂ | |
| OCH₂CH(CH₃)₂ | |
| NHCH₂CH(CH₃)₂ | |
| C₆H₅ | |
| 3CF₃—C₆H₄ | |
| 2Cl—C₆H₄ | |
| | |
| $R^1 = Cl, R^2 = CH=C\genfrac{}{}{0pt}{}{\overset{S}{\underset{\|}{C}}NH_2}{C\equiv N}$ | |
| | |
| $R^1 = Cl, R^2 = \overset{O}{\underset{\|}{C}}-NHCH_3$ | |

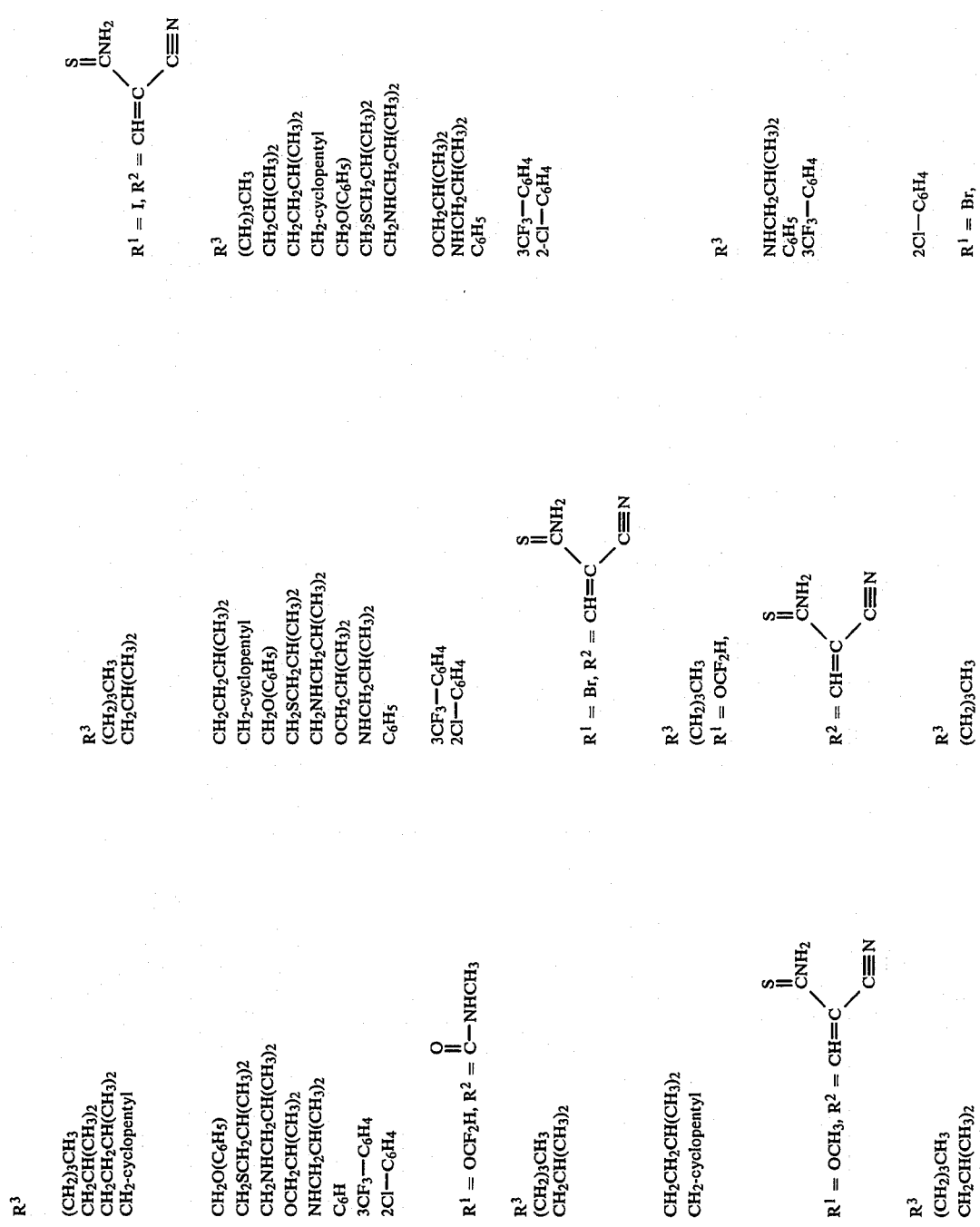

-continued

| | | | | |
|---|---|---|---|---|
| CH$_2$CH$_2$CH(CH$_3$)$_2$ | | CH$_2$CH(CH$_3$)$_2$ | | |
| CH$_2$-cyclopentyl | | CH$_2$CH$_2$CH(CH$_3$)$_2$ | | |
| CH$_2$O(C$_6$H$_5$) | | CH$_2$-cyclopentyl | | |
| CH$_2$SCH$_2$CH(CH$_3$)$_2$ | | CH$_2$O(C$_6$H$_5$) | | R$^2$ = CH=C 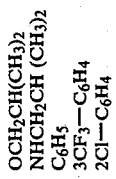 |
| | | | | |
| CH$_2$NHCH$_2$CH(CH$_3$)$_2$ | | CH$_2$SCH$_2$CH(CH$_3$)$_2$ | | R$^3$ |
| OCH$_2$CH(CH$_3$) | | CH$_2$NHCH$_2$CH(CH$_3$)$_2$ | | (CH$_2$)$_3$CH$_3$ |
| NHCH$_2$CH(CH$_3$)$_2$ | | OCH$_2$CH(CH$_3$)$_2$ | | CH$_2$CH(CH$_3$) |
| C$_6$H$_5$ | | NHCH$_2$CH(CH$_3$)$_2$ | | CH$_2$CH$_2$CH(CH$_3$)$_2$ |
| 3CF$_3$—C$_6$H$_4$ | | C$_6$H$_5$ | | CH$_2$-cyclopentyl |
| 2Cl—C$_6$H$_4$ | | 3CF$_3$—C$_6$H$_4$ | | CH$_2$O(C$_6$H$_5$) |
| | | 2-Cl—C$_6$H$_4$ | | CH$_2$SCH$_2$CH(CH$_3$)$_2$ |
| R$^1$ = OCF$_3$, R$^2$ = CH=C  | | R$^1$ = Cl, | | |
| | | | | OCH$_2$CH(CH$_3$)$_2$ |
| R$^3$ | | R$^2$ = CH=C 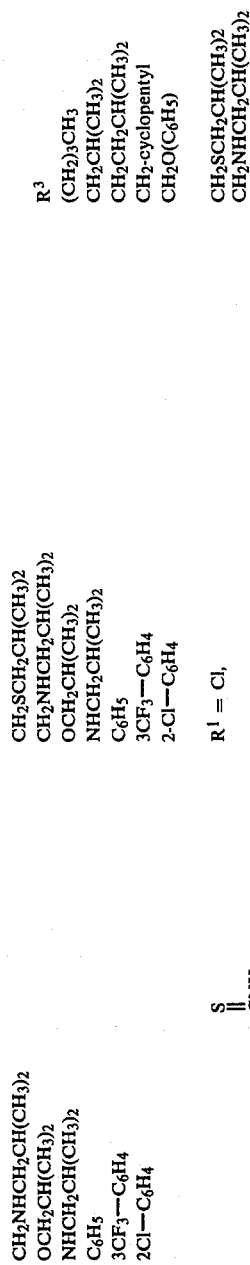 | | NHCH$_2$CH (CH$_3$)$_2$ |
| (CH$_2$)$_3$CH$_3$ | | | | C$_6$H$_5$ |
| CH$_2$CH(CH$_3$)$_2$ | | | | 3CF$_3$—C$_6$H$_4$ |
| CH$_2$CH$_2$CH(CH$_3$)$_2$ | | R$^3$ | | 2Cl—C$_6$H$_4$ |
| | | (CH$_2$)$_3$CH$_3$ | | |
| CH$_2$-cyclopentyl | | CH$_2$CH(CH$_3$)$_2$ | | R$^1$ = I, |
| CH$_2$O(C$_6$H$_5$) | | CH$_2$CH$_2$CH(CH$_3$)$_2$ | | |
| | | CH$_2$-cyclopentyl | | R$^2$ = CH=C 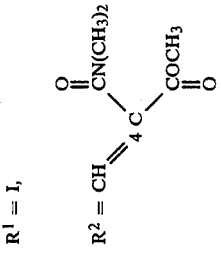 |
| CH$_2$SCH$_2$CH(CH$_3$)$_2$ | | CH$_2$O(C$_6$H$_5$) | | |
| CH$_2$NHCH$_2$CH(CH$_3$)$_2$ | | CH$_2$SCH$_2$CH(CH$_3$)$_2$ | | |
| OCH$_2$C-H(CH$_3$) | | | | |
| NHCH$_2$CH(CH$_3$)$_2$C$_6$H$_5$ | | | | R$^3$ |
| | | | | (CH$_2$)$_3$CH$_3$ |
| 3CF$_3$—C$_6$H$_4$ | | CH$_2$NHCH$_2$CH(CH$_3$)$_2$ | | R$^3$ |
| 2Cl—C$_6$H$_4$ | | OCH$_2$CH(CH$_3$)$_2$ | | |
| R$^3$ | | R$^1$ = OCF$_3$, | | |

-continued

| | | |
|---|---|---|
| CH₂CH(CH₃)₂ | | OCH₂CH(CH₃)₂ |
| CH₂CH₂CH(CH₃)₂ | | NHCH₂CH(CH₃)₂ |
| CH₂-cyclopentyl | | C₆H₅ |
| CH₂O(C₆H₅) | | 3CF₃—C₆H₄ |
| | | 2Cl—C₆H₄ |

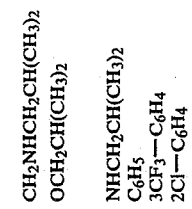

R² = CH=C(CN(CH₃)₂)(COCH₃)  →  R¹ = Cl, R² = CH=C(COCH₃)(COCH₃)

| | | |
|---|---|---|
| CH₂SCH₂CH(CH₃)₂ | | R³ |
| CH₂NHCH₂CH(CH₃)₂ | | (CH₂)₃CH₃ |
| OCH₂CH(CH₃)₂ | | CH₂CH(CH₃)₂ |
| NHCH₂CH(CH₃)₂ | | |
| C₆H₅ | | CH₂CH₂CH(CH₃)₂ |
| 3CF₃—C₆H₄ | | CH₂-cyclopentyl |
| 2Cl—C₆H₄ | | CH₂O(C₆H₅) |
| | | CH₂SCH₂CH(CH₃)₂ |

R¹ = OCH₃,

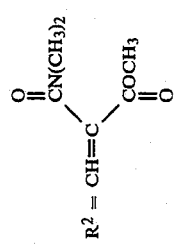

R² = CH=C(CN(CH₃)₂)(COCH₃)

| | | |
|---|---|---|
| R³ | | CH₂NHCH₂CH(CH₃)₂ |
| (CH₂)₃CH₃ | | OCH₂CH(CH₃)₂ |
| CH₂CH(CH₃)₂ | | |
| CH₂CH₂CH(CH₃)₂ | | NHCH₂CH(CH₃)₂ |
| CH₂-cyclopentyl | | C₆H₅ |
| CH₂O(C₆H₅) | | 3CF₃—C₆H₄ |
| | | 2Cl—C₆H₄ |

R¹ = OCF₂H,

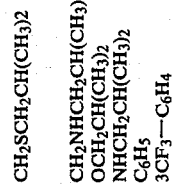

R² = CH=C(CN(CH₃)₂)(COCH₃)

R³

CH₂SCH₂CH(CH₃)₂

-continued

| | | |
|---|---|---|
| CH₂NHCH₂CH(CH₃)₂ | | |
| OCH₂CH(CH₃)₂ | (CH₂)₃CH₃ | |
| NHCH₂CH(CH₃)₂ | CH₂CH(CH₃)₂ | |
| C₆H₅ | CH₂CH₂CH(CH₃)₂ | |
| | CH₂-cyclopentyl | R¹ = Br, R² = CH=C(COCH₃)(COCH₃) |
| 3CF₃—C₆H₄ | CH₂O(C₆H₅) | |
| 2Cl—C₆H₄ | CH₂SCH₂CH(CH₃)₂ | |
| R³ | CH₂NHCH₂CH(CH₃)₂ | R³ |
| | R¹ = OCH₃, | (CH₂)₃CH₃ |
| | | CH₂CH(CH₃)₂ |
| | | R³ |
| CH₂CH₂CH(CH₃)₂ | | OCH₂CH(CH₃)₂ |
| CH₂-cyclopentyl | | NHCH₂CH(CH₃)₂ |
| CH₂O(C₆H₅) | R² = CH=C(COCH₃)(COCH₃) | C₆H₅ |
| CH₂SCH₂CH(CH₃)₂ | | 3CF₃—C₆H₄ |
| | | 2Cl—C₆H₄ |
| CH₂NHCH₂CH(CH₃)₂ | R³ | |
| OCH₂CH(CH₃)₂ | (CH₂)₃CH₃ | R¹ = OCF₂H, |
| NHCH₂CH(CH₃)₂ | CH₂CH(CH₃)₂ | |
| C₆H₅ | CH₂CH₂CH(CH₃)₂ | |
| 3CF₃—C₆H₄ | CH₂-cyclopentyl | |
| 2Cl—C₆H₄ | CH₂O(C₆H₅) | R² = CH=C(COCH₃)(COCH₃) |
| R¹ = I, R² = CH=C(COCH₃)(COCH₃) | CH₂SCH₂CH(CH₃)₂ | |
| | CH₂NHCH₂CH(CH₃)₂ | R³ |
| | OCH₂CH(CH₃)₂ | (CH₂)₃CH₃ |
| R³ | NHCH₂CH(CH₃)₂ | CH₂CH(CH₃)₂ |
| (CH₂)₃CH₃ | C₆H₅ | CH₂CH₂CH(CH₃)₂ |
| CH₂CH(CH₃)₂ | | |
| CH₂CH₂CH(CH₃)₂ | 3CF₃—C₆H₄ | CH₂-cyclopentyl |
| | 2Cl—C₆H₄ | CH₂O(C₆H₅) |
| | R¹ = OCF₃, | CH₂SCH₂CH(CH₃)₂ |
| | | CH₂NHCH₂CH(CH₃)₂ |

-continued

CH2-cyclopentyl
CH2O(C6H5)
CH2SCH2CH(CH3)2
CH2NHCH2CH(CH3)2

OCH2CH(CH3)2
NHCH2CH(CH3)2
C6H5
3CF3—C6H4
2Cl—C6H4

R² = CH=C(COCH3)(COCH3)

R³
(CH2)3CH3
CH2CH(CH3)2
CH2CH2CH(CH3)2
CH2-cyclopentyl
CH2O(C6H5)
CH2SCH2CH(CH3)2
CH2NHCH2CH(CH3)2
CH2O(C6H5)
R¹ = I, R² = CH=CHC(=O)—N(morpholino)

R³
CH2CH2CH(CH3)2
CH2-cyclopentyl
CH2O(C6H5)
CH2SCH2CH(CH3)2
CH2NHCH2CH(CH3)2
OCH2CH(CH3)2
NHCH2CH(CH3)2

C6H5
3CF3—C6H4
2Cl—C6H4
R¹ = Br,

R² = CH=CHC(=O)—N(morpholino)

R³
(CH2)3CH3
CH2CH(CH3)2
CH2CH2CH(CH3)2
CH2-cyclopentyl
CH2O(C6H5)
CH2SCH2CH(CH3)2
CH2NHCH2CH(CH3)2
OCH2CH(CH3)2
NHCH2CH(CH3)2
C6H5
3CF3—C6H4
2Cl—C6H4
R¹ = Cl, R² = CH=CHC(=O)—N(morpholino)

R³
(CH2)3CH3
CH2CH(CH3)2
R³
3CF3—C6H4
2Cl—C6H4
R¹ = OCF3,

R² = CH=CHC(=O)—N(morpholino)

R³
(CH2)3CH3
CH2CH2CH(CH3)2
CH2CH2CH(CH3)2
CH2-cyclopentyl
CH2O(C6H5)
CH2SCH2CH(CH3)2
CH2NHCH2CH(CH3)2
OCH2CH(CH3)2
NHCH2CH(CH3)2
C6H5

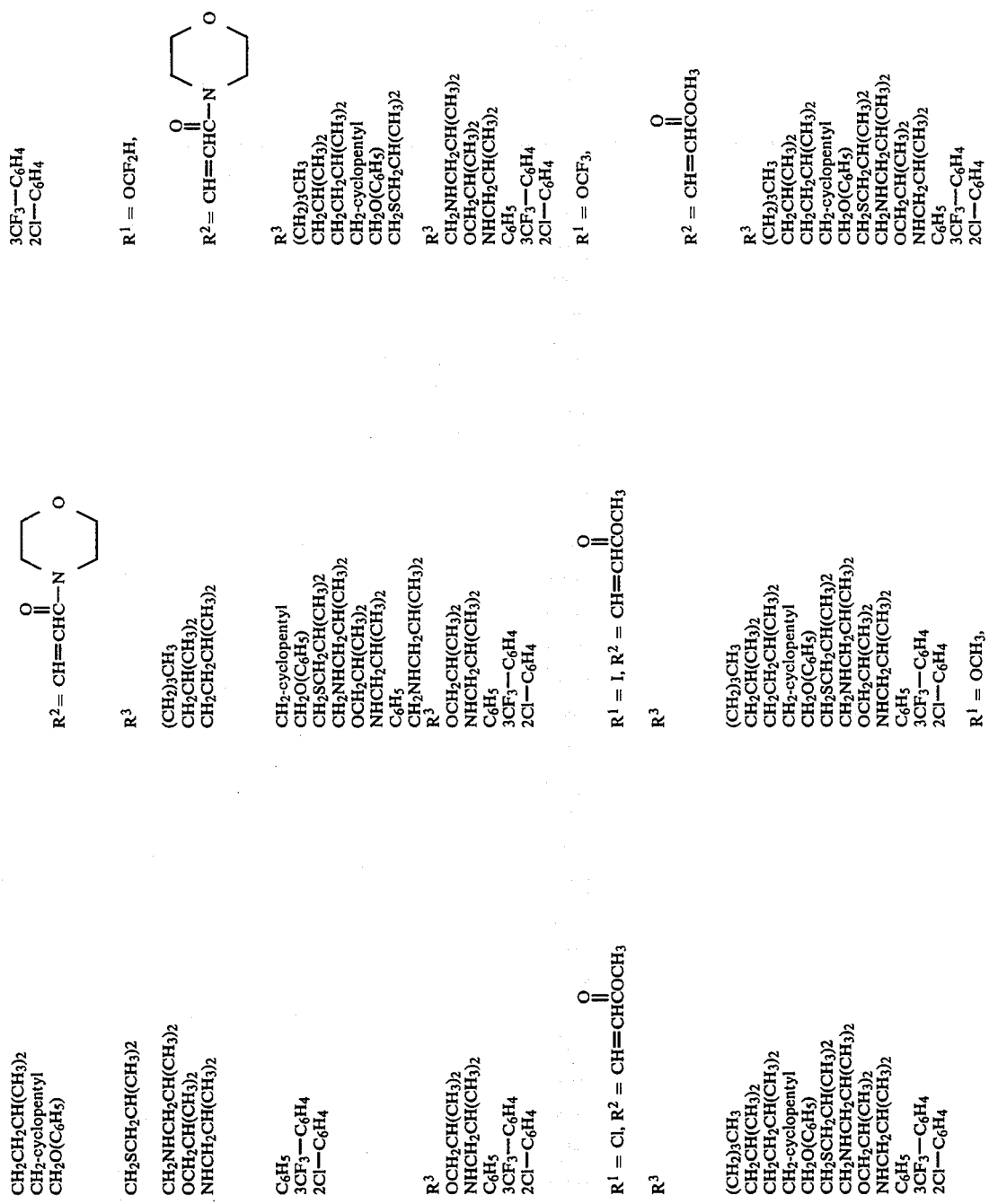

-continued

| | | |
|---|---|---|
| $R^1 = Br, R^2 = CH=CHCOCH_3$ | $R^2 = CH=CHCOCH_3$ | $R^1 = OCF_2H,$ |
| | | $R^2 = CH=CHCOCH_3$ |
| $R^3$ | $R^3$ | $R^3$ |
| $(CH_2)_3CH_3$ | $(CH_2)_3CH_3$ | $(CH_2)_3CH_3$ |
| $CH_2CH(CH_3)_2$ | | $CH_2CH(CH_3)_2$ |
| $CH_2CH_2CH(CH_3)_2$ | | $CH_2CH_2CH(CH_3)_2$ |
| $CH_2$-cyclopentyl | | $CH_2$-cyclopentyl |
| $CH_2SCH_2CH(CH_3)_2$ | | $CH_2O(C_6H_5)$ |
| $CH_2NHCH_2CH(CH_3)_2$ | | $CH_2SCH_2CH(CH_3)_2$ |
| $CH_2O(C_6H_5)$ | | $CH_2NHCH_2CH(CH_3)_2$ |
| $CH_2SCH_2CH(CH_3)_2$ | | $OCH_2CH(CH_3)_2$ |
| $CH_2NHCH_2CH(CH_3)_2$ | | $NHCH_2CH(CH_3)_2$ |
| $OCH_2CH(CH_3)_2$ | | $C_6H_5$ |
| $NHCH_2CH(CH_3)_2$ | | $3CF_3$—$C_6H_4$ |
| $C_6H_5$ | | $2Cl$—$C_6H_4$ |
| $3CF_3$—$C_6H_4$ | | |
| $2Cl$—$C_6H_4$ | | |
| $R^1 = Cl, R^2 = CH=CH_2$ | $R^1 = I, R^2 = CH=CH_2$ | $R^1 = OCF_3, R^2 = CH=CH_2$ |
| $R^3$ | $R^3$ | $R^3$ |
| $(CH_2)_3CH_3$ | $(CH_2)_3CH_3$ | $(CH_2)_3CH_3$ |
| $CH_2CH(CH_3)_2$ | $CH_2CH(CH_3)_2$ | $CH_2CH(CH_3)_2$ |
| $CH_2CH_2CH(CH_3)_2$ | $CH_2CH_2CH(CH_3)_2$ | $CH_2CH_2CH(CH_3)_2$ |
| $CH_2$-cyclopentyl | $CH_2$-cyclopentyl | $CH_2$-cyclopentyl |
| $CH_2O(C_6H_5)$ | $CH_2O(C_6H_5)$ | $CH_2O(C_6H_5)$ |
| $CH_2SCH_2CH(CH_3)_2$ | $CH_2SCH_2CH(CH_3)_2$ | $CH_2SCH_2CH(CH_3)_2$ |
| $CH_2NHCH_2CH(CH_3)_2$ | $CH_2NHCH_2CH(CH_3)_2$ | $CH_2NHCH_2CH(CH_3)_2$ |
| $OCH_2CH(CH_3)_2$ | $OCH_2CH(CH_3)_2$ | $OCH_2CH(CH_3)_2$ |
| $NHCH_2CH(CH_3)_2$ | $NHCH_2CH(CH_3)_2$ | $NHCH_2CH(CH_3)_2$ |
| $C_6H_5$ | $C_6H_5$ | $C_6H_5$ |
| $3CF_3$—$C_6H_4$ | $3CF_3$—$C_6H_4$ | $3CF_3$—$C_6H_4$ |
| $2Cl$—$C_6H_4$ | $2Cl$—$C_6H_4$ | $2Cl$—$C_6H_4$ |
| $R^1 = Br, R^2 = CH=CH_2$ | $R^1 = OCH_3, R^2 = CH=CH_2$ | $R^1 = OCF_2H, R^2 = CH=CH_2$ |
| $R^3$ | $R^3$ | $R^3$ |
| $(CH_2)_3CH_3$ | $(CH_2)_3CH_3$ | $(CH_2)_3CH_3$ |
| $CH_2CH(CH_3)_2$ | $CH_2CH(CH_3)_2$ | $CH_2CH(CH_3)_2$ |
| $CH_2CH_2CH(CH_3)_2$ | $CH_2CH_2CH(CH_3)_2$ | $CH_2CH_2CH(CH_3)_2$ |
| $CH_2$-cyclopentyl | $CH_2$-cyclopentyl | $CH_2$-cyclopentyl |
| $CH_2O(C_6H_5)$ | $CH_2O(C_6H_5)$ | $CH_2O(C_6H_5)$ |
| $CH_2SCH_2CH(CH_3)_2$ | $CH_2SCH_2CH(CH_3)_2$ | $CH_2SCH_2CH(CH_3)_2$ |
| $CH_2NHCH_2CH(CH_3)_2$ | $CH_2NHCH_2CH(CH_3)_2$ | $CH_2NHCH_2CH(CH_3)_2$ |
| $OCH_2CH(CH_3)_2$ | $OCH_2CH(CH_3)_2$ | $OCH_2CH(CH_3)_2$ |
| $NHCH_2CH(CH_3)_2$ | $NHCH_2CH(CH_3)_2$ | $NHCH_2CH(CH_3)_2$ |
| $C_6H_5$ | $C_6H_5$ | $C_6H_5$ |
| $3CF_3$—$C_6H_4$ | | |
| $2Cl$—$C_6H_4$ | | |

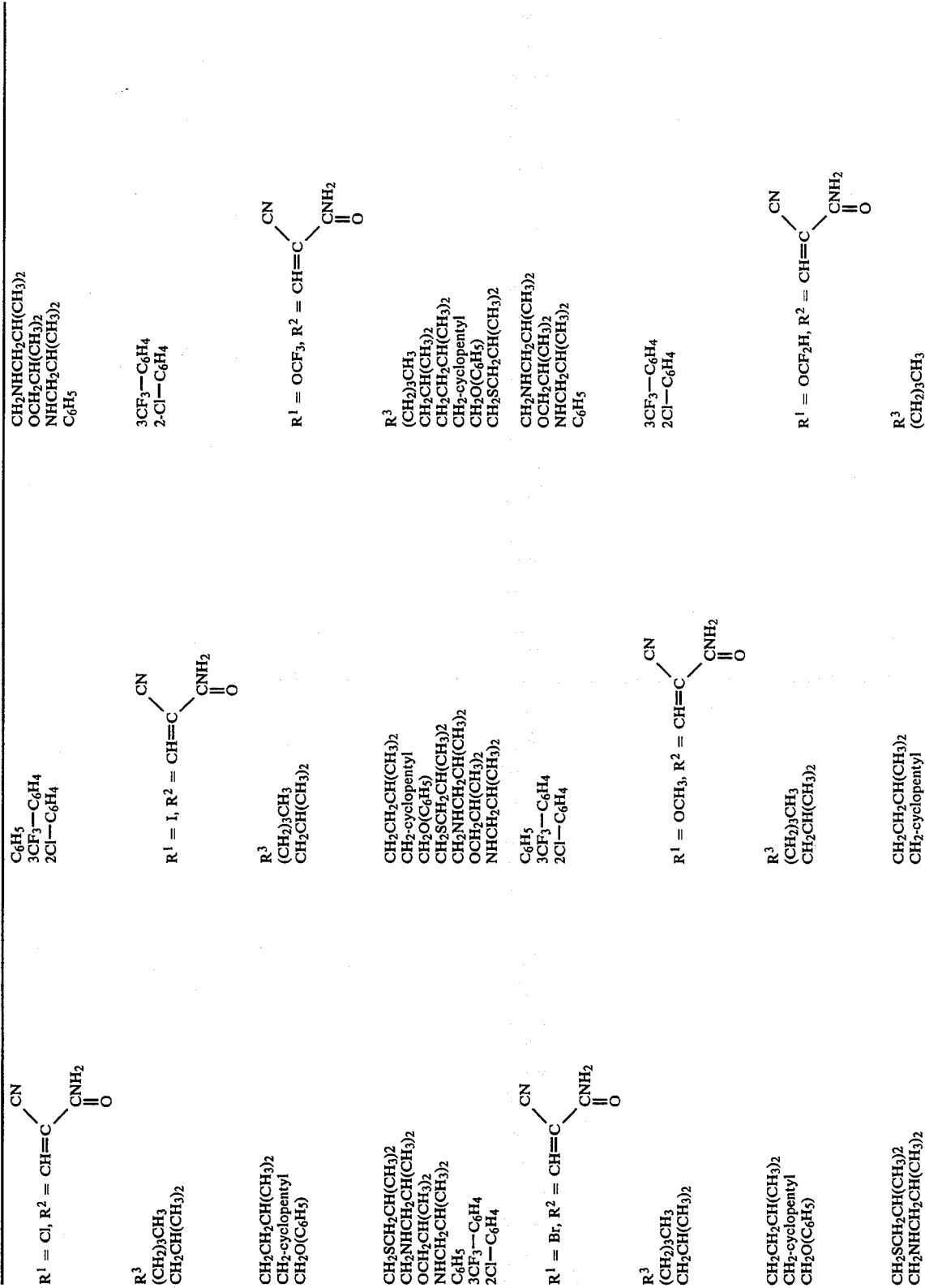

-continued

| R³ | | |
|---|---|---|
| | $R^1 = Cl, R^2 = CH=C(CN)_2$ | $R^1 = Br, R^2 = CH=C(CN)_2$ | $R^1 = OCH_3, R^2 = CH=C(CN)_2$ |
| CH$_2$CH(CH$_3$)$_2$ | | | |
| CH$_2$CH$_2$CH(CH$_3$)$_2$ | | | |
| CH$_2$-cyclopentyl | | | |
| CH$_2$O(C$_6$H$_5$) | | | |
| CH$_2$SCH$_2$CH(CH$_3$)$_2$ | | | |
| CH$_2$NHCH$_2$CH(CH$_3$)$_2$ | | | |
| OCH$_2$CH(CH$_3$)$_2$ | | | |
| NHCH$_2$CH(CH$_3$)$_2$ | | | |
| C$_6$H$_5$ | | | |
| 3CF$_3$—C$_6$H$_4$ | | | |
| 2Cl—C$_6$H$_4$ | | | |

| | $R^1 = OCF_2H, R^2 = CH=C(CN)_2$ | $R^1 = I, R^2 = CH=C(CN)_2$ | $R^1 = OCF_3, R^2 = CH=C(CN)_2$ |
|---|---|---|---|
| R³ | | R³ | R³ |
| (CH$_2$)$_3$CH$_3$ | | (CH$_2$)$_3$CH$_3$ | (CH$_2$)$_3$CH$_3$ |
| CH$_2$CH(CH$_3$)$_2$ | | CH$_2$CH(CH$_3$)$_2$ | CH$_2$CH(CH$_3$)$_2$ |
| CH$_2$CH$_2$CH(CH$_3$)$_2$ | | CH$_2$CH$_2$CH(CH$_3$)$_2$ | CH$_2$CH$_2$CH(CH$_3$)$_2$ |
| CH$_2$-cyclopentyl | | CH$_2$-cyclopentyl | CH$_2$-cyclopentyl |
| CH$_2$O(C$_6$H$_5$) | | CH$_2$O(C$_6$H$_5$) | CH$_2$O(C$_6$H$_5$) |
| CH$_2$SCH$_2$CH(CH$_3$)$_2$ | | CH$_2$SCH$_2$CH(CH$_3$)$_2$ | CH$_2$SCH$_2$CH(CH$_3$)$_2$ |
| CH$_2$NHCH$_2$CH(CH$_3$)$_2$ | | CH$_2$NHCH$_2$CH(CH$_3$)$_2$ | CH$_2$NHCH$_2$CH(CH$_3$)$_2$ |
| OCH$_2$CH(CH$_3$)$_2$ | | OCH$_2$CH(CH$_3$)$_2$ | OCH$_2$CH(CH$_3$)$_2$ |
| NHCH$_2$CH(CH$_3$)$_2$ | | NHCH$_2$CH(CH$_3$)$_2$ | NHCH$_2$CH(CH$_3$)$_2$ |
| C$_6$H$_5$ | | C$_6$H$_5$ | C$_6$H$_5$ |
| 3CF$_3$—C$_6$H$_4$ | | 3CF$_3$—C$_6$H$_4$ | 3CF$_3$—C$_6$H$_4$ |
| 2Cl—C$_6$H$_4$ | | 2Cl—C$_6$H$_4$ | 2Cl—C$_6$H$_4$ |
| | | $R^1 = Br,$ | $R^1 = OCH_3,$ |
| | | $R^2 = \overset{\overset{O}{\|}}{C}-NH-OCH_2CH=CH_2$ | $R^2 = \overset{\overset{O}{\|}}{C}-NH-OCH_2CH=CH_2$ |
| | | R³ | R³ |
| | | (CH$_2$)$_3$CH$_3$ | (CH$_2$)$_3$CH$_3$ |

-continued

| | | |
|---|---|---|
| CH$_2$CH(CH$_3$)$_2$ | | CH$_2$CH(CH$_3$)$_2$ |
| CH$_2$-cyclopentyl | | CH$_2$CH$_2$CH(CH$_3$)$_2$ |
| CH$_2$O(C$_6$H$_5$) | | CH$_2$-cyclopentyl |
| CH$_2$SCH$_2$CH(CH$_3$)$_2$ | | CH$_2$O(C$_6$H$_5$) |
| CH$_2$NHCH$_2$CH(CH$_3$)$_2$ | | CH$_2$SCH$_2$CH(CH$_3$)$_2$ |
| OCH$_2$CH(CH$_3$)$_2$ | | CH$_2$NHCH$_2$CH(CH$_3$)$_2$ |
| NHCH$_2$CH(CH$_3$)$_2$ | | OCH$_2$CH(CH$_3$)$_2$ |
| C$_6$H$_5$ | | NHCH$_2$CH(CH$_3$)$_2$ |
| 3CF$_3$—C$_6$H$_4$ | | C$_6$H$_5$ |
| 2Cl—C$_6$H$_4$ | | 3CF$_3$—C$_6$H$_4$ |
| R$^1$ = Cl, | | 2Cl—C$_6$H$_4$ |
| R$^2$ = C(=O)—NH—OCH$_2$CH=CH$_2$ | | R$^1$ = OCF$_3$, |
| | | R$^2$ = C(=O)—NH—OCH$_2$CH=CH$_2$ |
| R$^3$ | | R$^3$ |
| (CH$_2$)$_3$CH$_3$ | | (CH$_2$)$_3$CH$_3$ |
| CH$_2$CH(CH$_3$)$_2$ | | CH$_2$CH(CH$_3$)$_2$ |
| CH$_2$CH$_2$CH(CH$_3$)$_2$ | | CH$_2$CH$_2$CH(CH$_3$)$_2$ |
| CH$_2$-cyclopentyl | | CH$_2$-cyclopentyl |
| CH$_2$O(C$_6$H$_5$) | | CH$_2$O(C$_6$H$_5$) |
| CH$_2$SCH$_2$CH(CH$_3$)$_2$ | | CH$_2$SCH$_2$CH(CH$_3$)$_2$ |
| CH$_2$NHCH$_2$CH(CH$_3$)$_2$ | | CH$_2$NHCH$_2$CH(CH$_3$)$_2$ |
| OCH$_2$CH(CH$_3$)$_2$ | | OCH$_2$CH(CH$_3$)$_2$ |
| NHCH$_2$CH(CH$_3$)$_2$ | | NHCH$_2$CH(CH$_3$)$_2$ |
| C$_6$H$_5$ | | C$_6$H$_5$ |
| 3CF$_3$—C$_6$H$_4$ | | 3CF$_3$—C$_6$H$_4$ |
| 2Cl—C$_6$H$_4$ | | 2Cl—C$_6$H$_4$ |
| R$^3$ | | R$^3$ |
| C$_6$H$_5$ | | C$_6$H$_5$ |
| 3CF$_3$—C$_6$H$_4$ | | 3CF$_3$—C$_6$H$_4$ |
| 2Cl—C$_6$H$_4$ | | 2Cl—C$_6$H$_4$ |
| R$^1$ = OCF$_2$H, | | R$^1$ = OCH$_3$, R$^2$ = C(=O)NH—OCH$_3$ |
| R$^2$ = C(=O)—NH—OCH$_2$CH=CH$_2$ | | R$^3$ |
| R$^3$ | | (CH$_2$)$_3$CH$_3$ |
| (CH$_2$)$_3$CH$_3$ | | CH$_2$CH(CH$_3$)$_2$ |
| CH$_2$CH(CH$_3$)$_2$ | | CH$_2$CH$_2$CH(CH$_3$)$_2$ |
| CH$_2$CH$_2$CH(CH$_3$)$_2$ | | CH$_2$-cyclopentyl |
| CH$_2$-cyclopentyl | | CH$_2$O(C$_6$H$_5$) |
| CH$_2$O(C$_6$H$_5$) | | CH$_2$SCH$_2$CH(CH$_3$)$_2$ |
| CH$_2$SCH$_2$CH(CH$_3$)$_2$ | | CH$_2$NHCH$_2$CH(CH$_3$)$_2$ |
| CH$_2$NHCH$_2$CH(CH$_3$)$_2$ | | OCH$_2$CH(CH$_3$)$_2$ |
| OCH$_2$CH(CH$_3$)$_2$ | | NHCH$_2$CH(CH$_3$)$_2$ |
| NHCH$_2$CH(CH$_3$)$_2$ | | C$_6$H$_5$ |
| C$_6$H$_5$ | | 3CF$_3$—C$_6$H$_4$ |
| 3CF$_3$—C$_6$H$_4$ | | 2Cl—C$_6$H$_4$ |
| 2Cl—C$_6$H$_4$ | | |

-continued

| $R^1 = Cl, R^2 = \overset{O}{\underset{\|}{C}}NH-OCH_3$ | $R^1 = I, R^2 = \overset{O}{\underset{\|}{C}}NH-OCH_3$ | $R^1 = OCF_3, R^2 = \overset{O}{\underset{\|}{C}}NH-OCH_3$ |
|---|---|---|
| $R^3$ | $R^3$ | $R^3$ |
| $(CH_2)_3CH_3$ | $(CH_2)_3CH_3$ | $(CH_2)_3CH_3$ |
| $CH_2CH(CH_3)_2$ | $CH_2CH(CH_3)_2$ | $CH_2CH(CH_3)_2$ |
| $CH_2CH_2CH(CH_3)_2$ | $CH_2CH_2CH(CH_3)_2$ | $CH_2CH_2CH(CH_3)_2$ |
| $CH_2$-cyclopentyl | $CH_2$-cyclopentyl | $CH_2$-cyclopentyl |
| $CH_2O(C_6H_5)$ | $CH_2O(C_6H_5)$ | $CH_2O(C_6H_5)$ |
| $CH_2SCH_2CH(CH_3)_2$ | $CH_2SCH_2CH(CH_3)_2$ | $CH_2SCH_2CH(CH_3)_2$ |
| $CH_2NHCH_2CH(CH_3)_2$ | $CH_2NHCH_2CH(CH_3)_2$ | $CH_2NHCH_2CH(CH_3)_2$ |
| $OCH_2CH(CH_3)_2$ | $OCH_2CH(CH_3)_2$ | $OCH_2CH(CH_3)_2$ |
| $NHCH_2CH(CH_3)_2$ | $NHCH_2CH(CH_3)_2$ | $NHCH_2CH(CH_3)_2$ |
| $R^3$ | $R^3$ | $R^3$ |
| $C_6H_5$ | $C_6H_5$ | $C_6H_5$ |
| $3CF_3-C_6H_4$ | $3CF_3-C_6H_4$ | $3CF_3-C_6H_4$ |
| $2Cl-C_6H_4$ | $2Cl-C_6H_4$ | $2Cl-C_6H_4$ |
| $R^1 = OCF_2H, R^2 = \overset{O}{\underset{\|}{C}}NH-OCH_3$ | $R^1 = Br, R^2 = \overset{O}{\underset{\|}{C}}NHCH_2-\triangleleft$ | $R^1 = OCH_3,$ $R^2 = \overset{O}{\underset{\|}{C}}NHCH_2-\triangleleft$ |
| $R^3$ | $R^3$ | $R^3$ |
| $(CH_2)_3CH_3$ | $(CH_2)_3CH_3$ | $(CH_2)_3CH_3$ |
|  |  | $CH_2CH(CH_3)_2$ |
|  |  | $CH_2CH_2CH(CH_3)_2$ |
|  |  | $CH_2$-cyclopentyl |
|  |  | $CH_2O(C_6H_5)$ |
|  |  | $CH_2SCH_2CH(CH_3)_2$ |
|  |  | $CH_2NHCH_2CH(CH_3)_2$ |
|  |  | $OCH_2CH(CH_3)_2$ |
|  |  | $NHCH_2CH(CH_3)_2$ |
|  |  | $C_6H_5$ |
|  |  | $3CF_3-C_6H_4$ |
|  |  | $2Cl-C_6H_4$ |
| $R^1 = Cl, R^2 = \overset{O}{\underset{\|}{C}}NHCH_2-\triangleleft$ | $R^1 = I, R^2 = \overset{O}{\underset{\|}{C}}NHCH_2-\triangleleft$ | $R^1 = OCF_3,$ $R^2 = \overset{O}{\underset{\|}{C}}NHCH_2-\triangleleft$ |
| $R^3$ | $R^3$ | $R^3$ |
| $(CH_2)_3CH_3$ | $(CH_2)_3CH_3$ | $(CH_2)_3CH_3$ |
| $CH_2CH(CH_3)_2$ | $CH_2CH(CH_3)_2$ |  |
| $CH_2CH_2CH(CH_3)_2$ | $CH_2CH_2CH(CH_3)_2$ |  |
| $CH_2$-cyclopentyl |  |  |
| $CH_2O(C_6H_5)$ |  |  |

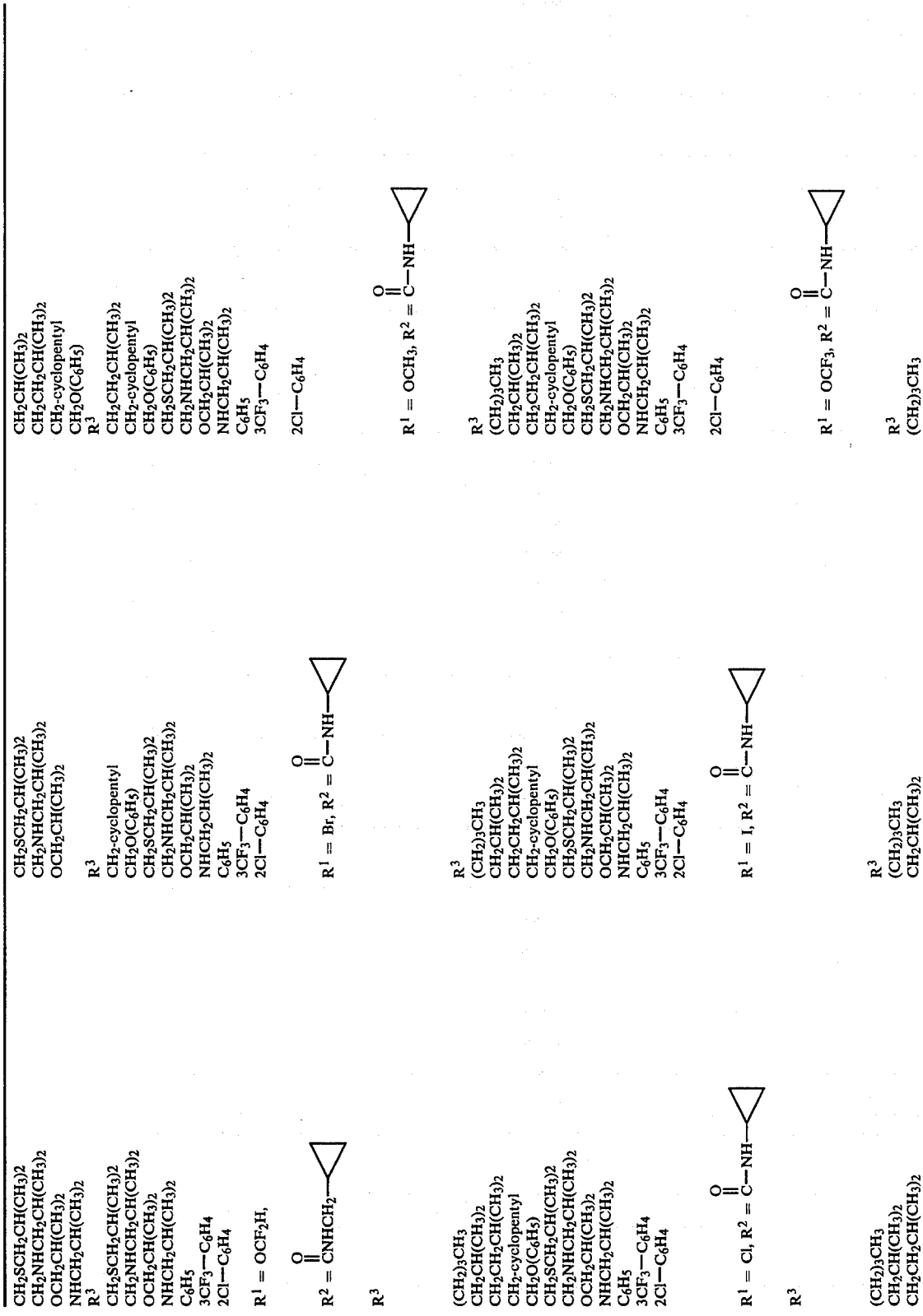

-continued

| $R^3$ | $R^1 = Cl, R^2 = \overset{O}{\underset{\|}{C}}N(CH_3)_2$ | $R^1 = I, R^2 = \overset{O}{\underset{\|}{C}}N(CH_3)_2$ |
|---|---|---|
| $CH_2CH(CH_3)_2$ | | |
| | $R^3$ | $R^3$ |
| | $(CH_2)_3CH_3$ | $(CH_2)_3CH_3$ |
| $CH_2CH_2CH(CH_3)_2$ | $CH_2CH(CH_3)_2$ | $CH_2CH(CH_3)_2$ |
| $CH_2$-cyclopentyl | $CH_2CH_2CH(CH_3)_2$ | $CH_2CH_2CH(CH_3)_2$ |
| $CH_2O(C_6H_5)$ | $CH_2$-cyclopentyl | $CH_2$-cyclopentyl |
| $CH_2SCH_2CH(CH_3)_2$ | $CH_2O(C_6H_5)$ | $CH_2O(C_6H_5)$ |
| $CH_2NHCH_2CH(CH_3)_2$ | $CH_2SCH_2CH(CH_3)_2$ | $CH_2SCH_2CH(CH_3)_2$ |
| $OCH_2CH(CH_3)_2$ | $CH_2NHCH_2CH(CH_3)_2$ | $CH_2NHCH_2CH(CH_3)_2$ |
| $NHCH_2CH(CH_3)_2$ | $OCH_2CH(CH_3)_2$ | $OCH_2CH(CH_3)_2$ |
| $C_6H_5$ | $NHCH_2CH(CH_3)_2$ | $NHCH_2CH(CH_3)_2$ |
| $3CF_3$—$C_6H_4$ | $C_6H_5$ | $C_6H_5$ |
| $2Cl$—$C_6H_4$ | $3CF_3$—$C_6H_4$ | $3CF_3$—$C_6H_4$ |
| $R^1 = OCF_2H,$ | $2Cl$—$C_6H_4$ | $2Cl$—$C_6H_4$ |
| $R^2 = \overset{O}{\underset{\|}{C}}-NH-\triangleleft$ | $R^1 = Br, R^2 = \overset{O}{\underset{\|}{C}}N(CH_3)_2$ | $R^1 = OCH_3, R^2 = \overset{O}{\underset{\|}{C}}N(CH_3)_2$ |
| $R^3$ | $R^3$ | $R^3$ |
| $(CH_2)_3CH_3$ | $(CH_2)_3CH_3$ | $(CH_2)_3CH_3$ |
| $CH_2CH(CH_3)_2$ | $CH_2CH(CH_3)_2$ | $CH_2CH(CH_3)_2$ |
| $CH_2CH_2CH(CH_3)_2$ | $CH_2CH_2CH(CH_3)_2$ | $CH_2CH_2CH(CH_3)_2$ |
| $CH_2$-cyclopentyl | $CH_2$-cyclopentyl | $CH_2$-cyclopentyl |
| $CH_2O(C_6H_5)$ | $CH_2O(C_6H_5)$ | $CH_2O(C_6H_5)$ |
| $CH_2SCH_2CH(CH_3)_2$ | $CH_2SCH_2CH(CH_3)_2$ | $CH_2SCH_2CH(CH_3)_2$ |
| $CH_2NHCH_2CH(CH_3)_2$ | $CH_2NHCH_2CH(CH_3)_2$ | $CH_2NHCH_2CH(CH_3)_2$ |
| $OCH_2CH(CH_3)_2$ | $OCH_2CH(CH_3)_2$ | $OCH_2CH(CH_3)_2$ |
| $NHCH_2CH(CH_3)_2$ | $NHCH_2CH(CH_3)_2$ | $NHCH_2CH(CH_3)_2$ |
| $C_6H_5$ | $C_6H_5$ | $C_6H_5$ |
| $3CF_3$—$C_6H_4$ | $3CF_3$—$C_6H_4$ | $3CF_3$—$C_6H_4$ |
| $2Cl$—$C_6H_4$ | $2Cl$—$C_6H_4$ | $2Cl$—$C_6H_4$ |

| $R^1 = OCF_3, R^2 = C(=O)N(CH_3)_2$ | $R^1 = Cl, R^2 = C(=S)NHCH_3$ | $R^1 = I, R^2 = C(=S)NHCH_3$ |
|---|---|---|
| $R^3$ | $R^3$ | $R^3$ |
| $(CH_2)_3CH_3$ | $(CH_2)_3CH_3$ | $(CH_2)_3CH_3$ |
| $CH_2CH(CH_3)_2$ | $CH_2CH(CH_3)_2$ | $CH_2CH(CH_3)_2$ |
| $CH_2CH_2CH(CH_3)_2$ | $CH_2CH_2CH(CH_3)_2$ | $CH_2CH_2CH(CH_3)_2$ |
| $CH_2$-cyclopentyl | $CH_2$-cyclopentyl | $CH_2$-cyclopentyl |
| $CH_2O(C_6H_5)$ | $CH_2O(C_6H_5)$ | $CH_2O(C_6H_5)$ |
| $CH_2SCH_2CH(CH_3)_2$ | $CH_2SCH_2CH(CH_3)_2$ | $CH_2SCH_2CH(CH_3)_2$ |
| $CH_2NHCH_2CH(CH_3)_2$ | $CH_2NHCH_2CH(CH_3)_2$ | $CH_2NHCH_2CH(CH_3)_2$ |
| $OCH_2CH(CH_3)_2$ | $OCH_2CH(CH_3)_2$ | $OCH_2CH(CH_3)_2$ |
| $NHCH_2CH(CH_3)_2$ | $NHCH_2CH(CH_3)_2$ | $NHCH_2CH(CH_3)_2$ |
| $C_6H_5$ | $C_6H_5$ | $C_6H_5$ |
| $3CF_3$—$C_6H_4$ | $3CF_3$—$C_6H_4$ | $3CF_3$—$C_6H_4$ |
| $2Cl$—$C_6H_4$ | $2Cl$—$C_6H_4$ | $2Cl$—$C_6H_4$ |

| $R^1 = OCF_2H, R^2 = C(=O)N(CH_3)_2$ | $R^1 = Br, R^2 = C(=S)NHCH_3$ | $R^1 = OCH_3, R^2 = C(=S)NHCH_3$ |
|---|---|---|
| $R^3$ | $R^3$ | $R^3$ |
| $(CH_2)_3CH_3$ | $(CH_2)_3CH_3$ | $(CH_2)_3CH_3$ |
| $CH_2CH(CH_3)_2$ | $CH_2CH(CH_3)_2$ | $CH_2CH(CH_3)_2$ |
| $CH_2CH_2CH(CH_3)_2$ | $CH_2CH_2CH(CH_3)_2$ | $CH_2CH_2CH(CH_3)_2$ |
| $CH_2$-cyclopentyl | $CH_2$-cyclopentyl | $CH_2$-cyclopentyl |
| $CH_2O(C_6H_5)$ | $CH_2O(C_6H_5)$ | $CH_2O(C_6H_5)$ |
| $CH_2SCH_2CH(CH_3)_2$ | $CH_2SCH_2CH(CH_3)_2$ | $CH_2SCH_2CH(CH_3)_2$ |
| $CH_2NHCH_2CH(CH_3)_2$ | $CH_2NHCH_2CH(CH_3)_2$ | $CH_2NHCH_2CH(CH_3)_2$ |
| $OCH_2CH(CH_3)_2$ | $OCH_2CH(CH_3)_2$ | $OCH_2CH(CH_3)_2$ |
| $NHCH_2CH(CH_3)_2$ | $NHCH_2CH(CH_3)_2$ | $NHCH_2CH(CH_3)_2$ |
| $C_6H_5$ | $C_6H_5$ | $C_6H_5$ |
| $3CF_3$—$C_6H_4$ | $3CF_3$—$C_6H_4$ | $3CF_3$—$C_6H_4$ |
| $2Cl$—$C_6H_4$ | $2Cl$—$C_6H_4$ | $2Cl$—$C_6H_4$ |

| $R^1 = OCF_3, R^2 = C(=S)NHCH_3$ | $R^1 = Cl,\ R^2 = C(=O)\text{—NH—}(3\text{-}CF_3\text{-}C_6H_4)$ | $R^3$ |
|---|---|---|
| $R^3$ | | $2Cl$—$C_6H_4$ |
| $(CH_2)_3CH_3$ | | $R^1 = I,$ |

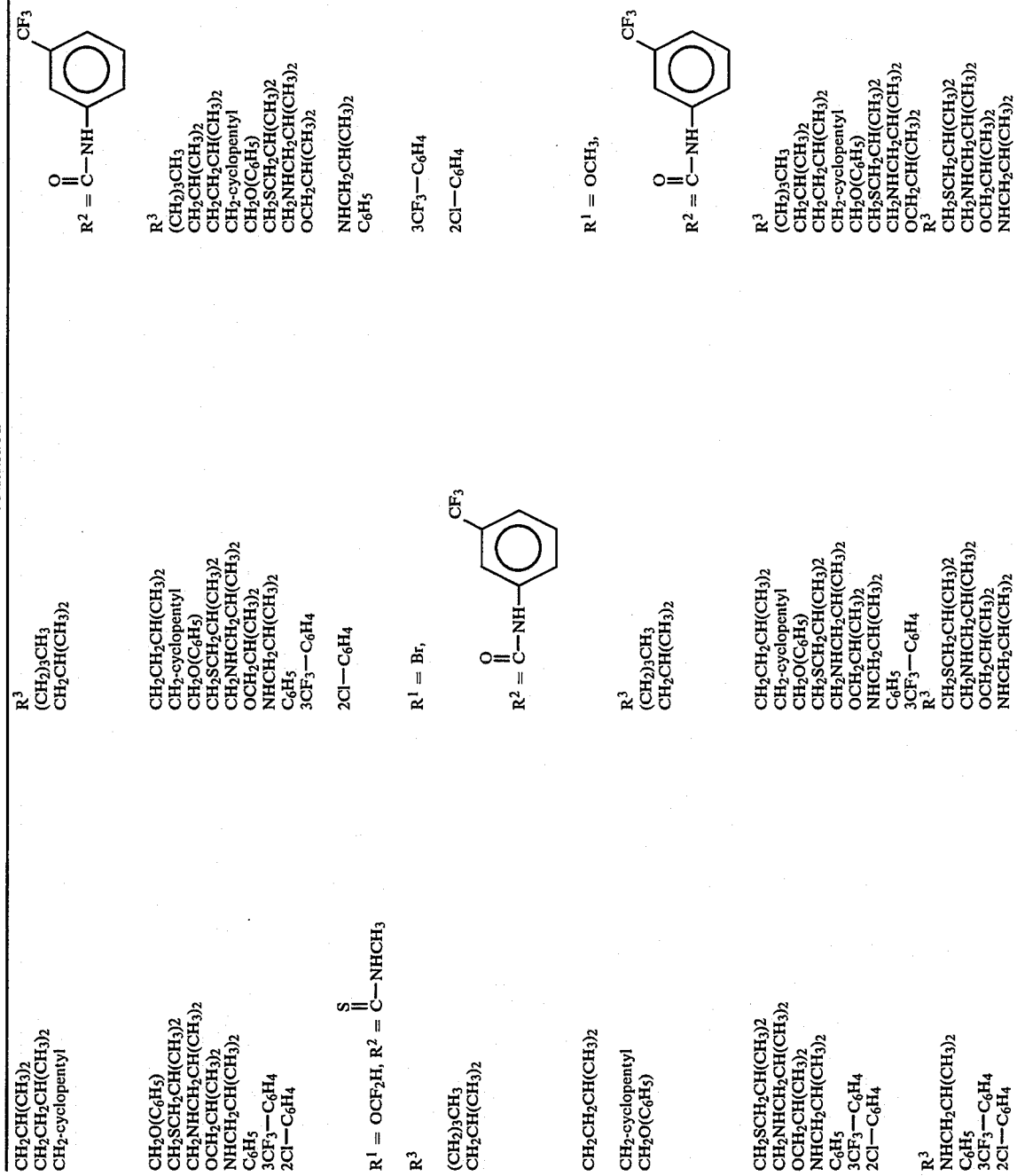

-continued

| | | |
|---|---|---|
| $R^1 = OCF_3$, | | C$_6$H$_5$ |
| | | 3CF$_3$—C$_6$H$_4$ |
| | | 2Cl—C$_6$H$_4$ |

$R^2 = \overset{\overset{O}{\|}}{C}-NH-\phantom{}$<br>(3-CF$_3$-C$_6$H$_4$)

$R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = OCF_2H$, $R^2 = \overset{\overset{O}{\|}}{C}-NH-\phantom{}$(3-CF$_3$-C$_6$H$_4$)

$R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
$R^3$
CH$_2$O(C$_6$H$_5$)
CH$_2$SCH$_2$CH(CH$_3$)$_2$ CH$_2$NHCH$_2$CH(CH$_3$)$_2$
OCH$_2$CH(CH$_3$)$_2$
NHCH$_2$CH(CH$_3$)$_2$
C$_6$H$_5$ $R^1 = Cl, R^2 = \overset{\overset{O}{\|}}{C}-NH-C_6H_5$ $R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = Br, R^2 = \overset{\overset{O}{\|}}{C}-NH-C_6H_5$ $R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)

$R^1 = I, R^2 = \overset{\overset{O}{\|}}{C}-NH-C_6H_5$ $R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = OCH_3, R^2 = \overset{\overset{O}{\|}}{C}-NH-C_6H_5$ $R^3$
(CH$_2$)$_3$CH$_3$
CH$_2$CH(CH$_3$)$_2$
CH$_2$CH$_2$CH(CH$_3$)$_2$
CH$_2$-cyclopentyl
$R^1 = Br,$ $R^2 = \overset{\overset{O}{\|}}{C}-NH-CH_2CH_3$ $R^3$
(CH$_2$)$_3$CH$_3$
CH$_2$CH(CH$_3$)$_2$
CH$_2$CH$_2$CH(CH$_3$)$_2$ -continued

| | | |
|---|---|---|
| 3CF$_3$—C$_6$H$_4$ | OCH$_2$CH(CH$_3$)$_2$ | CH$_2$-cyclopentyl |
| 2Cl—C$_6$H$_4$ | NHCH$_2$CH(CH$_3$)$_2$ | CH$_2$O(C$_6$H$_5$) |
| R$^1$ = OCF$_3$, | C$_6$H$_5$ | CH$_2$SCH$_2$CH(CH$_3$)$_2$ |
| | 3CF$_3$—C$_6$H$_4$ | CH$_2$NHCH$_2$CH(CH$_3$)$_2$ |
| $R^2 = \overset{\overset{\displaystyle O}{\|}}{C}-NH-$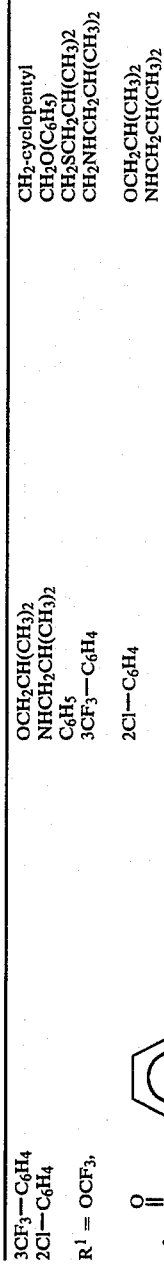 | 2Cl—C$_6$H$_4$ | OCH$_2$CH(CH$_3$)$_2$ |
| | | NHCH$_2$CH(CH$_3$)$_2$ |
| R$^3$ | R$^1$ = Cl, | C$_6$H$_5$ |
| (CH$_2$)$_3$CH$_3$ | $R^2 = \overset{\overset{\displaystyle O}{\|}}{C}-NH-CH_2CH_3$ | 3CF$_3$—C$_6$H$_4$ |
| CH$_2$CH(CH$_3$)$_2$ | | 2Cl—C$_6$H$_4$ |
| CH$_2$CH$_2$CH(CH$_3$)$_2$ | R$^3$ | R$^1$ = I, |
| CH$_2$-cyclopentyl | (CH$_2$)$_3$CH$_3$ | |
| CH$_2$O(C$_6$H$_5$) | CH$_2$CH(CH$_3$)$_2$ | $R^2 = \overset{\overset{\displaystyle O}{\|}}{C}-NH-CH_2CH_3$ |
| CH$_2$SCH$_2$CH(CH$_3$)$_2$ | CH$_2$CH$_2$CH(CH$_3$)$_2$ | |
| CH$_2$NHCH$_2$CH(CH$_3$)$_2$ | CH$_2$-cyclopentyl | R$^3$ |
| OCH$_2$CH(CH$_3$)$_2$ | CH$_2$O(C$_6$H$_5$) | (CH$_2$)$_3$CH$_3$ |
| NHCH$_2$CH(CH$_3$)$_2$ | CH$_2$SCH$_2$CH(CH$_3$)$_2$ | CH$_2$CH(CH$_3$)$_2$ |
| C$_6$H$_5$ | CH$_2$NHCH$_2$CH(CH$_3$)$_2$ | CH$_2$CH$_2$CH(CH$_3$)$_2$ |
| 3CF$_3$—C$_6$H$_4$ | OCH$_2$CH(CH$_3$)$_2$ | CH$_2$-cyclopentyl |
| 2Cl—C$_6$H$_4$ | NHCH$_2$CH(CH$_3$)$_2$ | CH$_2$O(C$_6$H$_5$) |
| R$^1$ = OCF$_2$H, | C$_6$H$_5$ | CH$_2$SCH$_2$CH(CH$_3$)$_2$ |
| | 3CF$_3$—C$_6$H$_4$ | |
| $R^2 = \overset{\overset{\displaystyle O}{\|}}{C}-NH-$ | 2Cl—C$_6$H$_4$ | OCH$_2$CH(CH$_3$)$_2$ |
| | | NHCH$_2$CH(CH$_3$)$_2$ |
| R$^3$ | R$^1$ = OCF$_2$H, | C$_6$H$_5$ |
| (CH$_2$)$_3$CH$_3$ | | 3CF$_3$—C$_6$H$_4$ |
| R$^1$ = OCH$_3$, | $R^2 = \overset{\overset{\displaystyle O}{\|}}{C}-NH-CH_2CH_3$ | 2Cl—C$_6$H$_4$ |
| | | R$^1$ = OCF$_2$H, |
| $R^2 = \overset{\overset{\displaystyle O}{\|}}{C}-NH-CH_2CH_3$ | R$^3$ | $R^2 = \overset{\overset{\displaystyle O}{\|}}{C}-NH-CH_2CH_3$ |
| | (CH$_2$)$_3$CH$_3$ | |
| R$^3$ | CH$_2$CH(CH$_3$)$_2$ | R$^3$ |
| (CH$_2$)$_3$CH$_3$ | CH$_2$CH$_2$CH(CH$_3$)$_2$ | (CH$_2$)$_3$CH$_3$ |
| CH$_2$CH(CH$_3$)$_2$ | CH$_2$-cyclopentyl | CH$_2$CH(CH$_3$)$_2$ |
| CH$_2$CH$_2$CH(CH$_3$)$_2$ | CH$_2$O(C$_6$H$_5$) | CH$_2$CH$_2$CH(CH$_3$)$_2$ |
| CH$_2$-cyclopentyl | CH$_2$SCH$_2$CH(CH$_3$)$_2$ | CH$_2$-cyclopentyl |
| CH$_2$O(C$_6$H$_5$) | | CH$_2$O(C$_6$H$_5$) |
| CH$_2$SCH$_2$CH(CH$_3$)$_2$ | | CH$_2$SCH$_2$CH(CH$_3$)$_2$ |

-continued

| |
|---|
| CH$_2$NHCH$_2$CH(CH$_3$)$_2$ |
| OCH$_2$CH(CH$_3$)$_2$ |
| NHCH$_2$CH(CH$_3$)$_2$ |
| C$_6$H$_5$ |
| 3CF$_3$—C$_6$H$_4$ |
| 2Cl—C$_6$H$_4$ |

TABLE 2

$R^1 = Cl, R^2 = CN$
$R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)2
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = Br, R^2 = CN$
$R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)2
CH$_2$NHCH$_2$CH(CH$_3$)$_2$
OCH$_2$CH(CH$_3$)$_2$
NHCH$_2$CH(CH$_3$)$_2$ $R^1 = OCF_3, R^2 = CN$
$R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)2
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = OCF_2H, R^2 = CN$
$R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)2
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = Cl, R^2 = \overset{O}{\underset{\|}{C}}NH_2$
$R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)2
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = Br, R^2 = \overset{O}{\underset{\|}{C}}NH_2$
$R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)2
CH$_2$NHCH$_2$CH(CH$_3$)$_2$
OCH$_2$CH(CH$_3$)$_2$
NHCH$_2$CH(CH$_3$)$_2$
3CF$_3$—C$_6$H$_4$
2Cl—C$_6$H$_4$ $R^1 = OCF_3, R^2 = \overset{O}{\underset{\|}{C}}NH_2$
$R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)2
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = OCF_3H, R^2 = \overset{O}{\underset{\|}{C}}NH_2$
$R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)2
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = Cl, R^2 = C\equiv CH$
$R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)2
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = Br, R^2 = C\equiv CH$
$R^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)2
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = OCF_3, R^2 = C\equiv CH$
$R^3$
(CH$_2$)$_3$CH$_3$
CH$_2$CH(CH$_3$)$_2$
CH$_2$CH$_2$CH(CH$_3$)$_2$ TABLE 2-continued CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ R$^1$ = OCF$_2$H, R$^2$ = C≡CH
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $$R^1 = Cl, R^2 = \overset{O}{\overset{\|}{C}}OH$$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$ $$R^1 = Br, R^2 = \overset{O}{\overset{\|}{C}}OH$$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$ $$R^1 = OCF_3, R^2 = \overset{O}{\overset{\|}{C}}OH$$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$ $$R^1 = OCF_2H, R^2 = \overset{O}{\overset{\|}{C}}OH$$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ TABLE 2-continued $$R^1 = Cl, R^2 = \overset{O}{\overset{\|}{C}}OCH_3$$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$ $$R^1 = Br, R^2 = \overset{O}{\overset{\|}{C}}OCH_3$$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$ $$R^1 = OCF_3, R^2 = \overset{O}{\overset{\|}{C}}OCH_3$$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $$R^1 = OCF_2H, R^2 = \overset{O}{\overset{\|}{C}}OCH_3$$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $$R^1 = Cl, R^2 = \overset{O}{\overset{\|}{C}}H$$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
CH$_2$NHCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $$R^1 = Br, R^2 = \overset{O}{\overset{\|}{C}}H$$

TABLE 2-continued $R^3$
$(CH_2)_3CH_3$
$CH_2CH(CH_3)_2$
$CH_2CH_2CH(CH_3)_2$
$CH_2$-cyclopentyl
$CH_2O(C_6H_5)$
$CH_2SCH_2CH(CH_3)2$
$CH_2NHCH_2CH(CH_3)_2$
$OCH_2CH(CH_3)_2$
$NHCH_2CH(CH_3)_2$
$C_6H_5$
$3CF_3-C_6H_4$
$2Cl-C_6H_4$ $R^1 = OCF_3, R^2 = \overset{O}{\overset{\|}{C}}H$
$R^3$
$(CH_2)_3CH_3$
$CH_2CH(CH_3)_2$
$CH_2CH_2CH(CH_3)_2$
$CH_2$-cyclopentyl
$CH_2O(C_6H_5)$
$CH_2SCH_2CH(CH_3)2$
$CH_2NHCH_2CH(CH_3)_2$
$OCH_2CH(CH_3)_2$
$NHCH_2CH(CH_3)_2$
$C_6H_5$
$3CF_3-C_6H_4$
$2Cl-C_6H_4$ $R^1 = OCF_2H, R^2 = \overset{O}{\overset{\|}{C}}H$
$R^3$
$(CH_2)_3CH_3$
$CH_2CH(CH_3)_2$
$CH_2CH_2CH(CH_3)_2$
$CH_2$-cyclopentyl
$CH_2O(C_6H_5)$
$CH_2SCH_2CH(CH_3)2$
$CH_2NHCH_2CH(CH_3)_2$
$OCH_2CH(CH_3)_2$
$NHCH_2CH(CH_3)_2$
$C_6H_5$
$3CF_3-C_6H_4$
$2Cl-C_6H_4$ $R^1 = Cl, R^2 = \overset{S}{\overset{\|}{C}}OCH_3$
$R^3$
$(CH_2)_3CH_3$
$CH_2CH(CH_3)_2$
$CH_2CH_2CH(CH_3)_2$
$CH_2$-cyclopentyl
$CH_2O(C_6H_5)$
$CH_2SCH_2CH(CH_3)2$
$CH_2NHCH_2CH(CH_3)_2$
$OCH_2CH(CH_3)_2$
$NHCH_2CH(CH_3)_2$
$C_6H_5$
$3CF_3-C_6H_4$
$2Cl-C_6H_4$ $R^1 = Br, R^2 = \overset{S}{\overset{\|}{C}}OCH_3$
$R^3$
$(CH_2)_3CH_3$
$CH_2CH(CH_3)_2$
$CH_2CH_2CH(CH_3)_2$
$CH_2$-cyclopentyl
$CH_2O(C_6H_5)$
$CH_2SCH_2CH(CH_3)2$
$CH_2NHCH_2CH(CH_3)_2$
$OCH_2CH(CH_3)_2$
$NHCH_2CH(CH_3)_2$
$C_6H_5$
$3CF_3-C_6H_4$
$2Cl-C_6H_4$ $R^1 = OCF_3, R^2 = \overset{S}{\overset{\|}{C}}OCH_3$
$R^3$
$(CH_2)_3CH_3$
$CH_2CH(CH_3)_2$
$CH_2CH_2CH(CH_3)_2$
$CH_2$-cyclopentyl
$CH_2O(C_6H_5)$
$CH_2SCH_2CH(CH_3)2$
$CH_2NHCH_2CH(CH_3)_2$
$OCH_2CH(CH_3)_2$
$NHCH_2CH(CH_3)_2$
$C_6H_5$
$3CF_3-C_6H_4$
$2Cl-C_6H_4$ $R^1 = OCF_2H, R^2 = \overset{S}{\overset{\|}{C}}OCH_3$
$R^3$
$(CH_2)_3CH_3$
$CH_2CH(CH_3)_2$
$CH_2CH_2CH(CH_3)_2$
$CH_2$-cyclopentyl
$CH_2O(C_6H_5)$
$CH_2SCH_2CH(CH_3)2$
$CH_2NHCH_2CH(CH_3)_2$
$OCH_2CH(CH_3)_2$
$NHCH_2CH(CH_3)_2$
$C_6H_5$
$3CF_3-C_6H_4$
$2Cl-C_6H_4$ $R^1 = Cl, R^2 \ CH_2OH$
$R^3$
$(CH_2)_3CH_3$
$CH_2CH(CH_3)_2$
$CH_2CH_2CH(CH_3)_2$
$CH_2$-cyclopentyl
$CH_2O(C_6H_5)$
$CH_2SCH_2CH(CH_3)2$
$CH_2NHCH_2CH(CH_3)_2$
$OCH_2CH(CH_3)_2$
$NHCH_2CH(CH_3)_2$
$C_6H_5$
$3CF_3-C_6H_4$
$2Cl-C_6H_4$ $R^1 = Br, R^2 \ CH_2OH$
$R^3$
$(CH_2)_3CH_3$
$CH_2CH(CH_3)_2$
$CH_2CH_2CH(CH_3)_2$
$CH_2$-cyclopentyl
$CH_2O(C_6H_5)$
$CH_2SCH_2CH(CH_3)2$
$CH_2NHCH_2CH(CH_3)_2$
$OCH_2CH(CH_3)_2$
$NHCH_2CH(CH_3)_2$
$C_6H_5$
$3CF_3-C_6H_4$
$2Cl-C_6H_4$ $R^1 = OCF_3, R^2 \ CH_2OH$
$R^3$
$(CH_2)_3CH_3$
$CH_2CH(CH_3)_2$
$CH_2CH_2CH(CH_3)_2$
$CH_2$-cyclopentyl
$CH_2O(C_6H_5)$
$CH_2SCH_2CH(CH_3)2$
$CH_2NHCH_2CH(CH_3)_2$
$OCH_2CH(CH_3)_2$
$NHCH_2CH(CH_3)_2$
$C_6H_5$
$3CF_3-C_6H_4$
$2Cl-C_6H_4$ $R^1 = OCF_2H, R^2 \ CH_2OH$
$R^3$
$(CH_2)_3CH_3$

TABLE 2-continued

CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

$R^1 = Cl, R^2 = \overset{O}{\overset{\|}{C}}NHCH_3$

R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

$R^1 = Br, R^2 = \overset{O}{\overset{\|}{C}}NHCH_3$

R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂

$R^1 = OCF_3, R^2 = \overset{O}{\overset{\|}{C}}NHCH_3$

R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

$R^1 = OCF_2H, R^2 = \overset{O}{\overset{\|}{C}}NHCH_3$

R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

$R^1 = Cl, R^2 = C=C\begin{smallmatrix}CN\\\\CNH_2\\\|\\O\end{smallmatrix}$

R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

$R^1 = Br, R^2 = C=C\begin{smallmatrix}CN\\\\CNH_2\\\|\\O\end{smallmatrix}$

R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

$R^1 = OCF_3, R^2 = C=C\begin{smallmatrix}CN\\\\CNH_2\\\|\\O\end{smallmatrix}$

R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

$R^1 = OCF_2H, R^2 = C=C\begin{smallmatrix}CN\\\\CNH_2\\\|\\O\end{smallmatrix}$

R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

TABLE 3

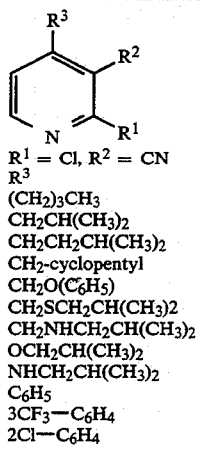

R¹ = Cl, R² = CN
R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

R¹ = Br, R² = CN
R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

R¹ = OCF₃, R² = CN
R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

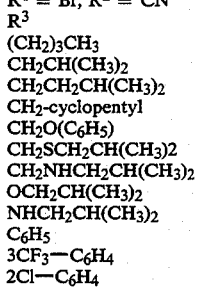

R¹ = Cl, R² = $\overset{O}{\overset{\|}{C}}$NH₂
R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

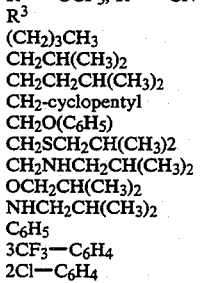

R¹ = Br, R² = $\overset{O}{\overset{\|}{C}}$NH₂
R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

TABLE 3-continued

3CF₃—C₆H₄
2Cl—C₆H₄

R¹ = OCF₃, R² = $\overset{O}{\overset{\|}{C}}$NH₂
R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

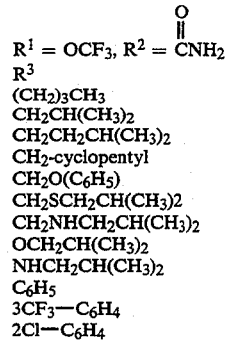

R¹ = Cl, R² = $\overset{O}{\overset{\|}{C}}$OH
R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

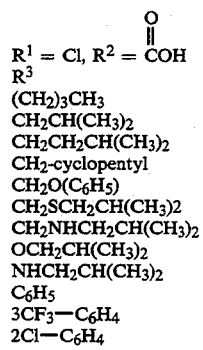

R¹ = Br, R² = $\overset{O}{\overset{\|}{C}}$OH
R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

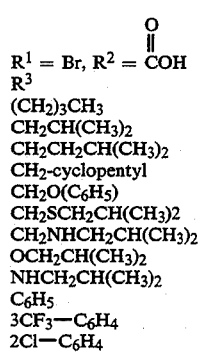

R¹ = OCF₃, R² = $\overset{O}{\overset{\|}{C}}$OH
R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
CH₂NHCH₂CH(CH₃)₂
OCH₂CH(CH₃)₂
NHCH₂CH(CH₃)₂
C₆H₅
3CF₃—C₆H₄
2Cl—C₆H₄

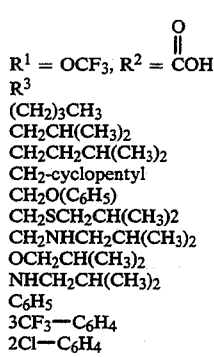

R¹ = Cl, R² = $\overset{O}{\overset{\|}{C}}$H
R³
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
OCH₂CH(CH₃)₂
NHCH₂CH(CH₃)₂

TABLE 3-continued

C₆H₅
3CF₃—C₆H₄
2Cl—C₆H₄

$R^1 = Br, R^2 = \overset{\overset{O}{\|}}{C}H$
$R^3$
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
OCH₂CH(CH₃)₂
NHCH₂CH(CH₃)₂
C₆H₅
3CF₃—C₆H₄
2Cl—C₆H₄

$R^1 = OCF_3, R^2 = \overset{\overset{O}{\|}}{C}H$
$R^3$
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
OCH₂CH(CH₃)₂
NHCH₂CH(CH₃)₂
C₆H₅
3CF₃—C₆H₄
2Cl—C₆H₄

$R^1 = Cl, R^2 = CH_2OH$
$R^3$
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
OCH₂CH(CH₃)₂
NHCH₂CH(CH₃)₂
C₆H₅
3CF₃—C₆H₄
2Cl—C₆H₄

$R^1 = Br, R^2 = CH_2OH$
$R^3$
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
OCH₂CH(CH₃)₂
NHCH₂CH(CH₃)₂
C₆H₅
3CF₃—C₆H₄
2Cl—C₆H₄

$R^1 = OCF_3, R^2 = CH_2OH$
$R^3$
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
OCH₂CH(CH₃)₂
NHCH₂CH(CH₃)₂
C₆H₅
3CF₃—C₆H₄
2Cl—C₆H₄

$R^1 = Cl, R^2 = \overset{\overset{O}{\|}}{C}OCH_3$
$R^3$
(CH₂)₃CH₃

TABLE 3-continued

CH₂CH(CH₃)₂
CH₂CH₂CH(CH₃)₂
CH₂-cyclopentyl
CH₂O(C₆H₅)
CH₂SCH₂CH(CH₃)2
OCH₂CH(CH₃)₂
NHCH₂CH(CH₃)₂
C₆H₅
3CF₃—C₆H₄
2Cl—C₆H₄

$R^1 = Br, R^2 = \overset{\overset{O}{\|}}{C}OCH_3$
$R^3$
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
OCH₂CH(CH₃)₂
NHCH₂CH(CH₃)₂
C₆H₅
3CF₃—C₆H₄
2Cl—C₆H₄

$R^1 = OCF_3, R^2 = \overset{\overset{O}{\|}}{C}OCH_3$
$R^3$
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
OCH₂CH(CH₃)₂
NHCH₂CH(CH₃)₂
C₆H₅
3CF₃—C₆H₄
2Cl—C₆H₄

$R^1 = Cl, R^2 = \overset{\overset{O}{\|}}{C}OCH_2CH_3$
$R^3$
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
OCH₂CH(CH₃)₂
NHCH₂CH(CH₃)₂
C₆H₅
3CF₃—C₆H₄
2Cl—C₆H₄

$R^1 = Br, R^2 = \overset{\overset{O}{\|}}{C}OCH_2CH_3$
$R^3$
(CH₂)₃CH₃
CH₂CH(CH₃)₂
CH₂CH₂CH(CH₃)₂
CH₂-cyclopentyl
CH₂O(C₆H₅)
CH₂SCH₂CH(CH₃)2
OCH₂CH(CH₃)₂
NHCH₂CH(CH₃)₂
C₆H₅
3CF₃—C₆H₄
2Cl—C₆H₄

$R^1 = OCF_3, R^2 = \overset{\overset{O}{\|}}{C}OCH_2CH_3$
$R^3$
(CH₂)₃CH₃
CH₂CH(CH₃)₂
CH₂CH₂CH(CH₃)₂
CH₂-cyclopentyl

TABLE 3-continued

CH$_2$O(C$_6$H$_5$)
CH$_2$SCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = Cl, R^2 = \overset{\overset{O}{\|}}{C}NHCH_3$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = Br, R^2 = \overset{\overset{O}{\|}}{C}NHCH_3$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = OCF_3, R^2 = \overset{\overset{O}{\|}}{C}NHCH_3$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = Cl, R^2 = C{\equiv}CH$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = Br, R^2 = C{\equiv}CH$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = OCF_3, R^2 = C{\equiv}CH$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = Cl, R^2 = \overset{\overset{S}{\|}}{C}—OCH_3$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = Br, R^2 = \overset{\overset{S}{\|}}{C}—OCH_3$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$ $R^1 = OCF_3, R^2 = \overset{\overset{S}{\|}}{C}—OCH_3$
R$^3$
(CH$_2$)$_3$CH$_3$
CH$_2$CH(CH$_3$)$_2$
CH$_2$CH$_2$CH(CH$_3$)$_2$
CH$_2$-cyclopentyl
CH$_2$O(C$_6$H$_5$)
CH$_2$SCH$_2$CH(CH$_3$)$_2$
OCH$_2$CH(CH$_3$)$_2$
NHCH$_2$CH(CH$_3$)$_2$
C$_6$H$_5$
3CF$_3$—C$_6$H$_4$
2Cl—C$_6$H$_4$

Formulations

This invention can be conveniently carried out by formulating a compound of Formula I in the conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The herbicidal formulations of the invention comprise 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

|  | Weight Percent* | | |
| --- | --- | --- | --- |
|  | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook or Insecticide Dust Diluents and Carriers", 2nd Ed Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed, Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp 147ff and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science:, John Wiley and Sons, Inc., New York, 1961, ppl 81–96; and J. D. Fryer and S. A. Evans, "Weed Control Handbook", 5th Ed Blackwell Scientific Publications, Oxford, 1968, pp. 101–103.

In the following Examples, all parts are by weight unless otherwise indicated.

EXAMPLE A

| Wettable Powder | |
| --- | --- |
| 2-bromo-6-(3-methylbutyl)-3-pyridinecarboxamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE B

| Granule | |
| --- | --- |
| Wettable Powder of Example A | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE C

| Extruded Pellet | |
| --- | --- |
| 2-bromo-6-(3-methylbutyl)-3-pyridinecarboxamide | 25% |
| anhydrous sodium sulfate | 10% |
| crude calcium liginsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE D

| Low Strength Granule | |
| --- | --- |
| 2-bromo-6-(3-methylbutyl)-3-pyridinecarboxamide | 0.1% |
| attapulgite granule (U.S.S. 20–40 sieve) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE E

| Low Strength Granule | |
|---|---|
| 2-bromo-6-(3-methylbutyl)-3-pyridinecarboxamide | 1% |
| N,N-dimethylformamide | 9% |
| attapulgite granule (U.S.S. 20–40 sieve) | 90% |

The active ingredient is dissolved in the solvent and the solution is sprayed upon dedusted granules in a double-cone blender. After spraying of the solution has been completed, the blender is allowed to run for a short period and then the granules are packaged.

EXAMPLE F

| Wettable Powder | |
|---|---|
| 2-bromo-6-(3-methylbutyl)-3-pyridinecarboxamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE G

| Emulsifiable Concentrate | |
|---|---|
| 2-bromo-6-(3-methylbutyl)-3-pyridinecarboxamide | 35% |
| blend of polyalcohol carboxylic esters and oil soluble petroleum sulfonates | 6% |
| xylene | 59% |

The ingredients are combined and filtered to remove undissolved solids. The product can be used directly, extended with oils, or emulsified in water.

EXAMPLE H

| Dust | |
|---|---|
| 2-bromo-6-(3-methylbutyl)-3-pyridinecarboxamide | 10% |
| attapulgite | 10% |
| Pyrophyllite | 80% |

The active ingredient is blended with attapulgite and then passed thorugh a hammer-mill to produce particles substantially all below 200 microns. The ground concentrate is then blended with powdered pyrophyllite until homogeneous.

EXAMPLE I

| Wettable Powder | |
|---|---|
| 2-bromo-6-(3-methylbutyl)-3-pyridinecarboxamide | 20% |
| sodium alkylnaphthalenesulfonate | 4% |
| sodium ligninsulfonate | 4% |
| low viscosity methyl cellulose | 3% |
| attapulgite granule | 69% |

The ingredients are thoroughly blended, coarsely hammer-milled and then air-milled to produce particles essentially all below 10 microns in size. The material is reblended and then packaged.

EXAMPLE J

| 2-bromo-6-(3-methylbutyl)-3-pyridinecarboxamide | 48.8% |
|---|---|
| Altox ® 3404F - anionic/nonionic emulsifier | 2.4% |
| Altox ® 3455F - anionic/nonionic emulsifier | 5.6% |
| Aromatic 100 (Exxon) - xylene range solvent | 43.2% |

The composition was prepared by mixing the ingredients together in a suitable vessel until complete dissolution of all the components occurred.

UTILITY

Test results indicate that the compositions of this invention include active postemergence and preemergence herbicides. The compositions of this invention are particularly useful for the control of barnyardgrass (*Echinocloa crus-galli*) in crops and especially in upland and paddy rice (*Oryza sativa*).

Effective rates of application for the compositions of this invention are determined by a number of factors. These factors include: formulation selected, method of application, amount and type of vegetation present, growing conditions, etc. In general terms, the compositions of the invention should be applied at rates which would involve from 0.005 to 10 kg/ha of the active compound of the composition with a preferred rate range of 0.01 to 1 kg/ha. One skilled in the art can easily determine effective application rates necessary for desired level of weed control.

The compositions of this invention may also include, in combination, other commercial herbicides, insecticides, or fungicides. The following list exemplifies some of the herbicides suitable for use in mixtures. A combination of a compound from the present composition with one or more of the following herbicides may be particularly useful for weed control in rice.

| Common Name | Chemical Name |
|---|---|
| acetochlor | 2-chloro-N-(ethoxymethyl)N-(2-ethyl-6-methylphenyl)acetamide |
| alachlor | 2-chloro-N-(2,6-diethylphenyl)-N-(methoxymethyl)acetamide |
| bensulfuron | 2-[[[[[(4,6-dimethoxy-2-pyrimidinyl)amino]methylcarbonyl]amino]-sulfonyl]methyl]benzoic acid, methyl ester |
| bentazon | 3-(1-methylethyl)-(1H)-2,1,3-benzothiadiazin-4(3H)-one, 2,2-dioxide |
| bifenox | methyl 5-(2,4-dichlorophenoxy)-2-nitrobenzoate |
| bromobutide | (+)2-bromo-3,3-dimethyl-N-(1-methyl-1-phenylethyl)butanamide |
| butachlor | N-(butoxymethyl)-2-chloro-N-(2,6-diethylphenyl)acetamide |
| CGA142464 | N-[2-(2-methoxyethoxy-phenyl sulfonyl]-N'-4,6-dimethoxy-1,3,5-triazin-2-yl urea |
| chlorimuron | 2-[[[[(4,chloro-6-methoxy-2-pyrimidinyl)ethylamino]carbonyl]amino]-sulfonyl]benzoic acid, ethyl ester |
| chlornitrofen | 1,3,5-trichloro-2-(4-nitrophenoxy)-benzene |
| chlorsulfuron | 2-chloro-N-[[(4-methoxy-6-methyl-1,3,5-triazin-2-yl)amino]carbonyl]-benzenesulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo-[2.2.1]heptane |
| cyperquat | 1-methyl-4-phenylpyridinium |
| cyprazine | 2-chloro-4-(cyclopropylamino)-6-(isopropylamino)-s-triazine |
| dithiopyr | s,s-dimethyl-2-(difluoromethyl)-4-(z- |

-continued

| Common Name | Chemical Name |
|---|---|
| | methylpropyl)-6-(trifluoromethyl)-3,5-pyridinedicarbothionate |
| DPX A8947 | N-[[(4,6-dimethoxypyrimidin-2-yl)-amino]carbonyl]-1-methyl-4-(2-methyl-2H-tetrazol-5-yl)-1H-pyrazole-5-sulfonamide |
| endothall | 7-oxabicyclo[2.2.1]heptane-2,3-dicarboxylic acid |
| esprocarb | s-(phenylmethyl)(1,2-dimethylpropyl) ethylcarbamothioate |
| isoproturon | N-(4-isopropylphenyl)-N',N'-dimethyl-urea |
| MCPA | (4-chloro-2-methylphenoxy)acetic acid |
| mefenacet | 2-(2-benzothiazolyloxy)-N-methyl-N-phenyl acetamide |
| metsulfuron methyl | 2-[[[[(4-methoxy-6-methyl-1,3,5-triazin-2-yl)amino]carbonyl]-amino]sulfonyl]benzoic acid, methyl ester |
| molinate | S-ethyl hexahydro-1H-azepine-1-carbo-thioate |
| MY-93 | 1-piperidinecarbothioic acid,s-/1-methyl-1-phenyl ethyl/ester |
| NSK 850 | 2-chloro-N-(2,6-dimethylphenyl)-N-(((3-methoxy-2-thienyl)methyl))-acetamide |
| oxadiazon | 3-[2,4-dichloro-5-(1-methylethoxy)-phenyl]-5-(1,1-dimethylethyl)-1,3,4-oxadiazol-2(3H)-one |
| oxyfluorfen | 2-chloro-1-(3-ethoxy-4-nitrophenoxy)-4-(trofluoromethyl)benzene |
| pretilachlor | 2-chloro-N-(2,6-diethylphenyl)-N-(2-propoxyethyl)acetamide |
| propanil | N-(3,4-dichlorophenyl)propanamide |
| pyrazolate | 4-(2,4-dichloro benzoyl)-1,3-dimethylpyrazol-5-yl-p-toluene-sulphonate |
| pyrazosulfuron-ethyl | ethyl 5-[[[[(4,6-dimethoxy-2-pyrimidinyl)amino]carbonyl]-amino]sulfonyl]-1-methyl-1H-pyrazole-4-carboxylate |
| quinclorac | 3,7-dichloro-8-quinolinecarboxylic acid |
| thifensulfuron | 3-[[[[(4-methoxy-6-methyl-1,3,5-triazin-2-yl)amino]carbonyl]amino]-sulfonyl]-2-thiophenecarboxylic acid, methyl ester |
| thiameturon-methyl | methyl 3-[[[[(4-methoxy-6-methyl-1,3,5-triazin-2-yl)amino]carbonyl]-amino]sulfonyl]2-thiophene-carboxylate |
| thiobencarb | S-[(4-chlorophenyl)methyl] diethyl-carbamothioate |
| tiocarbazil | S-(phenylmethyl)bis(1-methylpropyl)-carbamothioate |
| trisulfuron | 2-(2-chloroethoxy)-N-[[(4-methoxy-6-methyl-1,3,5-triazin-2-yl)amino]-carbonyl]benzenesulfonamide |
| tribenuron methyl | 2-[[[[N-(4-methoxy-6-methyl-1,3,5-triazine-2-yl)-N-methylamino]-carbonyl]amino]sulfonyl] benzoic acid, methyl ester |
| 2,4-D | (2,4-dichlorophenoxy)acetic acid |

Selective herbicidal properties of the subject compounds were discovered in greenhouse tests as described below.

TABLE 4

| CMPD | $R^1$ | $R^2$ | $R^3$ | mp (°C.) |
|---|---|---|---|---|
| 1 | Cl | C≡N | $C_6H_5$ | 135–136 |
| 2 | Cl | $CO_2CH_3$ | $CH_2CH(CH_3)_2$ | oil |
| 3 | Cl | $C(O)NH_2$ | $CH_2CH(CH_3)_2$ | 110–118 |
| 5 | $OCH_3$ | C≡N | $CH_2CH(CH_3)_2$ | oil |
| 6 | Cl | C≡N | $CH_2$-cyclopentyl | 65–68 |
| 7 | Cl | C(O)—NH—C$_6$H$_3$F$_2$ (2,4-difluorophenyl) | $CH_2CH(CH_3)_2$ | 75–76 |
| 8 | Cl | C≡N | $CH_2CH_2CH(CH_3)_2$ | 30–31 |
| 9 | Cl | $C(O)NH_2$ | $C_6H_5$ | 176–178 |
| 10 | Cl | C≡N | $CH_2$—$C_6H_5$ | oil |
| 11 | Cl | $C(O)NH_2$ | $CH_2$-cyclopentyl | 120–121 |
| 12 | Cl | C≡N | $3CF_3C_6H_4$ | 105–108 |
| 13 | Cl | $C(O)NH_2$ | $CH_2CH_2CH(CH_3)_2$ | 119–120 |
| 14 | Cl | $C(O)NH_2$ | $CH_2C_6H_5$ | 95–98 |
| 15 | Cl | $C(O)NH_2$ | $3CF_3C_6H_4$ | 109–112 |
| 16 | $OCH_3$ | C≡N | $CH_2C_6H_5$ | 117–121 |
| 17 | $OCH_3$ | $C(O)NH_2$ | $3CF_3C_6H_4$ | 174–176 |
| 18 | Cl | $CO_2H$ | $CH_2CH(CH_3)_2$ | 75–80 |
| 19 | Br | C≡N | $CH_2CH(CH_3)_2$ | oil |
| 20 | Cl | C≡N | $CH_2CH_2CH_2CH_3$ | oil |
| 21 | Br | $C(O)NH_2$ | $CH_2CH(CH_3)_2$ | 118–120 |
| 22 | Cl | $C(O)NH_2$ | $CH_2CH_2CH_2CH_3$ | 98–100 |
| 23 | Cl | C(O)NH—$CH_2$-cyclopropyl | $CH_2CH(CH_3)_2$ | 60–63 |
| 24 | Cl | C(O)NH-cyclopropyl | $CH_2CH(CH_3)_2$ | 78–80 |
| 25 | Cl | C≡N | CH=CH(CH$_3$)$_2$ | 65–68 |
| 26 | Cl | $C(O)NHOCH_3$ | $CH_2CH(CH_3)_2$ | oil |
| 27 | Cl | $C(O)N(CH_3)_2$ | $CH_2CH(CH_3)_2$ | oil |
| 28 | Cl | $C(O)NCH_3(OCH_3)$ | $CH_2CH(CH_3)_2$ | oil |

TABLE 4-continued

| CMPD | R¹ | R² | R³ | mp (°C.) |
|---|---|---|---|---|
| 29 | Cl | (2-oxocyclohex-1-en-1-yl ester: −C(=O)−O− attached to cyclohexenone) | $CH_2CH(CH_3)_2$ | 50–53 |
| 30 | Cl | C≡N | $CH_2CH_2CH_3$ | oil |
| 31 | Cl | $CO_2H$ | $CH_2CH_2CH_3$ | 90–93 |
| 32 | Cl | $CO_2H$ | $CH_2$-cyclopentyl | 87–89 |
| 33 | Cl | $CO_2H$ | $CH_2CH_2CH_2CH_3$ | oil |
| 34 | Cl | $CO_2H$ | $CH_2CH_2CH(CH_3)_2$ | oil |
| 35 | Cl | $C(O)NH_2$ | $CH_2CH_2CH_3$ | 94–95 |
| 36 | Cl | C≡N | $CH_2(CH_2)_4CH_3$ | oil |
| 37 | Cl | $C(O)NH_2$ | $CH_2(CH_2)_4CH_3$ | 87–89 |
| 38 | Cl | C≡N | $CH_2(CH_3)_3$ | 42–45 |
| 39 | Br | C≡N | $CH_2CH_2CH(CH_3)_2$ | oil |
| 40 | Cl | $CO_2H$ | $C_6H_5$ | 183–185 |
| 41 | Br | $C(O)NH_2$ | $CH_2CH_2CH(CH_3)_2$ | 110–112 |
| 42 | Cl | CHO | $CH_2CH(CH_3)_2$ | oil |
| 43 | Br | $CO_2H$ | $CH_2CH_2CH(CH_3)_2$ | oil |
| 45 | Cl | $C(O)NH_2$ | $CH_2C(CH_3)_3$ | 110–114 |
| 46 | Cl | C—N—$OCH_3$ | $CH_2CH(CH_3)_2$ | oil |
| 47 | Cl | $CH_2OH$ | $CH_2CH(CH_3)_2$ | oil |
| 48 | Cl | $C(O)NH_2$ | $CH=CH(CH_3)_2$ | 115–118 |
| 49 | Cl | C≡N | $CH_2CH_2C_6H_5$ | 60–67 |
| 50 | Cl | $C(S)NH_2$ | $CH_2CH(CH_3)_2$ | 175–184 |
| 51 | Cl | C≡N | $CH_2CH_2CH(CH_3)CH_2CH_2CH_3$ | oil |
| 52 | Cl | $C(O)NH_2$ | $CH_2CH_2C_6H_5$ | 138–144 |
| 53 | Cl | $C(O)NH_2$ | $CH_2CH_2CH(CH_3)CH_2CH_2CH_3$ | 80–84 |
| 54 | Br | $C(O)NH_2$ | $CH_2$-cyclopentyl | 97–105 |
| 55 | Br | $C(O)NH_2$ | $CH_2CH_2CH_2CH_3$ | 111–114 |
| 56 | Br | C≡N | t-butyl | 47 |
| 57 | Br | C≡N | $CH_2$-cyclopentyl | 64–66 |
| 58 | Br | C≡N | $CH_2CH_2CH_2CH_3$ | oil |
| 59 | Cl | C≡N | $CH_2CH(CH_3)_2$ | 49–50 |
| 60 | $OCH_3$ | C≡N | $CH_2(CH_3)_3$ | |
| 61 | Cl | $CO_2H$ | $OCH_2CH_2CH_2CH_3$ | 95–98 |
| 62 | Cl | C≡N | $OC_6H_5$ | 39–41 |
| 63 | Cl | C≡N | $SC(CH_3)_3$ | oil |
| 64 | Cl | C≡N | $OCH_2CH(CH_3)_2$ | oil |
| 65 | Cl | $C(O)NH_2$ | O(t-butyl) | 118–119 |
| 66 | Cl | $C(O)NH_2$ | $OC_6H_5$ | 145–146 |
| 67 | Cl | $C(O)NH_2$ | $OCH_2CH(CH_3)_2$ | 112–115 |
| 68 | Cl | C≡N | $CH_2OC_6H_5$ | 138–140 |
| 69 | Cl | $C(O)NH_2$ | $CH_2OC_6H_5$ | 156–148 |
| 70 | Cl | $C(O)NH_2$ | S(t-butyl) | 78–80 |
| 71 | Br | $C(O)NH_2$ | $CH_2(CH_2)_3CH_3$ | 68–70 |
| 72 | Br | C≡N | $CH_2CH_2CH(CH_3)CH_2CH_2CH_3$ | oil |
| 73 | Br | $C(O)NH_2$ | $CH_2CH_2CH(CH_3)CH_2CH_2CH_3$ | oil |
| 74 | Cl | $C(O)NH_2$ | $2Cl-C_6H_4$ | 200–201 |
| 75 | Cl | $C(O)NH_2$ | $4Cl-C_6H_4$ | 215–216 |
| 76 | Cl | $CH=C(CN)_2$ | $CH_2CH_2CH(CH_3)_2$ | 70–71 |
| 77 | Cl | $CH=C(CN)C(O)NH_2$ | $CH_2CH_2CH(CH_3)_2$ | 132–135 |
| 78 | Cl | $HC=C(CN)CO_2CH_3$ | $CH_2CH_2CH(CH_3)_2$ | 48–49 |
| 79 | Cl | $CH=CH-CO_2CH_3$ | $CH_2CH_2CH(CH_3)_2$ | oil |
| 80 | Br | $C(O)NH_2$ | $CH_2C(CH_3)_3$ | 81–82 |
| 81 | Cl | $C(O)NH_2$ | $CH_2(CH_2)_3CH_3$ | 81–82 |
| 82 | Br | C≡N | $CH_2C(CH_3)_3$ | oil |
| 83 | Cl | C≡N | $CH_2(CH_2)_3CH_3$ | oil |
| 98 | Cl | CN | $3Br-C_6H_4$ | 138–139 |
| 99 | Cl | $C(O)NH_2$ | $3Br-C_6H_4$ | 160–161 |
| 100 | Cl | CN | $CH_2-OC_6H_5$ | 138–140 |
| 101 | Cl | $C(O)NH_2$ | $CH_2-OC_6H_5$ | 156–158 |
| 102 | Cl | $C(O)NH_2$ | $OCH_2CH(CH_3)_2$ | 112–115 |
| 103 | Cl | CN | $4F-C_6H_4$ | 85–87 |
| 104 | Cl | CN | $2Cl-C_6H_4$ | 102–105 |
| 105 | Cl | $C(O)NH_2$ | $3Cl-C_6H_4$ | 145–148 |
| 106 | Cl | CN | $4Cl-C_6H_4$ | 155–156 |
| 107 | Cl | $C(O)NH_2$ | $4F-C_6H_4$ | 185–186 |
| 108 | Cl | CN | $3Cl-C_6H_4$ | 108–110 |
| 109 | Cl | $C(O)NH_2$ | $SCH_2CH(CH_3)_2$ | 95–100 |
| 110 | Cl | $CO_2H$ | $SCH_2CH(CH_3)_2$ | oil |
| 111 | Br | CN | $CH_2CH_2CH(CH_3)CH_2CH_2CH_3$ | oil |
| 112 | Br | $C(O)NH_2$ | $CH_2CH_2CH(CH_3)CH_2CH_2CH_3$ | semisolid |
| 114 | Cl | CN | $SCH_2CH(CH_3)_2$ | oil |
| 115 | Cl | $C(O)NH_2$ | $SC(CH_3)_3$ | 78–80 |
| 116 | Cl | $C(O)NH_2$ | $OC(CH_3)_3$ | 118–119 |
| 117 | Cl | CN | $SC(CH_3)_3$ | oil |

TABLE 5

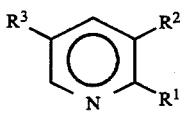

| CMPD | R¹ | R² | R³ | mp (°C.) |
|---|---|---|---|---|
| 84 | Br | C(O)NH₂ | CH₂(CH₂)₃CH₃ | 87 |

TABLE 6

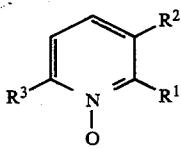

| CMPD | R² | R² | R³ | mp (°C.) |
|---|---|---|---|---|
| 44 | Cl | C≡N | CH₂CH(CH₃)₂ | 72–73 |

TABLE 7

| CMPD | | SPECTRAL DATA |
|---|---|---|
| 2 | NMR (CDCl₃): | ppm δ 8.1 (d, 1H); 7.13(d, 1H); 3.94 (s, 3H); 2.69(d, 2H); 2.1(m, 1H); 0.947 (d, 6H) |
| | IR (Neat): | 1740 cm⁻¹(C=O) |
| 5 | NMR (CDCl₃): | ppm δ 7.7(d, 1H); 6.8(d, 1H); 4.0(s, 3H); 2.6(d, 2H); 2.2(m, 1H); 0.949(d, 6H) |
| | IR (Neat): | 2210 cm⁻¹(C≡N) |
| 10 | NMR (CDCl₃): | ppm δ 7.86(d, 1H); 7.3(m, 2H); 7.13 (d, 1H); 4.8(s, 2H) |
| | IR (Neat): | 2220 cm⁻¹(C≡N) |
| 19 | NMR (CDCl₃): | ppm δ 7.8(d, 1H); 7.2(d, 1H); 2.7(d, 2H); 2.1(m, 1H); 0.95(d, 6H) |
| | IR (Neat): | 2220 cm⁻¹(C≡N) |
| 20 | NMR (CDCl₃): | ppm δ 7.9(d, 1H); 7.2(d, 1H); 2.8 (t, 2H); 1.7(m, 2H); 1.4(m, 2H); 1.0 (t, 3H) |
| | IR (Neat): | 2220 cm⁻¹(C≡N) |
| 26 | NMR (CDCl₃): | ppm δ 9.1(s, 1H); 8.0(d, 1H); 7.1(d, 1H); 3.9(s, 3H); 2.7(d, 2H); 2.1(m, 1H); 0.9 (d, 6H); |
| 27 | NMR (CDCl₃): | ppm δ 7.5(d, 1H); 7.1(d, 1H); 3.1(s, 3H); 2.9(s, 3H); 2.6(d, 2H); 2.1(m, 1H); 0.95 (d, 6H) |
| | IR (Neat): | 1650 cm⁻¹(C=O) |
| 28 | NMR (CDCl₃): | ppm δ 7.6(d, 1H); 7.1(d, 1H); 3.5(s, 3H); 3.3(s, 3H); 2.7(d, 2H); 2.1(m, 1H); 0.949 (d, 6H) |
| | IR (Neat): | 1650 cm⁻¹(C=O) |
| 30 | NMR (CDCl₃): | ppm δ 7.9(d, 1H); 7.2(d, 1H); 2.8(t, 2H); 1.8(m, 2H); 1.0(t, 3H) |
| | IR (Nujol): | 2220 cm⁻¹(C≡N) |
| 33 | NMR (CDCl₃): | ppm δ 8.5(bs, 1H); 8.2(d, 1H); 7.2(d, 1H); 2.8(t, 2H); 1.7(m, 2H); 1.4(m, 2H); 1.0 (t, 3H) |
| | IR (Neat): | 1740 cm⁻¹(C=O) |
| 34 | NMR (CDCl₃): | ppm δ 8.28(d, 1H); 7.23(d, 1H); 2.8 (m, 2H); 1.6(m, 2H); 1.2(m, 1H); 0.97 (d, 6H) |
| | IR (Neat): | 1700 cm⁻¹; (C=O) |
| 36 | NMR (CDCl₃): | ppm δ 7.9(d, 1H); 7.2(d, 1H); 2.8 (t, 2H); 1.7(m, 2H); 1.3(m, 6H); 0.9(t, 3H) |
| | IR (Neat): | 2220 cm⁻¹(C≡N) |
| 39 | NMR (CDCl₃): | ppm δ 7.8(d, 1H); 7.2(d, 1H); 2.8(t, 2H); 1.6(m, 3H); 0.9(d, 6H) |
| | IR (Neat): | 2220 cm⁻¹(C≡N) |
| 42 | NMR (CDCl₃): | ppm δ 10.5(s, 1H) ; 8.2(d, 1H) ; 7.2(d, 1H) 2.72(d, 2H); 2.2(m, 1H); 0.96(d, 6H) |
| | IR (Neat): | 2860, 1730 cm⁻¹(C=O) |
| 43 | NMR (CDCl₃): | ppm δ 8.21(d, 1H); 7.24(d, 1H); 2.8 (m, 2H); 1.6(m, 3H); 0.967(m, 6H) |
| | IR (Neat): | 2940, 1700 cm⁻¹(C=O) |
| 46 | NMR (CDCl₃): | ppm δ 8.4(s, 1H); 8.05(d, 1H); 7.0 (d, 1H); 3.99(s, 3H); 2.61(d, 2H); 2.2 (m, 1H); 0.945(d, 6H) |

TABLE 7-continued

| CMPD | | SPECTRAL DATA |
|---|---|---|
| 47 | IR (Neat): | 1580, 1540 cm⁻¹(C=N) |
| | NMR (CDCl₃): | ppm δ 7.8(d, 1H); 7.1(d, 1H); 4.7(d, 2H); 2.6(d, 2H); 2.1(m, 1H); 0.9(d, 6H) |
| 51 | IR (Neat): | 3300 cm⁻¹(OH); |
| | NMR (CDCl₃): | ppm δ 7.89(d, 1H); 7.2(d, 1H); 2.8 (m, 2H); 2.8–1.0(m, 7H); 0.943(m, 6H) |
| 58 | IR (Neat): | 2220 cm⁻¹(C≡N) |
| | NMR (CDCl₃): | ppm δ 7.8(d, 1H); 7.3(d, 1H); 2.86 (m, 2H); 1.8(m, 2H); 1.4(m, 2H); 0.96 (m, 3H) |
| 64 | IR (Neat): | 2210 cm⁻¹(C≡N) |
| | NMR (CDCl₃): | ppm δ 7.8(m, 1H); 7.0(m, 1H); 4.2(m, 2H); 2.1(m, 1H); 1.0(m, 6H)+6-isomer |
| 72 | IR (Neat): | 2220 cm⁻¹(C≡N) |
| | NMR (CDCl₃): | ppm δ 7.8(d, 1H); 7.2(d, 1H); 2.8(m, 2H); 1.8–1.1(m, 7H); 1.0–0.8(m, 6H) |
| 73 | IR (Neat): | 2220 cm⁻¹(C≡N) |
| | NMR (CDCl₃): | ppm δ 7.9(d, 1H); 7.2(d, 1H); 6.7(s, 1H); 6.5(s, 1H); 2.8(m, 2H); 1.8–1.1(m, 7H); 1.0–0.8(m, 6H) |
| 79 | IR (Nujol): | 3360, 3180 cm⁻¹(NH₂)1650 cm⁻¹(C=O) |
| | NMR (CDCl₃): | ppm δ 7.98(d, 1H); 7.81(d, 1H); 7.13(d, 1H); 6.41(d, 1H); 3.83(s, 3H); 2.78 (m, 2H); 1.61(m, 3H); 0.94(d, 6H) |
| 82 | IR (Neat): | 1710 cm⁻¹(C=O) |
| | NMR (CDCl₃): | ppm δ 7.83(m, 1H); 7.21(m, 1H); 2.7 (s, 2H); 1.02(s, 9H) |
| 83 | IR (Nujol): | 2210 cm⁻¹(C≡N) |
| | NMR (CDCl₃): | ppm δ 7.89(d, 1H); 7.22(d, 1H); 2.84(m, 2H); 1.8(m, 2H); 1.35(m, 4H); 0.899 (m, 3H) |
| 110 | IR (Neat): | 2210 cm⁻¹(C≡N) |
| | NMR(CDCl₃): | ppm δ 8.2(m, 1H); 7.2(m, 1H); 3.05 (m, 2H); 2.0(m, 1H); 1.09(d, 6H) |
| 111 | NMR (CDCl₃): | ppm δ 7.82(d, 1H); 7.2(d, 1H); 2.8 (m, 2H); 1.8–1.0(m, 5H); 0.866(m, 6H) |
| | IR (Neat): | 2210 cm⁻¹(C≡N) |
| 112 | NMR (CDCl₃): | ppm δ 7.94(d, 1H); 7.21(d, 1H); 6.7(bs, 1H); 6.6(bs, 1H); 2.8(m, 2H); 1.8–1.2(m, 7H); 0.9(m, 6H) |
| | IR (Nujol): | 3350 cm⁻¹(NH); 1650 cm⁻¹(C=O) |
| 114 | NMR (CDCl₃): | ppm δ 7.6(d, 1H); 7.05(d, 1H); 3.1 (m, 2H); 2.0(m, 1H); 1.0(m, 6H)+ 10% isomer |
| | IR (Neat): | 2210 cm⁻¹(C≡N) |
| 117 | NMR (CDCl₃): | ppm δ 7.6(d, 1H) ; 7.0(d, 1H); 1.67 (s, 9H) |
| | IR (Neat): | 2210 cm⁻¹(C≡N) |

The following are additional compounds tested in Tests E, F and G.

| CMPD | COMMON NAME | CHEMICAL NAME |
|---|---|---|
| 86 | bensulfuron methyl | 2-[[[[(4,6-dimethoxy-2-pyrimidinyl)-amino]methylcarbonyl]amino]-sulfonyl]methyl]benzoic acid, methyl ester |
| 87 | CGA142464 | N-[2-(2-methoxyethoxyphenyl sulfonyl]-N'-4,6-dimethoxy-1,3,5-triazin-2-yl urea |
| 88 | DPX A8947 | N-[[(4,6-dimethoxypyrimidin-2-yl)-amino]carbonyl)-1-methyl-4-(2-methyl-2H-tetrazol-5-yl)-1H-pyrazole-5-sulfonamide |
| 89 | mefenacet | 2-(2-benzothiazolyloxy)-N-methyl-N-phenyl acetamide |
| 90 | metsulfuron methyl | 2-[[[[(4-methoxy-6-methyl-1,3,5-triazin-2-yl)amino]carbonyl]amino]-sulfonyl]benzoic acid, methyl ester |
| 91 | molinate | S-ethyl hexahydro-1H-azepin-1-carbothioate |
| 92 | pyrazosulfuron ethyl | ethyl 5-[[[[(4,6-dimethoxy-2-pyrimidinyl)amino]carbonyl]amino]-sulfonyl]-1-methyl-1H-pyrazole-4-carboxylate |
| 93 | quinclorac | 3,7-dichloro-8-quinolinecarboxylic |

| CMPD | COMMON NAME | CHEMICAL NAME |
|---|---|---|
| 94 | (unknown) | acid N-[[(4,6-dimethoxy-2-pyrimidinyl)-amino]carbonyl]-3-methyl-5-(2,2,2-trifluoroethoxy)-4-isothiazole-sulfonamide |
| 95 | TH-913 | 3-chloro-N-[[(4,6-dimethoxy-2-pyrimidinyl)amino]carbonyl]imidazo-[1,2-a]pyridine-3-sulfonamide |
| 96 | MON7200 | S,S-dimethyl 2-(difluoromethyl)-4-(2-methylpropyl)-6-(trifluoromethyl)-3,5-pyridinecarbothioate |
| 97 | butachlor | N-(butoxymethyl)-2-chloro-N-(2,6-diethylphenyl)acetamide |

TEST A

Seeds of barnyardgrass (*Echinochloa crus-galli*), cheatgrass (*Bromus secalinus*), cocklebur (*Xanthium pensylvanicum*), crabgrass (*Digitaria spp.*), giant foxtail (*Setaria faberii*), morningglory (*Ipomoea spp.*), sorghum (*Sorghum bicolor*), velvetleaf (*Abutlion theophrasti*), and wild oat (*Avena fatua*) were planted into a sandy loam soil and treated preemergence with test chemicals dissolved in a non-phytotoxic solvent. At the same time, these crop and weed species were also treated postemergence with test chemicals. Plants ranged in height from two to eighteen cm and were in the two to three leaf stage for the postemergence treatment. Treated plants and untreated controls were maintained in a greenhouse for approximately eleven days, after which all treated plants were compared to untreated controls and visually evaluated for injury. Plant response ratings, summarized in Table A, are based on a 0 to 10 scale where 0 is no effect and 10 is complete control. A dash (-) response means no test results.

TABLE A

| Rate (2000 g/ha) | COMPOUND 59 | COMPOUND 60 |
|---|---|---|
| POSTEMERGENCE | | |
| Barnyardgrass | 10 | 0 |
| Cheatgrass | 0 | 0 |
| Cocklebur | — | 0 |
| Crabgrass | 1 | 0 |
| Giant foxtail | 0 | 0 |
| Morningglory | 0 | 0 |
| Sorghum | 0 | 0 |
| Velvetleaf | 0 | 0 |
| Wild oat | 0 | 0 |
| PREEMERGENCE | | |
| Barnyardgrass | 9 | 0 |
| Cheatgrass | 0 | 0 |
| Cocklebur | — | 0 |
| Crabgrass | 0 | 0 |
| Giant foxtail | 0 | 0 |
| Morningglory | 0 | 0 |
| Sorghum | 0 | 0 |
| Velvetleaf | 0 | 0 |
| Wild oat | 0 | 0 |

TEST B

Seeds of barley (*Hordeum vulgate*), barnyardgrass (*Echinochloa crus-galli*), bedstraw (*Galium aparine*), blackgrass (*Alopecurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crabgrass (*Digitaria spp.*), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table B, are based on a scale of 0 to 10 where 0 is no effect and 10 is complete control. A dash (-) response means no test result.

TABLE B

| | COMPOUND | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| Rate (2000 g/ha) | | | | | | | | | | | | | | | | | | | | | | | | | |
| POSTEMERGENCE | | | | | | | | | | | | | | | | | | | | | | | | | |
| Barley | 0 | 0 | 0 | 0 | 0 | 0 | 0 | 0 | 0 | 0 | 0 | 0 | 0 | 1 | 1 | 0 | 0 | 0 | 0 | 0 | 0 | 0 | 0 |
| Barnyardgrass | 10 | 9 | 10 | 0 | 2 | 10 | 7 | 10 | 10 | 2 | 10 | 10 | 7 | 9 | 3 | 3 | 10 | 10 | 10 | 10 | 10 | 8 | 3 |
| Bedstraw | 0 | 0 | 0 | 0 | 0 | 2 | 0 | 0 | 0 | 0 | 0 | 0 | 0 | 1 | 1 | 0 | 0 | 0 | 0 | 0 | — | 0 | 0 |
| Blackgrass | 0 | — | 0 | 0 | 0 | 1 | 0 | 0 | 0 | 0 | 0 | 0 | 0 | 1 | 1 | 0 | 0 | 0 | 0 | 0 | 0 | 0 | 0 |
| Cheatgrass | 0 | 0 | 0 | 0 | 0 | 0 | 0 | 0 | 0 | 0 | 0 | 0 | 0 | 1 | 1 | 0 | 0 | 0 | 0 | 0 | 0 | 0 | 0 |
| Chickweed | 0 | 0 | 0 | — | 0 | 2 | 0 | 0 | 0 | 0 | 0 | 0 | — | 1 | — | 0 | 0 | 0 | 0 | 0 | 0 | 0 | 0 |
| Cocklebur | 1 | 0 | 0 | 0 | 0 | 0 | 0 | 0 | 0 | 0 | 0 | 0 | 1 | 0 | 1 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 1 | 1 | 0 | 1 | 1 | 0 | 0 | 0 | 0 | 0 |
| Cotton | 2 | 0 | 0 | 0 | 0 | 0 | 1 | 0 | 0 | 0 | 0 | 0 | 1 | 0 | 1 | 0 | 7 | 0 | 2 | 0 | 4 | 0 | 0 |
| Crabgrass | 0 | 0 | 0 | 0 | 0 | 0 | 0 | 0 | 0 | 0 | 0 | 0 | 2 | 1 | 1 | 0 | 1 | 5 | 0 | 0 | 1 | 3 | 3 |
| Giant foxtail | 0 | 0 | 0 | 0 | 0 | 3 | 0 | 0 | 0 | 0 | 0 | 0 | 2 | 1 | 1 | 0 | 2 | 1 | 0 | 0 | 1 | 2 | 0 |
| Lambsquarters | 0 | — | — | — | 0 | 2 | 0 | 0 | 1 | 0 | 0 | 0 | 0 | 1 | 1 | 0 | 1 | 0 | 0 | 0 | 0 | 0 | 1 |
| Morningglory | 0 | 1 | 0 | 0 | 0 | 0 | 0 | 0 | 0 | 0 | 0 | 0 | 1 | 0 | 1 | 0 | 1 | 0 | 0 | 0 | 0 | 0 | 2 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 2 | 0 | 1 | 0 | 0 | 0 | 0 | 0 | 1 | 0 | 0 | 0 | 0 | 0 | 0 | 0 | 0 | 0 |
| Rice | 0 | 0 | 0 | 0 | 0 | 0 | 0 | 2 | 0 | 0 | 0 | 0 | 0 | 0 | 0 | 0 | 5 | 2 | 0 | 0 | 2 | 0 | 0 |
| Sorghum | 0 | 0 | 0 | 0 | 0 | 0 | 0 | 0 | 0 | 0 | 0 | 0 | 0 | 1 | 1 | 0 | 1 | 0 | 1 | 0 | 0 | 0 | 0 |
| Soybean | 4 | 0 | 0 | 0 | 0 | 0 | 1 | 2 | 0 | 0 | 0 | 0 | 1 | 0 | 1 | 0 | 1 | 0 | 1 | 0 | 2 | 0 | 0 |
| Sugar beet | 0 | 0 | 0 | 0 | 0 | 0 | 0 | 0 | 0 | 0 | 0 | 0 | 0 | 0 | 1 | 0 | 1 | 0 | 0 | 0 | 0 | 0 | 0 |
| Velvetleaf | 0 | 0 | 3 | 3 | 0 | 0 | 0 | 0 | 0 | 0 | 0 | 0 | 1 | 0 | 1 | 0 | 2 | 6 | 0 | 0 | 0 | 0 | 0 |
| Wheat | 0 | 0 | 0 | 0 | 0 | 0 | 0 | 0 | 0 | 0 | 0 | 0 | 0 | 1 | 1 | 0 | 0 | 0 | 0 | 0 | 0 | 0 | 0 |

TABLE B-continued

| | | | | | | | | | | | | | | | | | | | | | | | |
|---|---|---|---|---|---|---|---|---|---|---|---|---|---|---|---|---|---|---|---|---|---|---|---|
| Wild buckwheat | — | 0 | — | 0 | — | — | — | 0 | 0 | 0 | 0 | — | 0 | 1 | 1 | — | 0 | 0 | — | 0 | 0 | 0 | 1 |
| Wild oat | 0 | 0 | 0 | 0 | 0 | 2 | 0 | 0 | 0 | 0 | 0 | 0 | 0 | 1 | 1 | 0 | 0 | 0 | 0 | 0 | 0 | 0 | 0 |
| PREEMERGENCE | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 9 | 5 | 10 | 0 | 1 | 10 | 0 | 10 | 9 | 4 | 10 | 10 | 7 | 9 | 1 | 1 | 10 | 10 | 10 | 10 | 10 | 9 | 6 |
| Bedstraw | 0 | 0 | 0 | 0 | — | — | — | 0 | 0 | 0 | 0 | 0 | 0 | 0 | 0 | 0 | 0 | 0 | 0 | 0 | 0 | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cheatgrass | 0 | 0 | 0 | 0 | 2 | 0 | 0 | 0 | 0 | 0 | 0 | 0 | 0 | 0 | 0 | 0 | 0 | 0 | 0 | 0 | 0 | 0 | 0 |
| Chickweed | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Giant foxtail | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Lambsquarters | 0 | 0 | 0 | 0 | 0 | 0 | 0 | 0 | 3 | 0 | 0 | 0 | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 |
| Nutsedge | 0 | 4 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 2 | 0 | 0 | 0 | 0 | 0 | 0 | 0 | 0 | 0 | 0 | 0 | 0 | 0 | 0 | 0 | 3 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rate (400 g/ha) | | | | | | | | | | | | | | | | | | | | | | | |
| POSTEMERGENCE | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 9 | 3 | 10 | 0 | 0 | 10 | 1 | 10 | 9 | 2 | 10 | 10 | 10 | 2 | 10 | 1 | 1 | 9 | 10 | 10 | 10 | 10 | 3 | 2 |
| Bedstraw | 0 | 0 | 0 | 0 | 0 | 2 | 0 | 0 | 0 | 0 | 0 | 0 | 0 | 0 | 0 | 0 | 0 | 0 | — | 0 | 0 | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — |
| Cheatgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Chickweed | 0 | 0 | 0 | 0 | 0 | 0 | 0 | 0 | — | 0 | 0 | 0 | 0 | — | — | 0 | 0 | 0 | 0 | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 |
| Crabgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Giant foxtail | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 |
| Lambsquarters | 0 | — | 0 | — | 0 | 0 | 0 | 0 | 0 | 0 | 0 | 0 | 0 | — | 0 | 0 | 0 | 0 | 0 | 0 | 0 | 0 | — |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Pace | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 2 | 0 | 0 |
| Sugar beet | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | — | 0 | 0 | 0 | 0 | 0 | 0 | 0 | 0 | 0 | 0 | 0 | 0 | 0 | 0 | 0 | 0 | 0 | 0 | 0 | — | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | — | 0 | 0 | 0 | — | — | — | 0 | 0 | 0 | 0 | 0 | — | 0 | 0 | — | — | 0 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| PREEMERGENCE | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 9 | 3 | 10 | 0 | 0 | 9 | 0 | 10 | 9 | 2 | 10 | 7 | 10 | 2 | 10 | 1 | 0 | 10 | 10 | 10 | 10 | 10 | 6 | 4 |
| Bedstraw | 0 | 0 | 0 | 0 | — | 0 | — | 0 | 0 | 0 | — | 0 | — | 0 | 0 | 0 | 0 | 0 | 0 | 0 | 0 | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cheatgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Chickweed | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cocklebur | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Giant foxtail | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Lambsquarters | 0 | 0 | 0 | 0 | 0 | 0 | 0 | 0 | 0 | 0 | 0 | 0 | 0 | 0 | 0 | 0 | 0 | 0 | 0 | — | — | — | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | — | — | 0 | 0 | 0 | 0 | 0 | 0 | 0 | 0 | 0 | — | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Pace | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | — | 0 | 0 | 0 | 0 | 0 | 0 | — | 0 | 0 | 0 | 0 | 0 | 0 | 0 | 0 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | | | | | | | |
|---|---|---|---|---|---|---|---|---|---|---|---|---|---|---|---|---|---|---|---|---|---|---|---|
| | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 |
| Rate (2000 g/ha) | | | | | | | | | | | | | | | | | | | | | | | |
| POSTEMERGENCE | | | | | | | | | | | | | | | | | | | | | | | |
| Barley | 0 | 0 | 0 | 2 | 0 | 0 | 0 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | | | |
|---|---|---|---|---|---|---|---|---|---|---|---|---|---|---|---|---|---|---|---|---|---|---|---|
| Barnyardgrass | 4 | 9 | 2 | 4 | 9 | 3 | 0 | 8 | 3 | 7 | 5 | 2 | 10 | 10 | 10 | 5 | 10 | 3 | 10 | 5 | 10 | 4 | 6 |
| Bedstraw | 0 | 0 | 0 | 0 | 0 | 0 | 0 | 0 | 0 | 0 | 0 | 0 | 0 | 0 | 0 | 0 | 0 | 0 | 0 | 2 | 1 | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cheatgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Chickweed | 0 | 0 | 0 | 0 | 1 | 0 | 0 | 0 | 0 | 0 | 0 | 0 | 0 | 0 | 0 | 0 | 0 | 0 | 0 | 1 | 0 | 0 | 0 |
| Cocklebur | — | 0 | 0 | 0 | 0 | 0 | 0 | 0 | 0 | 0 | 0 | 0 | 0 | 0 | 0 | 0 | 0 | 0 | 4 | 3 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 |
| Cotton | 0 | 0 | 0 | 4 | 0 | 0 | 0 | 2 | 0 | 3 | 0 | 0 | 0 | 0 | 0 | 0 | 0 | 0 | 0 | 5 | 0 | 3 | 0 |
| Crabgrass | 0 | 0 | 1 | 1 | 0 | 0 | 0 | 1 | 0 | 0 | 0 | 0 | 0 | 0 | 0 | 0 | 0 | 0 | 3 | 1 | 0 | — | 0 |
| Giant foxtail | 0 | 0 | 1 | 1 | 0 | 0 | 0 | 1 | 2 | 2 | 0 | 0 | 0 | 0 | 0 | 0 | 0 | 0 | 2 | 2 | 0 | 0 | 0 |
| Lambsquarters | 0 | 0 | 0 | 0 | 1 | 0 | 0 | 0 | 0 | 0 | 0 | 0 | 1 | 0 | 0 | 1 | 1 | 0 | 0 | 2 | 1 | 0 | 0 |
| Morningglory | 0 | 0 | 0 | 0 | 0 | 0 | 0 | 0 | 2 | 0 | 0 | 0 | 0 | 0 | 0 | 0 | 0 | 0 | 1 | 1 | 0 | 2 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 |
| Rice | 0 | 0 | 2 | 0 | 0 | 0 | 0 | 0 | 0 | 0 | 0 | 0 | 0 | 0 | 0 | 0 | 0 | 0 | 2 | 1 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 2 | 1 | 0 | 0 | 0 |
| Soybean | 0 | 0 | 0 | 2 | 0 | 0 | 0 | 0 | 0 | 0 | 0 | 0 | 0 | 0 | 0 | 0 | 0 | 0 | 0 | 2 | 0 | 0 | 0 |
| Sugar beet | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 0 |
| Velvetleaf | 0 | 0 | 0 | 0 | 2 | 0 | 0 | 0 | 0 | 0 | 0 | 0 | 0 | 0 | 0 | 1 | 0 | 0 | 0 | 1 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | 0 | 0 | — | 0 | 0 | 0 | 0 | 0 | 0 | 0 | 0 | 0 | 0 | 0 | 0 | 0 | 0 | 1 | 1 | 0 | |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| PREEMERGENCE | | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 7 | 9 | 2 | 4 | 7 | 5 | 0 | 9 | 6 | 9 | 7 | 3 | 9 | 10 | 10 | 5 | 10 | 2 | 10 | 2 | 10 | 4 | 5 |
| Bedstraw | 0 | 0 | 0 | 0 | 0 | 0 | 0 | 0 | 0 | — | 0 | 0 | 0 | 0 | 0 | 0 | 0 | 0 | 0 | 0 | 0 | 4 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cheatgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Chickweed | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cocklebur | 0 | — | 0 | 0 | 0 | 0 | 0 | 0 | 0 | 0 | — | 0 | 0 | 0 | 0 | 0 | 0 | 0 | 10 | 0 | 0 | — | 0 |
| Corn | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cotton | 0 | 0 | 0 | 3 | 0 | 0 | 0 | 0 | 0 | 0 | 0 | 0 | 0 | 0 | 0 | 0 | 0 | 0 | 0 | 0 | 0 | 0 | 0 |
| Crabgrass | 0 | 0 | 0 | 2 | 0 | 0 | 0 | 0 | 0 | 0 | 0 | 0 | 0 | 0 | 0 | 0 | 0 | 0 | 3 | 0 | 0 | 0 | 0 |
| Giant foxtail | 0 | 0 | 0 | 2 | 0 | 0 | 0 | 0 | 0 | 0 | 0 | 0 | 0 | 0 | 0 | 0 | 0 | 0 | 2 | 0 | 0 | 0 | 0 |
| Lambsquarters | 0 | 0 | 0 | 0 | 0 | 0 | 0 | 0 | 0 | 0 | 0 | — | 0 | 0 | 0 | 0 | 0 | 0 | — | 0 | 0 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| Nutsedge | 0 | — | 0 | 0 | 0 | 0 | 0 | 0 | 0 | 0 | 0 | 0 | 0 | 0 | 0 | 0 | 0 | 0 | 4 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 2 | 0 | 0 | 0 | 0 | 0 | 0 | 0 | 0 | 0 | 0 | 0 | 0 | 0 | 1 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | 0 | — | 0 | 0 | 0 | 0 | 0 | 0 | 0 | 0 | 0 | 0 | 0 | 0 | 0 | 0 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rate (400 g/ha) | | | | | | | | | | | | | | | | | | | | | | | | |
| POSTEMERGENCE | | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 2 | 6 | 1 | 2 | 6 | 2 | 0 | 4 | 0 | 3 | 3 | 0 | 7 | 10 | 10 | 5 | 10 | 2 | 10 | 1 | 10 | 2 | 2 |
| Bedstraw | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cheatgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Chickweed | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cocklebur | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 |
| Corn | 0 | 0 | 0 | 0 | 0 | 0 | 0 | 0 | 0 | 0 | 0 | 0 | — | 0 | 0 | 0 | 0 | 0 | 0 | 1 | 0 | 0 | 0 |
| Cotton | 0 | 0 | 0 | 2 | 0 | 0 | 0 | 0 | 0 | 0 | 0 | 0 | 0 | 0 | 0 | 0 | 0 | 0 | 0 | 1 | 0 | 0 | 0 |
| Crabgrass | — | 0 | 1 | 0 | 0 | 0 | 0 | 0 | 0 | 0 | 0 | 0 | 0 | 0 | 0 | 0 | 0 | 0 | 2 | 1 | 0 | 0 | 0 |
| Giant foxtail | 0 | 0 | 1 | 0 | 0 | 0 | 0 | 0 | 0 | 0 | 0 | 0 | 0 | 0 | 0 | 0 | 0 | 0 | 2 | 1 | 0 | 0 | 0 |
| Lambsquarters | — | — | 0 | 0 | 0 | 0 | 0 | 0 | 0 | 0 | 0 | 0 | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 |
| Nutsedge | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 2 | 1 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| PREEMERGENCE | | | | | | | | | | | | | | | | | | | | | | | | |
| Barley | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 3 | 9 | 1 | 4 | 5 | 2 | 0 | 6 | 5 | 9 | 3 | 2 | 7 | 9 | 10 | 5 | 10 | 1 | 10 | 0 | 10 | 2 | 0 |
| Bedstraw | 0 | 0 | 0 | 0 | 0 | 0 | 0 | 0 | 0 | 0 | 0 | 0 | 0 | 0 | 0 | 0 | 0 | 0 | 0 | 0 | 0 | 3 | 0 |
| Blackgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cheatgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Chickweed | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Cocklebur | 0 | 0 | 0 | 0 | 0 | 0 | 0 | — | 0 | 0 | 0 | 0 | 0 | 0 | 0 | 0 | 0 | 0 | 10 | 0 | 0 | 0 | 0 |
| Corn | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 |

TABLE B-continued

| | | | | | | | | | | | | | | | | | | | | | | | |
|---|---|---|---|---|---|---|---|---|---|---|---|---|---|---|---|---|---|---|---|---|---|---|---|
| Crabgrass | 0 | 0 | 0 | 2 | 0 | 0 | 0 | 0 | 0 | 0 | 0 | 0 | 0 | 0 | 0 | 0 | 0 | 0 | 3 | 0 | 0 | 0 | 0 |
| Giant foxtail | 0 | 0 | 0 | 2 | 0 | 0 | 0 | 0 | 0 | 0 | 0 | 0 | 0 | 0 | 0 | 0 | 0 | 0 | 2 | 0 | 0 | 0 | 0 |
| Lambsquarters | 0 | — | 0 | 0 | 0 | 0 | 0 | 0 | 0 | 0 | 0 | 0 | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 | 0 | 0 | 0 | 0 | 0 | 0 | 0 | 2 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

| | COMPOUND | | | | | | | | | | |
|---|---|---|---|---|---|---|---|---|---|---|---|
| | 49 | 50 | 51 | 52 | 53 | 54 | 55 | 56 | 57 | 58 | 59 |
| Rate (2000 g/ha) | | | | | | | | | | | |
| POSTEMERGENCE | | | | | | | | | | | |
| Barley | 0 | | | | | | | | | | 0 |
| Barnyardgrass | 7 | | | | | | | | | | 10 |
| Bedstraw | 0 | | | | | | | | | | 0 |
| Blackgrass | 0 | | | | | | | | | | 3 |
| Cheatgrass | 0 | | | | | | | | | | 0 |
| Chickweed | 0 | | | | | | | | | | 0 |
| Cocklebur | 0 | | | | | | | | | | — |
| Corn | 0 | | | | | | | | | | 0 |
| Cotton | 0 | | | | | | | | | | 0 |
| Crabgrass | 2 | | | | | | | | | | 2 |
| Giant foxtail | 1 | | | | | | | | | | 0 |
| Lambsquarters | 0 | | | | | | | | | | — |
| Morningglory | 0 | | | | | | | | | | 2 |
| Nutsedge | 0 | | | | | | | | | | 0 |
| Rape | 0 | | | | | | | | | | 0 |
| Rice | 0 | | | | | | | | | | 0 |
| Sorghum | 0 | | | | | | | | | | 0 |
| Soybean | 0 | | | | | | | | | | 0 |
| Sugar beet | 0 | | | | | | | | | | 0 |
| Velvetleaf | 3 | | | | | | | | | | 0 |
| Wheat | 0 | | | | | | | | | | 0 |
| Wild buckwheat | 0 | | | | | | | | | | 0 |
| Wild oat | 0 | | | | | | | | | | 0 |
| PREEMERGENCE | | | | | | | | | | | |
| Barley | 0 | | | | | | | | | | 0 |
| Barnyardgrass | 6 | | | | | | | | | | 10 |
| Bedstraw | 0 | | | | | | | | | | 0 |
| Blackgrass | 0 | | | | | | | | | | 0 |
| Cheatgrass | 0 | | | | | | | | | | 0 |
| Chickweed | 0 | | | | | | | | | | — |
| Cocklebur | — | | | | | | | | | | — |
| Corn | 2 | | | | | | | | | | 0 |
| Cotton | 0 | | | | | | | | | | 0 |
| Crabgrass | 3 | | | | | | | | | | 0 |
| Giant foxtail | 2 | | | | | | | | | | 0 |
| Lambsquarters | 0 | | | | | | | | | | 0 |
| Morningglory | 0 | | | | | | | | | | 1 |
| Nutsedge | 0 | | | | | | | | | | 0 |
| Rape | 0 | | | | | | | | | | 0 |
| Rice | 1 | | | | | | | | | | 0 |
| Sorghum | 0 | | | | | | | | | | 0 |
| Soybean | 0 | | | | | | | | | | 0 |
| Sugar beet | 0 | | | | | | | | | | 0 |
| Velvetleaf | 0 | | | | | | | | | | 0 |
| Wheat | 0 | | | | | | | | | | 0 |
| Wild buckwheat | 0 | | | | | | | | | | 0 |
| Wild oat | 0 | | | | | | | | | | 0 |
| Rate (400 g/ha) | | | | | | | | | | | |
| POSTEMERGENCE | | | | | | | | | | | |
| Barley | 0 | 0 | 0 | 0 | 0 | 0 | 0 | 0 | 0 | 0 | 0 |
| Barnyardgrass | 4 | 2 | 6 | 8 | 10 | 10 | 10 | 3 | 10 | 10 | 10 |
| Bedstraw | 0 | 0 | 0 | 0 | 0 | 0 | 0 | 0 | 0 | 0 | 0 |
| Blackgrass | 0 | 0 | 0 | 0 | 0 | 0 | 0 | 0 | 0 | 0 | 0 |
| Cheatgrass | 0 | 0 | 0 | 0 | 0 | 0 | 0 | 0 | 0 | 0 | 0 |
| Chickweed | 0 | 0 | 0 | 0 | 0 | 0 | 0 | 0 | 0 | 0 | 0 |
| Cocklebur | 0 | 0 | 0 | 0 | 0 | 0 | 0 | 0 | 0 | 0 | — |
| Corn | 0 | 0 | 0 | 0 | 0 | 0 | 0 | 0 | 0 | 0 | 0 |
| Cotton | 0 | 3 | 8 | 0 | 0 | 0 | 0 | 0 | 0 | 0 | 0 |
| Crabgrass | 0 | 0 | 0 | 0 | 0 | 0 | 0 | 0 | 0 | 0 | 0 |
| Giant foxtail | 0 | 0 | 0 | 0 | 0 | 0 | 0 | 0 | 0 | 0 | 0 |
| Lambsquarters | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 |

TABLE B-continued

| | | | | | | | | | | | |
|---|---|---|---|---|---|---|---|---|---|---|---|
| Nutsedge | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 |
| Rice | 0 | 0 | 2 | 0 | 0 | 0 | 0 | 0 | 0 | 0 | 0 |
| Sorghum | 0 | 0 | 0 | 0 | 0 | 0 | 0 | 0 | 0 | 0 | 0 |
| Soybean | 0 | 2 | 0 | 0 | 0 | 0 | 0 | 0 | 0 | 0 | 0 |
| Sugar beet | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 |
| Wild buckwheat | 0 | 0 | 0 | 0 | 0 | 0 | 0 | 0 | 0 | 0 | 0 |
| Wild oat | 0 | 0 | 0 | 0 | 0 | 0 | 0 | 0 | 0 | 0 | 0 |
| PREEMERGENCE | | | | | | | | | | | |
| Barley | 0 | 0 | 0 | 0 | 0 | 0 | 0 | 0 | 0 | 0 | 0 |
| Barnyardgrass | 4 | 1 | 8 | 3 | 10 | 10 | 10 | 4 | 10 | 10 | 9 |
| Bedstraw | 0 | 0 | 0 | 0 | 0 | 0 | 0 | 0 | 0 | 0 | 0 |
| Blackgrass | 0 | 0 | 0 | 0 | 0 | 0 | 0 | 0 | 0 | 0 | 0 |
| Cheatgrass | 0 | 0 | 0 | 0 | 0 | 0 | 0 | 0 | 0 | 0 | 0 |
| Chickweed | 0 | 0 | 0 | — | 0 | 0 | 0 | 0 | 0 | 0 | 9 |
| Cocklebur | 0 | 0 | 0 | 0 | 0 | 0 | 0 | 0 | 0 | 0 | 0 |
| Corn | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 |
| Crabgrass | 2 | 2 | 0 | 0 | 0 | 0 | 0 | 0 | 0 | 0 | 0 |
| Giant foxtail | 0 | 3 | 0 | 0 | 0 | 0 | 0 | 0 | 0 | 0 | 0 |
| Lambsquarters | 0 | 0 | 0 | 0 | 0 | 0 | 0 | 0 | 0 | 0 | 0 |
| Morningglory | 0 | 0 | 0 | 0 | 0 | 0 | 0 | 0 | 0 | 0 | 0 |
| Nutsedge | 0 | 0 | 0 | 0 | 0 | 0 | 0 | 0 | 0 | 0 | 0 |
| Rape | 0 | 0 | 0 | 0 | 0 | 0 | 0 | 0 | 0 | 0 | 0 |
| Rice | 0 | 0 | 1 | 0 | 0 | 0 | 0 | 0 | 0 | 0 | 0 |
| Sorghum | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 |
| Sugar beet | 0 | 0 | 0 | 0 | 0 | 0 | 0 | 0 | 0 | 0 | 0 |
| Velvetleaf | 0 | 0 | 0 | 0 | 0 | 0 | 0 | 0 | 0 | 0 | 0 |
| Wheat | 0 | 0 | 0 | 0 | 0 | 0 | 0 | 0 | 0 | 0 | 0 |
| Wild buckwheat | 0 | 0 | 0 | 0 | 0 | 0 | 0 | 0 | 0 | 0 | 0 |
| Wild oat | 0 | 0 | 0 | 0 | 0 | 0 | 0 | 0 | 0 | 0 | 0 |

Rate (100 g/ha)

| | | | | | | | | | |
|---|---|---|---|---|---|---|---|---|---|
| POSTEMERGENCE | | | | | | | | | |
| Barley | 0 | 0 | 0 | 0 | 0 | 0 | 0 | 0 | 0 |
| Barnyardgrass | 2 | 4 | 5 | 7 | 10 | 10 | 2 | 9 | 10 |
| Bedstraw | 0 | 0 | 0 | 0 | 0 | 0 | 0 | 0 | 0 |
| Blackgrass | 0 | 0 | 0 | 0 | 0 | 0 | 0 | 0 | 0 |
| Cheatgrass | 0 | 0 | 0 | 0 | 0 | 0 | 0 | 0 | 0 |
| Chickweed | 0 | 0 | 0 | 0 | 0 | 0 | 0 | 0 | 0 |
| Cocklebur | 0 | 0 | 0 | 0 | 0 | 0 | 0 | 0 | 0 |
| Corn | 0 | 0 | 0 | 0 | 0 | 0 | 0 | 0 | 0 |
| Cotton | 2 | 6 | 0 | 0 | 0 | 0 | 0 | 0 | 0 |
| Crabgrass | 0 | 0 | 0 | 0 | 0 | 0 | 0 | 0 | 0 |
| Giant foxtail | 0 | 0 | 0 | 0 | 0 | 0 | 0 | 0 | 0 |
| Lambsquarters | 0 | 0 | 0 | 0 | 0 | 0 | 0 | 0 | 0 |
| Morningglory | 0 | 0 | 0 | 0 | 0 | 0 | 0 | 0 | 0 |
| Nutsedge | 0 | 0 | 0 | 0 | 0 | 0 | 0 | 0 | 0 |
| Rape | 0 | 0 | 0 | 0 | 0 | 0 | 0 | 0 | 0 |
| Rice | 0 | 0 | 0 | 0 | 0 | 0 | 0 | 0 | 0 |
| Sorghum | 0 | 0 | 0 | 0 | 0 | 0 | 0 | 0 | 0 |
| Soybean | 0 | 0 | 0 | 0 | 0 | 0 | 0 | 0 | 0 |
| Sugar beet | 0 | 0 | 0 | 0 | 0 | 0 | 0 | 0 | 0 |
| Velvetleaf | 0 | 0 | 0 | 0 | 0 | 0 | 0 | 0 | 0 |
| Wheat | 0 | 0 | 0 | 0 | 0 | 0 | 0 | 0 | 0 |
| Wild buckwheat | 0 | 0 | 0 | 0 | 0 | 0 | 0 | 0 | 0 |
| Wild oat | 0 | 0 | 0 | 0 | 0 | 0 | 0 | 0 | 0 |
| PREEMERGENCE | | | | | | | | | |
| Barley | 0 | 0 | 0 | 0 | 0 | 0 | 0 | 0 | 0 |
| Barnyardgrass | 0 | 4 | 3 | 9 | 10 | 10 | 3 | 10 | 10 |
| Bedstraw | 0 | 0 | 0 | 0 | 0 | 0 | 0 | 0 | 0 |
| Blackgrass | 0 | 0 | 0 | 0 | 0 | 0 | 0 | 0 | 0 |
| Cheatgrass | 0 | 0 | 0 | — | 0 | 0 | 0 | 0 | 0 |
| Chickweed | 0 | 0 | 0 | — | 0 | 0 | 0 | 0 | 0 |
| Cocklebur | 0 | 0 | 0 | 0 | 0 | 0 | 0 | 0 | 0 |
| Corn | 0 | 0 | 0 | 0 | 0 | 0 | 0 | 0 | 0 |
| Cotton | 0 | 0 | 0 | 0 | 0 | 0 | 0 | 0 | 0 |
| Crabgrass | 0 | 0 | 0 | 0 | 0 | 0 | 0 | 0 | 0 |
| Giant foxtail | 0 | 0 | 0 | 0 | 0 | 0 | 0 | 0 | 0 |
| Lambsquarters | — | — | 0 | 0 | 0 | 0 | 0 | 0 | 0 |
| Morningglory | 0 | 0 | 0 | 0 | 0 | 0 | 0 | 0 | 0 |
| Nutsedge | 0 | 0 | 0 | 0 | 0 | 0 | 0 | 0 | 0 |
| Rape | 0 | 0 | 0 | 0 | 0 | 0 | — | 0 | 0 |
| Rice | 0 | 0 | 0 | 0 | 0 | 0 | 0 | 0 | 0 |
| Sorghum | 0 | 0 | 0 | 0 | 0 | 0 | 0 | 0 | 0 |
| Soybean | 0 | 0 | 0 | 0 | 0 | 0 | 0 | 0 | 0 |
| Sugar beet | 0 | 0 | 0 | 0 | — | 0 | 0 | 0 | 0 |
| Velvetleaf | 0 | 0 | 0 | 0 | 0 | 0 | 0 | 0 | 0 |
| Wheat | 0 | 0 | 0 | 0 | 0 | 0 | 0 | 0 | 0 |

TABLE B-continued

|  | | | | | | | | | |
|---|---|---|---|---|---|---|---|---|---|
| Wild buckwheat | 0 | 0 | 0 | 0 | 0 | 0 | 0 | 0 | 0 |
| Wild oat | 0 | — | 0 | 0 | 0 | 0 | 0 | 0 | 0 |

TEST C

The test chemicals were formulated in a non-phytoxic solvent and applied to water that covered the soil surface (flood application). Seeds of barnyardgrass (*Echinochloa crus-galli*), rice (*Oryza sativa*), umbrella sedge (*Cyperus difformis*) and duck salad (*Heteranthera limosa*) were planted in silt loam soil in separate containers. Containers of duck salad and umbrella sedge were flooded with water 2.5 cm above the soil level immediately after planting and grown for fourteen days prior to treatment. The containers of barnyardgrass and rice were grown for ten days (barnyardgrass at 2 leaf stage) and flooded one day prior to treatment. Water depth was maintained at approximately 2.5 cm for the duration of the test.

All plant species were grown using normal greenhouse practices. Treated plants were compared to untreated controls and visually evaluated eleven to fifteen days after treatment. Plant response ratings, summarized in Table C, were recorded on a 0 to 10 scale where 0 is no effect and 10 is complete control. A dash (-) response means no test result.

TABLE C

|  | COMPOUND | | | | |
|---|---|---|---|---|---|
|  | 1 | 3 | 21 | 43 | 59 |
| POSTEMERGENCE | | | | | |
| Rate (1000 g/ha) | | | | | |
| Duck salad | 0 | | | | 0 |
| Barnyardgrass | 10 | | | | 10 |
| Rice Japonica | 0 | | | | 1 |
| Umbrella sedge | 0 | | | | 0 |
| Rate (500 g/ha) | | | | | |
| Duck salad | 0 | 0 | 0 | | 0 |
| Barnyardgrass | 10 | 10 | 10 | | 10 |
| Rice Japonica | 0 | 0 | 0 | | 0 |
| Umbrella sedge | 0 | 0 | 0 | | 0 |
| Rate (250 g/ha) | | | | | |
| Duck salad | 0 | 0 | | | 0 |
| Barnyardgrass | 9 | 10 | | | 9 |
| Price Japonica | 0 | 0 | | | 0 |
| Umbrella sedge | 0 | 0 | | | 0 |
| Rate (125 g/ha) | | | | | |

TABLE C-continued

|  | COMPOUND | | | | |
|---|---|---|---|---|---|
|  | 1 | 3 | 21 | 43 | 59 |
| Duck salad | 0 | 0 | 0 | — | 0 |
| Barnyardgrass | 9 | 10 | 10 | 10 | 9 |
| Rice Japonica | 0 | 0 | 0 | 1 | 0 |
| Umbrella sedge | 0 | 0 | 0 | — | 0 |
| Rate (62 g/ha) | | | | | |
| Duck salad |  | 0 |  |  | 0 |
| Barnyardgrass |  | 10 |  |  | 7 |
| Rice Japonica |  | 0 |  |  | 0 |
| Umbrella sedge |  | 0 |  |  | 0 |
| Rate (31 g/ha) | | | | | |
| Duck salad |  |  | 0 | — |  |
| Barnyardgrass |  |  | 10 | 10 |  |
| Price Japonica |  |  | 0 | 0 |  |
| Umbrella sedge |  |  | 0 | — |  |
| Rate (8 g/ha) | | | | | |
| Duck salad |  |  | 0 | — |  |
| Barnyardgrass |  |  | 10 | 8 |  |
| Rice Japonica |  |  | 0 | 0 |  |
| Umbrella sedge |  |  | 0 | — |  |
| Rate (2 g/ha) | | | | | |
| Barnyardgrass |  |  |  | 5 |  |
| Rice Japonica |  |  |  | 0 |  |

TEST D

Plastic pots were partially filled with silt loam soil. The soil was then flooded with water, Japonica rice (*Oryza sativa*) sprouted seeds and 1.5 leaf transplants were planted in the soil. Seeds of barnyardgrass (*Echinochloa crus-galli*) were planted in saturated soil and plants grown to the 1 leaf, 2 leaf and 3 leaf stages for testing. At testing, the water level for all plantings was raised to 2 cm above the soil surface. Cal. Watergrass (*E. oryzoides*) was also planted. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table D are reported on a 0 to 10 scale where 0 is no effect and 10 is complete control. A dash (-) response means no test result.

TABLE D

|  | COMPOUND | | | | | | | | | | | | | | | | |
|---|---|---|---|---|---|---|---|---|---|---|---|---|---|---|---|---|---|
|  | 1 | 3 | 13 | 37 | 41 | 43 | 45 | 53 | 54 | 55 | 57 | 58 | 59 | 65 | 66 | 80 | 81 |
| PADDY | | | | | | | | | | | | | | | | | |
| Rate (1000 g/ha) | | | | | | | | | | | | | | | | | |
| 1-LF B.Y. Grass | — | — | — | | | | | | | | | | 10 | | | | |
| 2-LF B.Y. Grass | 9 | 10 | 10 | | | | | | | | | | 10 | | | | |
| 3-Lf B.Y. Grass | 9 | 10 | 10 | | | | | | | | | | 10 | | | | |
| Jap Direct Seed | 0 | 1 | 0 | | | | | | | | | | 0 | | | | |
| Jap Rice Eff | 0 | 0 | 0 | | | | | | | | | | 0 | | | | |
| Rate (500 g/ha) | | | | | | | | | | | | | | | | | |
| 1-LF B.Y. Grass | — | — | — | | | | | | | | | | 10 | | | | |
| 2-LF B.Y. Grass | 9 | 10 | 10 | | | | | | | | | | 10 | | | | |
| 3-Lf B.Y. Grass | 9 | 10 | 10 | | | | | | | | | | 10 | | | | |
| Jap Direct Seed | 0 | 0 | 0 | | | | | | | | | | 0 | | | | |
| Jap Rice Eff | 0 | 0 | 0 | | | | | | | | | | 0 | | | | |
| Rate (250 g/ha) | | | | | | | | | | | | | | | | | |
| 1-LF B.Y. Grass | — | — | — | | | | | | | | | | 10 | | | | |
| 2-LF B.Y. Grass | 9 | 10 | 10 | | | | | | | | | | 10 | | | | |
| 3-Lf B.Y. Grass | 8 | 10 | 10 | | | | | | | | | | 10 | | | | |
| Jap Direct Seed | 0 | 0 | 1 | | | | | | | | | | 0 | | | | |
| Jap Rice Eff | 0 | 0 | 0 | | | | | | | | | | 0 | | | | |
| Rate (125 g/ha) | | | | | | | | | | | | | | | | | |

TABLE D-continued

| | COMPOUND | | | | | | | | | | | | | | | |
|---|---|---|---|---|---|---|---|---|---|---|---|---|---|---|---|---|
| | 1 | 3 | 13 | 37 | 41 | 43 | 45 | 53 | 54 | 55 | 57 | 58 | 59 | 65 | 66 | 80 | 81 |
| 1-LF B.Y. Grass | — | — | — | | | | | | | | | | 10 | | | | |
| 2-LF B.Y. Grass | 8 | 10 | 10 | | | | | | | | | | 10 | | | | |
| 3-Lf B.Y. Grass | 7 | 10 | 10 | | | | | | | | | | 10 | | | | |
| Jap Direct Seed | 0 | 0 | 1 | | | | | | | | | | 0 | | | | |
| Jap Rice Eff | 0 | 1 | 0 | | | | | | | | | | 0 | | | | |
| Rate (64 g/ha) | | | | | | | | | | | | | | | | | |
| 1-LF B.Y. Grass | — | — | — | — | | | | — | — | — | — | — | 9 | — | — | — | — |
| 2-LF B.Y. Grass | 7 | 10 | 10 | — | | | | — | — | — | — | — | 10 | — | — | — | — |
| 3-LF Watergrass | — | — | — | 9 | | 8 | 7 | 8 | | 9 | 9 | — | 0 | 0 | 8 | 8 |
| 3-Lf B.Y. Grass | 6 | 10 | 10 | 10 | | 10 | 10 | 10 | | 10 | 10 | 10 | 0 | 0 | 10 | 10 |
| Jap Direct Seed | 0 | 1 | 1 | 0 | | 0 | 0 | 0 | | 0 | 0 | 0 | 0 | 1 | 0 | 0 |
| Jap Rice Eff | 0 | 0 | 0 | — | | — | — | — | — | — | — | 0 | — | — | — | — |
| Rate (32 g/ha) | | | | | | | | | | | | | | | | | |
| 2-LF B.Y. Grass | 9 | 10 | — | 10 | — | — | — | — | — | — | — | — | 9 | — | — | — | — |
| 3-LF Watergrass | — | — | 0 | 9 | 5 | 7 | 5 | 6 | 8 | 8 | 8 | — | 0 | 0 | 6 | 7 |
| 3-Lf B.Y. Grass | 10 | 10 | 5 | 10 | 10 | 10 | 10 | 10 | 10 | 10 | 10 | 10 | 0 | 0 | 9 | 10 |
| Jap Direct Seed | 0 | 1 | 0 | 5 | 0 | 0 | 0 | 0 | 0 | 0 | 0 | 0 | 0 | 0 | 0 | 0 |
| Jap Rice Eff | 0 | 1 | 0 | 0 | 0 | 0 | — | — | — | — | — | 0 | — | — | — | — |
| Rate (16 g/ha) | | | | | | | | | | | | | | | | | |
| 2-LF B.Y. Grass | 9 | 10 | — | 10 | — | — | — | — | — | — | — | — | 9 | — | — | — | — |
| 3-LF Watergrass | — | — | 0 | 8 | 3 | 4 | 3 | 5 | 8 | 7 | 7 | — | 0 | 0 | 8 | 6 |
| 3-Lf B.Y. Grass | 9 | 10 | 3 | 10 | 10 | 10 | 7 | 10 | 10 | 8 | 10 | 10 | 0 | 0 | 10 | 9 |
| Jap Direct Seed | 0 | 1 | 0 | 5 | 0 | 0 | 0 | 0 | 0 | 0 | 0 | 0 | 0 | 0 | 0 | 0 |
| Jap Price Eff | 0 | 0 | 0 | 0 | 0 | 0 | — | — | — | — | — | 0 | — | — | — | — |
| Rate (8 g/ha) | | | | | | | | | | | | | | | | | |
| 2-LF B.Y. Grass | 8 | 10 | — | 10 | — | — | — | — | — | — | — | — | 9 | — | — | — | — |
| 3-LF Watergrass | — | — | 0 | 9 | 1 | 4 | 1 | 6 | 7 | 6 | 6 | — | 0 | 0 | 8 | 2 |
| 3-Lf B.Y. Grass | 8 | 9 | 1 | 10 | 9 | 10 | 6 | 10 | 10 | 9 | 9 | 9 | 0 | 0 | 10 | 9 |
| Jap Direct Seed | 0 | 0 | 0 | 0 | 0 | 0 | 0 | 0 | 0 | 0 | 0 | 0 | 0 | 0 | 0 | 0 |
| Jap Rice Eff | 0 | 0 | 0 | 0 | 0 | 0 | — | — | — | — | — | 0 | — | — | — | — |
| Rate (4 g/ha) | | | | | | | | | | | | | | | | | |
| 2-LF B.Y. Grass | 6 | 10 | — | 10 | — | — | — | — | — | — | — | — | 9 | — | — | — | — |
| 3-LF Watergrass | — | — | 0 | 8 | 1 | 3 | 1 | 5 | 4 | 3 | 4 | — | 0 | 0 | 6 | 1 |
| 3-Lf B.Y. Grass | 5 | 9 | 3 | 10 | 6 | 9 | 3 | 10 | 10 | 4 | 7 | 9 | 0 | 0 | 10 | 5 |
| Jap Direct Seed | 0 | 0 | 0 | 0 | 0 | 0 | 0 | 0 | 0 | 0 | 0 | 0 | 0 | 0 | 0 | 0 |
| Jap Rice Eff | 0 | 0 | 0 | 0 | 0 | 0 | — | — | — | — | — | 0 | — | — | — | — |
| Rate (2 g/ha) | | | | | | | | | | | | | | | | | |
| 2-LF B.Y. Grass | 0 | — | — | 10 | — | — | | | | | | | | | | | |
| 3-LF Watergrass | — | — | 0 | 5 | 1 | 3 | | | | | | | | | | | |
| 3-Lf B.Y. Grass | 4 | 4 | 4 | 10 | 3 | 9 | | | | | | | | | | | |
| Jap Direct Seed | 0 | 0 | 0 | 0 | 0 | 0 | | | | | | | | | | | |
| Jap Face Eff | 0 | 0 | 0 | 0 | 0 | 0 | | | | | | | | | | | |

TESTS E, F AND G (MIXTURES)

Plastic pots were partially filled with silt loam soil. The soil was then flooded with water, Japonica rice (*Oryza sativa*) sprouted seeds and 1.5 leaf transplants were planted in the soil. Seeds of barnyardgrass (*Echinochloa crus-galli*) were planted in saturated soil and plants grown to the 1 leaf, 2 leaf and 3 leaf (31f) stages for testing. At testing, the water level for all plantings was raised to 2 cm above the soil surface. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table E are reported on a 0 to 100 scale where 0 is no effect and 100 is complete control. A dash (-) response means no test result.

Numbers in parenthesis are the predicted activity of mixture by Colby equation $$A(1,2) = A(1) + A(2) - A(1) \times A(2)/100$$

where A(1) and A(2) are activity of compound "1" and "2", respectively; A(1,2) is the predicted activity for mixture containing "1" and "2".

TEST E

TABLE E1

Compounds 41, 89, 88, and 86 on Cal. Watergrass (*E. oryzoides*) in soil from Japan (Toride Lt Clay) at the 31f stage.

| Compound No. | Rate g/ha | % Control |
|---|---|---|
| Untreated Check | 0 | 0 |
| 89 | 200 | 55 |
| 88 + 86 | 9 + 30 | 75 |
| 41 | 64 | 95 |
| 41 | 125 | 85 |
| 41 | 250 | 90 |
| 89 + 41 | 200 + 64 | 95 (98) |
| 89 + 41 | 200 + 125 | 95 (93) |
| 89 + 88 + 86 + 41 | 200 + 9 + 30 + 64 | 98 (99) |
| 89 + 88 + 86 + 41 | 200 + 9 + 30 + 125 | 100 (99) |

TABLE E2

Compounds 41, 91, and 86 on Cal. Watergrass (*E. oryzoides*) in soil from Japan (Toride Lt Clay) at the 31f stage.

| Compound No. | Rate g/ha | % Control |
|---|---|---|
| Untreated Check | 0 | 0 |
| 91 | 1200 | 25 |
| 86 | 50 | 35 |
| 41 | 64 | 95 |
| 41 | 125 | 85 |
| 41 | 250 | 90 |
| 91 + 86 | 1200 + 50 | 55 (51) |
| 91 + 86 + 41 | 1200 + 50 + 64 | 85 (98) |

TABLE E3

Compounds 41 and 92 with Cal. Watergrass (*E. oryzoides*) in soil from Japan (Toride Lt Clay) at the 31f stage.

| Compound No. | Rate g/ha | % Control |
|---|---|---|
| Untreated Check | 0 | 0 |
| 92 | 20 | 50 |
| 41 | 64 | 95 |
| 41 | 125 | 85 |
| 41 | 250 | 90 |
| 92 + 41 | 20 + 64 | 98 (98) |
| 92 + 41 | 20 + 125 | 95 (93) |
| 92 + 41 | 20 + 250 | 95 (95) |

TABLE E4

Compounds 41, 88, and 90 with Cal. Watergrass (*E. oryzoides*) in soil from Japan (Toride Lt Clay) at the 31f stage.

| Compound No. | Rate g/ha | % Control |
|---|---|---|
| Untreated Check | 0 | 0 |
| 88 + 90 | 9 + 4 | 60 |
| 41 | 64 | 95 |
| 41 | 125 | 85 |
| 41 | 250 | 90 |
| 88 + 90 + 41 | 9 + 4 + 64 | 90 (98) |
| 88 + 90 + 41 | 9 + 4 + 125 | 95 (94) |
| 88 + 90 + 41 | 9 + 4 + 250 | 100 (96) |

TABLE E5

Compounds 41 and 86 with Cal. Watergrass (*E. oryzoides*) in soil from Japan (Toride Lt Clay) at the 31f stage.

| Compound No. | Rate g/ha | % Control |
|---|---|---|
| Untreated Check | 0 | 0 |
| 86 | 50 | 35 |
| 41 | 64 | 95 |
| 41 | 125 | 85 |
| 41 | 250 | 90 |
| 86 + 41 | 50 + 64 | 85 (97) |
| 86 + 41 | 50 + 125 | 95 (90) |
| 86 + 41 | 50 + 250 | 90 (94) |

TABLE F1

Compounds 41, 88, 86, and 89 with Cal. Watergrass (*E. oryzoides*) in Tama soil at the 31f stage.

| Compound No. | Rate g/ha | % Control |
|---|---|---|
| Untreated Check | 0 | 0 |
| 89 | 300 | 20 |
| 88 + 86 | 9 + 30 | 45 |
| 41 | 64 | 75 |
| 41 | 250 | 75 |
| 89 + 88 + 86 | 300 + 9 + 30 | 45 (56) |
| 89 + 88 + 86 + 41 | 300 + 9 + 30 + 64 | 98 (86) |
| 89 + 88 + 86 + 41 | 300 + 9 + 30 + 250 | 95 (86) |

TABLE F2

Compounds 41, 89, and 87 with Cal. Watergrass (*E. oryzoides*) in Tama soil at the 31f stage.

| Compound No. | Rate g/ha | % Control |
|---|---|---|
| Untreated Check | 0 | 0 |
| 89 | 300 | 20 |
| 87 | 40 | 10 |
| 41 | 64 | 75 |
| 41 | 250 | 75 |
| 89 + 87 | 300 + 40 | 20 (28) |
| 89 + 87 + 41 | 300 + 40 + 64 | 90 (80) |
| 89 + 87 + 41 | 300 + 40 + 250 | 80 (80) |

TABLE F3

Compounds 41, 89, and 95 with Cal. Watergrass (*E. oryzoides*) in Tama soil at the 31f stage.

| Compound No. | Rate g/ha | % Control |
|---|---|---|
| Untreated Check | 0 | 0 |
| 89 | 300 | 20 |
| 95 | 90 | 10 |
| 41 | 64 | 75 |
| 41 | 250 | 75 |
| 89 + 95 | 300 + 90 | 40 (28) |
| 89 + 95 + 41 | 300 + 90 + 64 | 98 (85) |
| 89 + 95 + 41 | 300 + 90 + 250 | 90 (85) |

TABLE F4

Compounds 41, 88, and 86 with Cal. Watergrass (*E. oryzoides*) in Tama soil at the 31f stage.

| Compound No. | Rate g/ha | % Control |
|---|---|---|
| Untreated Check | 0 | 0 |
| 88 + 86 | 9 + 30 | 45 |
| 41 | 64 | 75 |
| 41 | 250 | 75 |
| 88 + 86 + 41 | 9 + 30 + 64 | 85 (78) |
| 88 + 86 + 41 | 9 + 30 + 250 | 90 (86) |

TABLE F5

Compounds 41 and 87 with Cal. Watergrass (*E. oryzoides*) in Tama soil at the 31f stage.

| Compound No. | Rate g/ha | % Control |
|---|---|---|
| Untreated Check | 0 | 0 |
| 87 | 40 | 10 |
| 41 | 64 | 75 |
| 41 | 250 | 75 |
| 87 + 41 | 40 + 64 | 85 (78) |
| 87 + 41 | 40 + 250 | 85 (78) |

TABLE F6

Compounds 41 and 95 with Cal. Watergrass (*E. oryzoides*) in Tama soil at the 31f stage.

| Compound No. | Rate g/ha | % Control |
|---|---|---|
| Untreated Check | 0 | 0 |
| 95 | 90 | 30 |
| 41 | 64 | 75 |
| 41 | 250 | 75 |
| 95 + 41 | 90 + 64 | 85 (82) |
| 95 + 41 | 90 + 250 | 100 (82) |

TEST G

Japonica Rice (M202) direct seeded into the pots and treated at 2 leaf stage. California Watergrass was grown to the 3 leaf stage (LW3) prior to treatment. Results of percent injury were done by visual ratings 17 days after treatment. Predicted herbicidal activity due to additive ffect, calculated based on Colby's equation, was also included in the Tables (numbers in parentheses).

TABLE G1

Compounds 93, 41, 88, and 86

| Compound No. | Rate g/ha | Rice | % Control LW3 |
|---|---|---|---|
| 88 + 86 | 9 + 30 | 25 | 55 |
| 41 | 64 | 0 | 70 |
| 41 | 250 | 0 | 80 |
| 93 | 150 | 10 | 15 |
| 93 + 41 | 150 + 64 | 10 | 70 (74.5) |
| 93 + 41 | 150 + 250 | 15 | 75 (83.0) |
| 93 + 41 + 88 + 86 | 150 + 64 + 6 + 30 | 20 | 80 |
| 93 + 41 + 88 + 86 | 150 + 250 + 6 + 30 | 25 | 80 |

TABLE G2

Compounds 93, 13, 88, and 86

| Compound No. | Rate g/ha | Rice | % Control LW3 |
|---|---|---|---|
| 93 | 150 | 10 | 15 |
| 13 | 64 | 0 | 80 |
| 13 | 250 | 0 | 75 |
| 93 + 13 | 150 + 64 | 0 | 75 (83.0) |
| 93 + 13 | 150 + 250 | 0 | 70 (78.8) |
| 93 + 13 + 88 + 86 | 150 + 64 + 6 + 30 | 25 | 85 |
| 93 + 13 + 88 + 86 | 150 + 250 + 6 + 30 | 25 | 80 |
| 93 + 41 + 88 + 86 | 150 + 250 + 6 + 30 | 25 | 80 |

TABLE G3

Compounds 94, 41, and 13

| Compound No. | Rate g/ha | Rice | % Control LW3 |
|---|---|---|---|
| 88 + 86 | 9 + 30 | 25 | 55 |
| 41 | 64 | 0 | 70 |
| 41 | 250 | 0 | 80 |
| 13 | 64 | 0 | 80 |
| 13 | 250 | 0 | 75 |
| 94 | 45 | 25 | 50 |
| 94 + 41 | 45 + 64 | 30 | 85 (82.5) |
| 94 + 41 | 45 + 250 | 25 | 85 (90.0) |
| 94 + 41 | 45 + 64 | 30 | 85 (90.0) |
| 94 + 41 | 45 + 250 | 25 | 80 (87.5) |

TABLE G4

Compounds 96, 41, 88, and 86

| Compound No. | Rate g/ha | Rice | % Control LW3 |
|---|---|---|---|
| 41 | 9 + 30 | 25 | 55 |
| 41 | 64 | 0 | 70 |
| 41 | 250 | 0 | 80 |
| 96 | 60 | 10 | 30 |
| 96 + 41 | 60 + 64 | 15 | 90 (79) |
| 96 + 41 | 60 + 250 | 10 | 85 (86) |
| 96 + 41 + 88 + 86 | 60 + 64 + 9 + 30 | 25 | 85 |
| 96 + 41 + 88 + 86 | 60 + 250 + 9 + 30 | 20 | 85 |

TABLE G5

Compounds 96, 13, 88, and 86

| Compound No. | Rate g/ha | Rice | % Control LW3 |
|---|---|---|---|
| 88 + 86 | 9 + 30 | 25 | 55 |
| 96 | 60 | 10 | 30 |
| 13 | 64 | 0 | 80 |
| 13 | 250 | 0 | 75 |
| 96 + 13 | 60 + 64 | 0 | 85 (86) |
| 96 + 13 | 60 + 250 | 10 | 90 (82.5) |
| 96 + 13 + 88 + 86 | 60 + 64 + 9 + 30 | 25 | 80 |
| 96 + 13 + 88 + 86 | 60 + 250 + 9 + 30 | 25 | 90 |

TABLE G6

Compounds 97, 41, 88, and 86

| Compound No. | Rate g/ha | Rice | % Control LW3 |
|---|---|---|---|
| 88 + 86 | 9 + 30 | 25 | 55 |
| 41 | 64 | 0 | 70 |
| 41 | 250 | 0 | 80 |
| 97 | 250 | 0 | 35 |
| 97 + 41 | 250 + 64 | 0 | 98 (82) |
| 97 + 41 | 250 + 250 | 0 | 95 (83.8) |
| 97 + 41 + 88 + 86 | 250 + 64 + 9 + 30 | 20 | 80 |
| 97 + 41 + 88 + 86 | 250 + 250 + 9 + 30 | 25 | 80 |

TABLE G7

Compounds 97, 13, 88, and 86

| Compound No. | Rate g/ha | Rice | % Control LW3 |
|---|---|---|---|
| 97 | 250 | 0 | 35 |
| 88 + 86 | 9 + 30 | 25 | 55 |
| 13 | 64 | 0 | 80 |
| 13 | 250 | 0 | 75 |
| 97 + 13 | 250 + 64 | 0 | 90 (87) |
| 97 + 13 | 250 + 250 | 0 | 95 |
| 97 + 13 + 88 + 86 | 250 + 64 + 9 + 30 | 20 | 80 |
| 97 + 13 + 88 + 86 | 250 + 64 + 9 + 30 | 20 | 80 |

What is claimed is:

1. Agriculturally suitable compositions for controlling the growth of undesired vegetation in a crop comprising an effective amount of a compound of Formula I

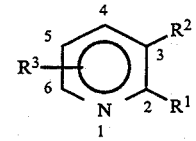

wherein $R^1$ is Cl, Br, I, OCH$_3$, OCHF$_2$ or OCF$_3$;

$R^2$ is CN, CO$_2$R$^4$, CHO, C(X)NR$^{17}$R$^{18}$, C(S)OR$^6$, C≡CH, CHR$^{19}$OR$^{20}$, CH=NOR$^7$ or CH=CR$^{21}$R$^{22}$;

$R^3$ is n-propyl; C$_4$-C$_{10}$ alkyl; n-propyl or C$_4$-C$_7$ alkyl substituted with one or more halogen, OR$^8$, SR$^9$ or NR$^{10}$R$^{11}$; C$_1$-C$_3$ alkyl substituted with OR$^{16}$, CO$_2$(C$_1$-C$_2$ alkyl) or phenyl optionally substituted with one or more CH$_3$, CF$_3$, OCH$_3$, SCH$_3$ or halogen; C$_3$-C$_6$ cycloalkyl; CH$_2$(C$_3$-C$_6$ cycloalkyl); phenyl optionally substituted with one or more CH$_3$, CF$_3$, OCH$_3$, SCH$_3$ or halogen; C$_2$-C$_6$ alkenyl optionally substituted with one or more halogen or CO$_2$ (C$_1$-C$_2$ alkyl); OR$^{12}$; SR$^{13}$; or NR$^{14}$R$^{15}$;

$R^4$ is H, C$_1$-C$_2$ alkyl,

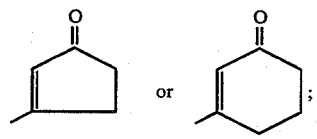

$R^6$, $R^7$, $R^8$, $R^9$, $R^{10}$ and $R^{11}$ are independently H or C$_1$-C$_2$ alkyl;

$R^{12}$ and $R^{13}$ are independently C$_2$-C$_{10}$ alkyl optionally substituted with one or more halogen, OR$^8$, SR$^9$ or NR$^{10}$R$^{11}$; phenyl optionally substituted with one or more CH$_3$, CF$_3$, OCH$_3$, SCH$_3$ or halogen; or benzyl;

$R^{14}$ and $R^{15}$ are independently H or C$_1$-C$_2$ alkyl, or may be taken together as —(CH$_2$)$_4$—, —(CH$_2$)$_5$— or —(CH$_2$CH$_2$OCH$_2$CH$_2$)—;

$R^{16}$ is H, C$_1$-C$_8$ alkyl; benzyl optionally substituted with one or more CH$_3$, CF$_3$, OCH$_3$, SCH$_3$ or halogen; or phenyl optionally substituted with one or more CH$_3$, CF$_3$, OCH$_3$, SCH$_3$ or halogen;

$R^{17}$ is H, C$_1$-C$_2$ alkyl or phenyl optionally substituted with one or more CH$_3$, CF$_3$, OCH$_3$, SCH$_3$ or halogen;

$R^{18}$ is H, C$_1$-C$_2$ alkyl, C$_3$-C$_6$ cycloalkyl, CH$_2$(C$_3$-C$_6$ cycloalkyl), O(C$_1$-C$_4$ alkyl), O-allyl or may be taken together with $R^{17}$ as $-(CH_2)_4-$, $-(CH_2)_5-$ or $-(CH_2CH_2OCH_2CH_2)-$;

$R^{19}$ is H or $C_1-C_2$ alkyl;

$R^{20}$ is H or $C(O)CH_3$;

$R^{21}$ and $R^{22}$ are independently H, CN, $CO_2R^4$, $C(X)NR^{17}R^{18}$ or halogen;

X is O or S;

or their N-oxides or agriculturally suitable salts thereof provided that when $R^1$ is Cl, Br or I, and $R^2$ is CN, $CO_2R^4$ or $C(O)NR^{17}R^{18}$, then $R^3$ is other than optionally substituted 5-phenyl and at least one of the following: surfactant, solid, or liquid diluent.

2. The compositions of claim 1 wherein
$R^1$ is Cl, Br, I or $OCH_3$;
$R^2$ is CN, $CO_2R^4$, CHO, $C(X)NH_2$, $C(X)NH(C_1-C_2$ alkyl), $C(X)N(C_1-C_2$ alkyl)$_2$, $C(S)OR^6$ or $C\equiv CH$;
$R^3$ is n-propyl, $C_4-C_6$ alkyl, $C_3-C_6$ cycloalkyl or phenyl;
$R^4$ is H or $C_1-C_2$ alkyl; and
$R^6$ is $C_1-C_2$ alkyl.

3. The compositions of claim 1 wherein
$R^1$ is Cl, Br or I;
$R^2$ is CN, $CO_2H$, $CO_2CH_3$, $CO_2CH_2CH_3$, CHO, $C(O)NH_2$, $C(O)NHCH_3$, $C(O)N(CH_3)_2$, $CH_2OH$ or $CH=NOR^7$;
$R^3$ is n-propyl; $C_4-C_7$ alkyl; $C_2$ alkyl substituted with phenyl optionally substituted with one or more $CH_3$, $CF_3$, $OCH_3$, $SCH_3$ or halogen; $CH_2$ ($C_3-C_6$ cycloalkyl); or phenyl optionally substituted with one or more $CH_3$, $CF_3$, $OCH_3$, $SCH_3$ or halogen.

4. The compositions of claim 3 wherein
$R^1$ is Cl or Br;
$R^2$ is CN, $CO_2H$ or $C(O)NH_2$;
$R^3$ is $C_4-C_7$ alkyl or $CH_2(C_3-C_6$ cycloalkyl).

5. The compositions of of claim 4 wherein $R^3$ is substituted at the 6-pyridine position.

6. The composition of claim 5 wherein the compounds are 2-bromo-6-(3-methylbutyl)-3-pyridinecarboxamide or 2-chloro-6-(3-methylbutyl)-3-pyridinecarboxamide.

7. A method for controlling the growth of barnyardgrass or California watergrass in a crop by applying to the locus of the crop to be protected an effective amount of a composition of any one of claims 1-6.

8. The compositions of claim 1 wherein there is in combination with the compound of Formula I when $R^1$ is Br or Cl, $R^2$ is $C(O)NH_2$ and $R^3$ is $CH_2CH_2CH(CH_3)_2$, one or more herbicidal compound selected from the group consisting of bensulfuron methyl; mefenacet; metsulfuron methyl; pyrazosulfuron ethyl; butachlor; N-[2-(2-methoxyethoxyphenylsulfonyl]-$N^1$-4,6-dimethoxy-1,3,5-triazin-2-yl urea; N-[[(4,6-dimethoxypyrimidin-2-yl)amino]carbonyl]-1-methyl-4-(2-methyl-2H-tetrazol-5-yl)-1H-pyrazole-5-sulfonamide; S,S-dimethyl 2-(difluoromethyl)-4-(2-methylpropyl)-6-(trifluoromethyl)-3,5-pyridinecarbothiate; and 3-chloro-N[[(4,6-dimethoxy-2-pyrimidinyl)amino]carbonyl]imidazo[1,2-a]pyridine-3-sulfonamide.

9. The composition of claim 8 wherein the herbicidal compound is selected from butachlor and 3-chloro-N-[[(4,6-dimethoxy-2-pyrimidinyl)amino]carbonyl]imidazo-[1,2-a]pyridine-3-sulfonamide.

10. The composition of claim 8 wherein $R^1$ is Br and the herbicidal compound is mefenacet.

* * * * *